United States Patent
Costantine et al.

(10) Patent No.: US 11,134,860 B2
(45) Date of Patent: Oct. 5, 2021

(54) ANTENNA DESIGN FOR BIOMARKER MONITORING AND METHODS OF USE

(71) Applicant: American University of Beirut, Beirut (LB)

(72) Inventors: Joseph Costantine, Albuquerque, NM (US); Rouwaida Kanj, Portland, OR (US); Assaad Eid, Paris (FR); Jessica Hanna, Ferzol (LB); Ali H. Ramadan, Beirut (LB); Youssef Tawk, Albuquerque, NM (US)

(73) Assignee: American University of Beirut, Beirut (LB)

(*) Notice: Subject to any disclaimer, the term of this patent is extended or adjusted under 35 U.S.C. 154(b) by 230 days.

(21) Appl. No.: 16/453,264

(22) Filed: Jun. 26, 2019

(65) Prior Publication Data
US 2019/0388000 A1    Dec. 26, 2019

Related U.S. Application Data

(60) Provisional application No. 62/690,110, filed on Jun. 26, 2018.

(51) Int. Cl.
*A61B 5/0507* (2021.01)
*A61B 5/145* (2006.01)
*A61B 5/00* (2006.01)

(52) U.S. Cl.
CPC ........ *A61B 5/0507* (2013.01); *A61B 5/14532* (2013.01); *A61B 5/7275* (2013.01); *A61B 5/14546* (2013.01); *A61B 2562/0228* (2013.01)

(58) Field of Classification Search
CPC . A61B 5/0507; A61B 5/14532; A61B 5/7275; A61B 5/14546; A61B 2562/0228; Y01A 90/10; G16H 50/30; H01Q 13/10; H01Q 13/103; H01Q 9/44
See application file for complete search history.

(56) References Cited

U.S. PATENT DOCUMENTS

| | | | |
|---|---|---|---|
| 6,307,519 B1 | 10/2001 | Livingston et al. | 343/767 |
| 7,746,276 B2 | 6/2010 | Surducan et al. | 343/700 |
| 7,825,868 B2 | 11/2010 | Sabet et al. | 343/767 |
| 8,369,796 B2 | 2/2013 | Pan et al. | 455/78 |
| 8,882,670 B2 | 11/2014 | Hancock | A61B 5/14546 |
| 8,957,817 B2 | 2/2015 | Jiang et al. | H01Q 13/103 |
| 8,957,827 B1 | 2/2015 | Lee et al. | 343/852 |
| 9,044,158 B2 | 6/2015 | Varahramyan et al. | A61B 5/05 |
| 9,119,580 B2 | 9/2015 | Fischer | A61B 5/14532 |
| 2014/0163338 A1* | 6/2014 | Roesicke | A61B 5/0031 600/309 |

(Continued)

OTHER PUBLICATIONS

J. Hanna, J. Costantine, R. Kanj, A. A. Eid, Y. Tawk and A. H. Ramadan, "A Slot Antenna for Non-invasive Detection of Blood Constituents Concentrations," 2019 IEEE International Symposium on Antennas and Propagation and USNC-URSI Radio Science Meeting, Atlanta, GA, USA, 2019, pp. 1003-1004 (Year: 2019).*

(Continued)

*Primary Examiner* — Sean P Dougherty
*Assistant Examiner* — Kyle W. Kretzer
(74) *Attorney, Agent, or Firm* — J. Peter Paredes; Amin Talati Wasserman LLP

(57) ABSTRACT

Provided herein are systems, methods and apparatuses for an Antenna Design for Biomarker Monitoring.

11 Claims, 68 Drawing Sheets

(56) References Cited

U.S. PATENT DOCUMENTS

| | | | |
|---|---|---|---|
| 2017/0164878 A1 | 6/2017 | Connor | A61B 5/14532 |
| 2017/0229763 A1* | 8/2017 | Barak | H01Q 1/38 |
| 2017/0303858 A1* | 10/2017 | Barak | A61B 5/6825 |

OTHER PUBLICATIONS

[Item U continued] doi: 10.1109/APUSNCURSINRSM.2019. 8889278. (Year: 2019).*

J. Hanna, M. Bteich, Y. Tawk, A. H. Ramadan, B. Dia, F. A. Asadallah, A. Eid, R. Kanj, J. Costantine, and A. A. Eid, "Noninvasive, wearable, and tunable electromagnetic multisensing system for continuous glucose monitoring, mimicking vasculature anatomy," Science Advances, Jun. 10, 2020, vol. 6, No. 24 (Year: 2020).*

[Item W continued] pp. 1-11, doi: 10.1126/sciadv.aba5320 (Year: 2020).*

F. A. Asadallah, J. Costantine and Y. Tawk, "A Multiband Compact Reconfigurable PIFA Based on Nested Slots," in IEEE Antennas and Wireless Propagation Letters, vol. 17, No. 2, pp. 331-334, Feb. 2018, doi: 10.1109/LAWP.2017.2788465. (Year: 2018).*

Ali, MS et al., "Non-invasive blood glucose measurement performance analysis through UWB imaging," 2016 3rd International Conference on Electronic Design (ICED), Phuket, pp. 513-516 (Aug. 2016).

Cano-Garcia, H., "New methods for determining the complex permittivity of different glucose concentrations by waveguide and antenna measurements at v-band" Universitat Politécnica de Catalunya, pp. 1-73 (Sep. 2013).

Chen, Z. et al., "Stretchable conductive elastomer for wireless wearable communication applications" Scientific Reports, 7: 10958, pp. 1-8 (Sep. 2017).

Kim, S. et al., "Parylene coated waterproof washable inkjet-printed dual-band antenna on paper substrate" International Journal of Microwave and Wireless Technologies 10, 814-818 (May 2, 2018).

Saha, S. et al., "A Glucose Sensing System Based on Transmission Measurements at Millimetre Waves using Micro strip Patch Antennas"—Scientific Reports, pp. 1-11 (Jul. 2017).

Shao, et al., "A novel miniature spiral sensor for non-invasive blood glucose monitoring," 2016 10th European Conference on Antennas and Propagation (EuCAP), Davos, pp. 1-2 (2016).

Shinde, P et al., Feasibility Study of Non Invasive Blood Glucose Monitoring using Wideband Antenna' International Journal of Advanced Research in Electronics and Communication Engineering (IJARECE) vol. 5, Issue 5, pp. 1231-1234 (May 2016).

Sidley, M. et al., "Feasibility of blood glucose estimation from real time monitoring," 2013 IEEE Antennas and Propagation Society International Symposium (APSURSI), Orlando, FL, pp. 2055-2056 (2013).

Sidley, M. et al., "Non-invasive estimation of blood glucose a feasibility study," 2013 IEEE Applied Electromagnetics Conference (AEMC), Bhubaneswar, pp. 1-2 (2013).

https://www.dupont.com/electronic-materials/kapton-polyimide-film.html (Jun. 2019).

International Search Report and Written Opinion issued in corresponding foreign application No. PCT/US2019/039238, pp. 1-8 (dated Oct. 3, 2019).

Asadallah, F.A. et al., "A Multiband Compact Reconfigurable PIFA Based on Nested Slots," IEEE Antennas and Wireless Propagation Letters, vol. 17, No. 2, pp. 331-334, Feb. 2018.

Chen, Zhibo et al., "Stretchable conductive elastomer for wireless wearable communication applications," Nature Scientific Reports 7, 10958, pp. 1-8, Sep. 8, 2017.

Gowen, A.A. et al. "Preventing over-fitting in PLS calibration models of near-infared (NIR) spectroscopy data using regression coefficients," Journal of Chemometrics, 25, pp. 371-381, Oct. 22, 2010.

Hargrove, L. et al., "Principal Components Analysis Preprocessing to Reduce Controller Delays in Pattern Recognition Based Myoelectric Control," 29th Annual International Conference of the IEEE Engineering in Medicine and Biology Society, pp. 6511-6514, Aug. 2007.

Jin, B. et al., "Modeling and Analysis of Soft-Test/Repair for CCD-Based Digital X-Ray Systems, " IEEE Transactions on Instrumentation and Measurement, vol. 52, Issue 6, pp. 1713-1721, Dec. 2003.

Sipila, M. et al., "High-Frequency Periodic Time-Domain Waveform Measurement System," IEEE Transactions on Microwave Theory and Techniques, vol. 36, Issue 10, pp. 1397-1405, Oct. 1988.

\* cited by examiner

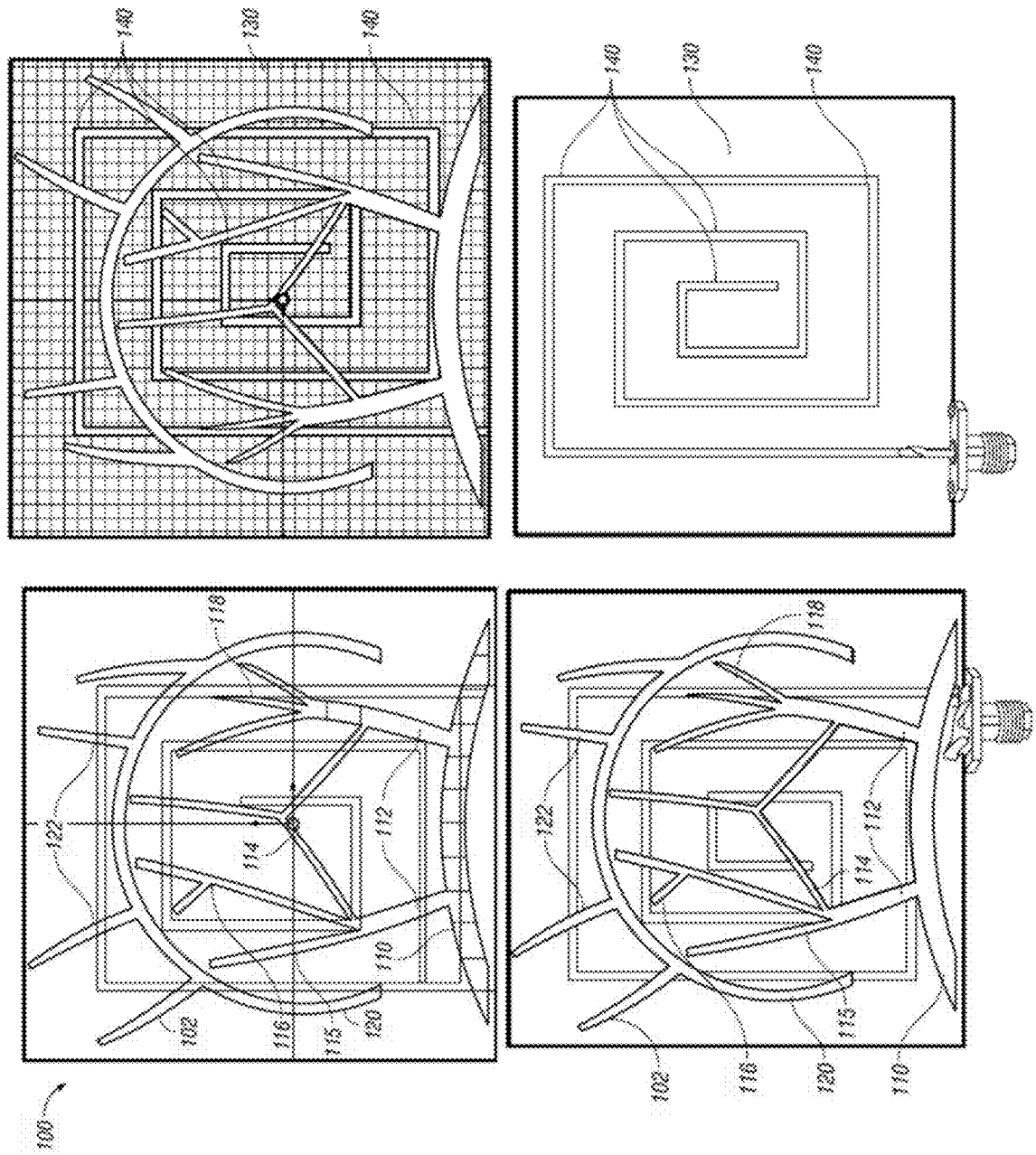

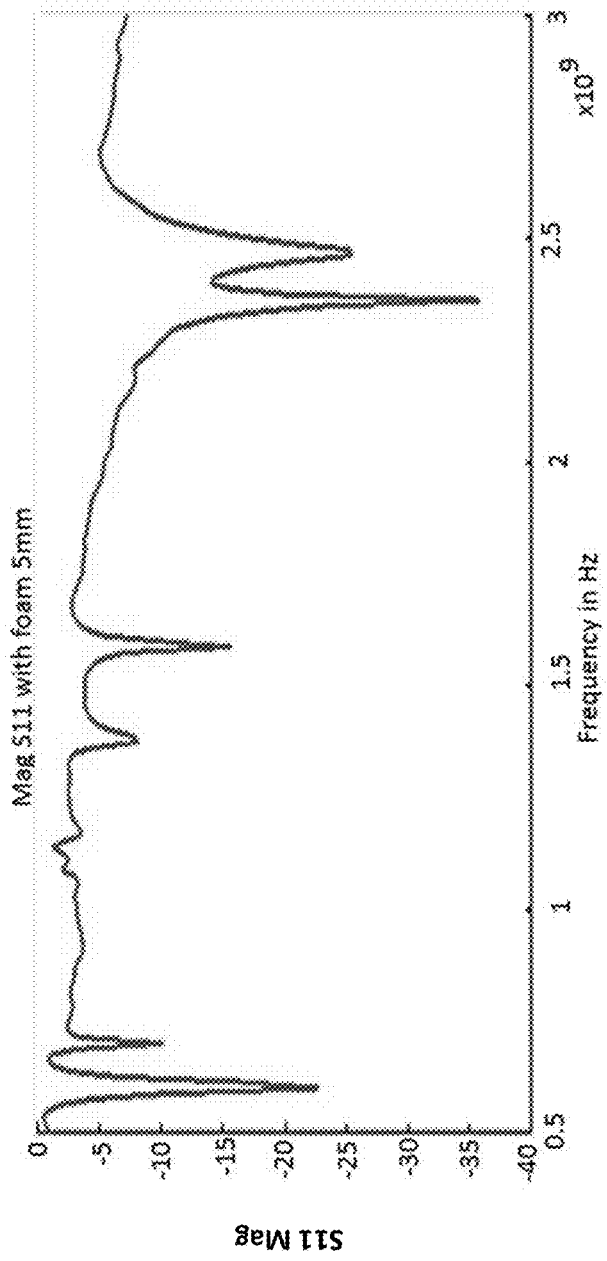
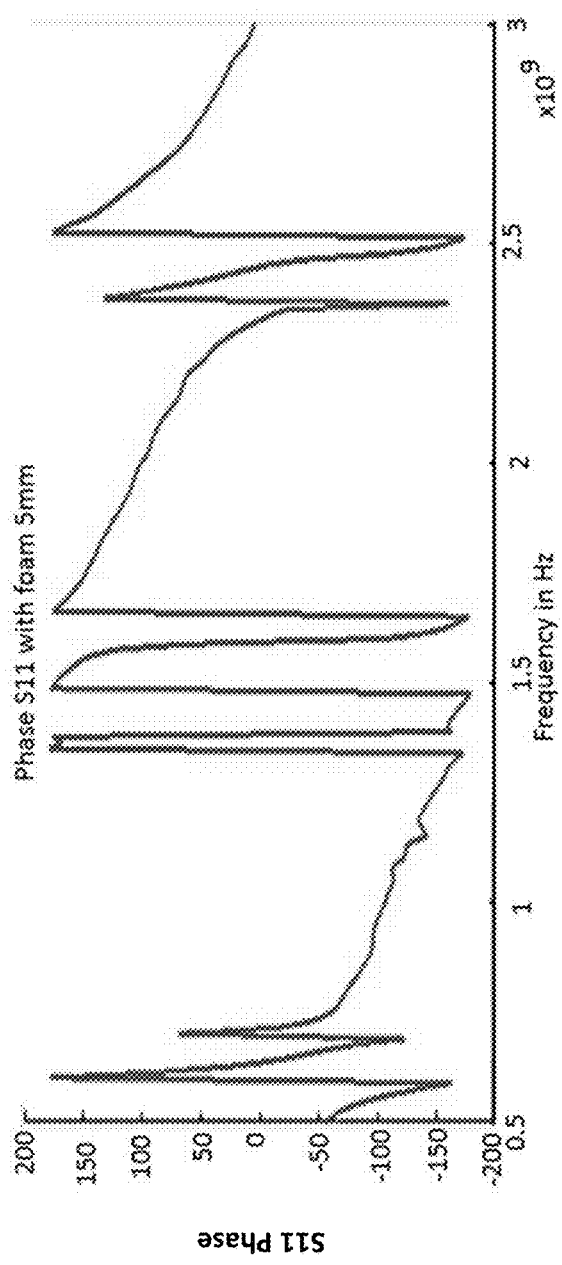
FIG. 3A
FIG. 3B

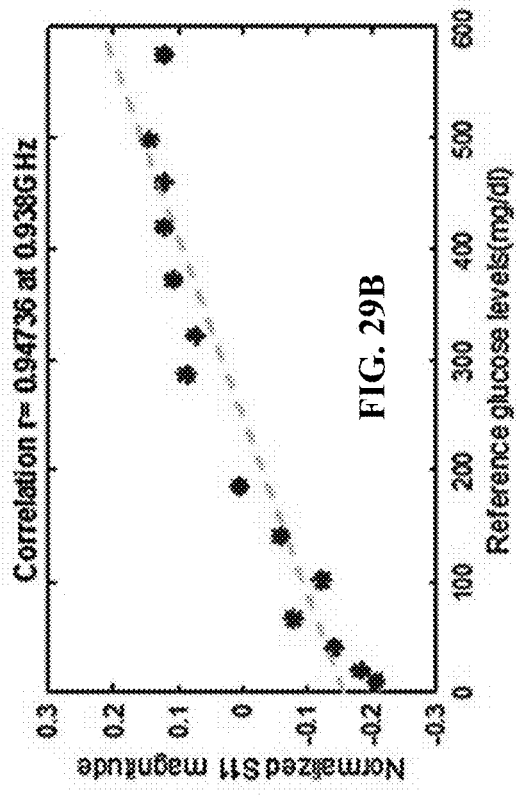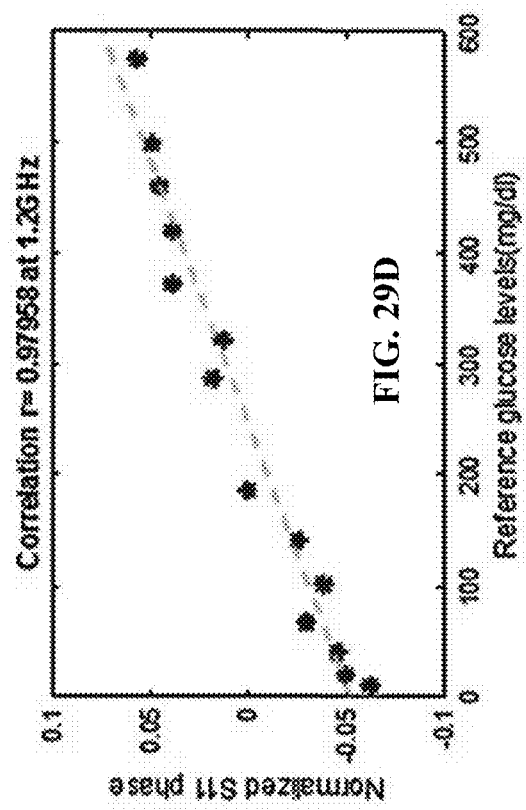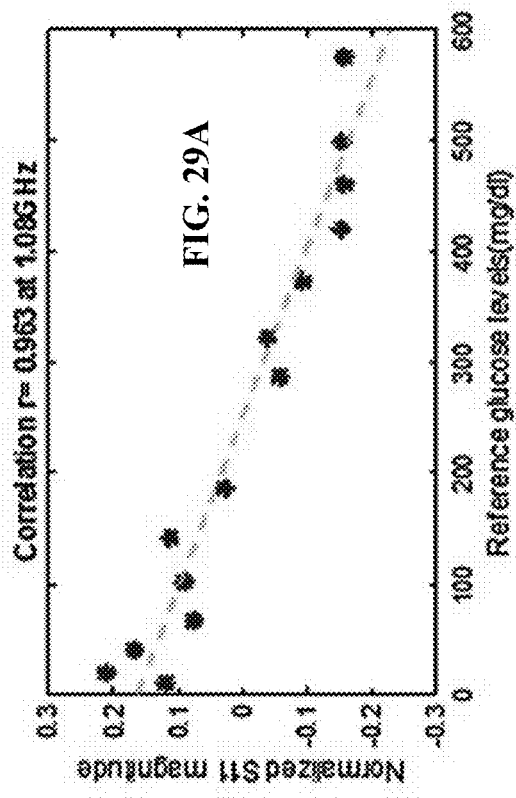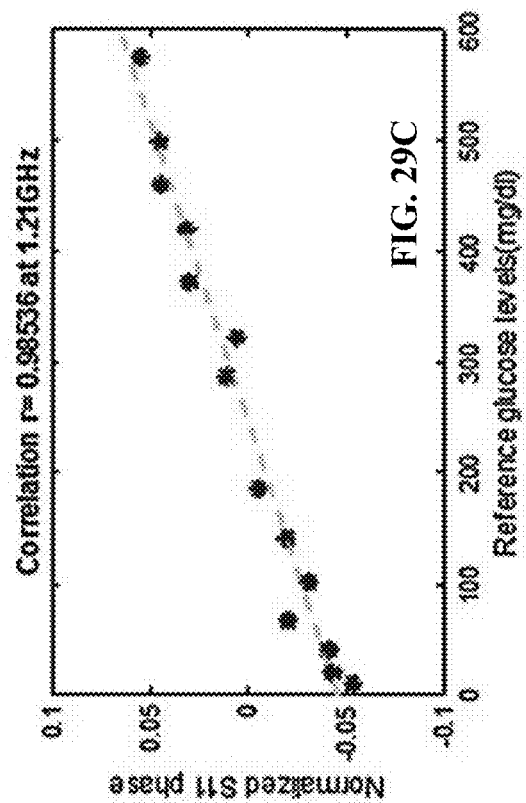
FIG. 29A
FIG. 29B
FIG. 29C
FIG. 29D

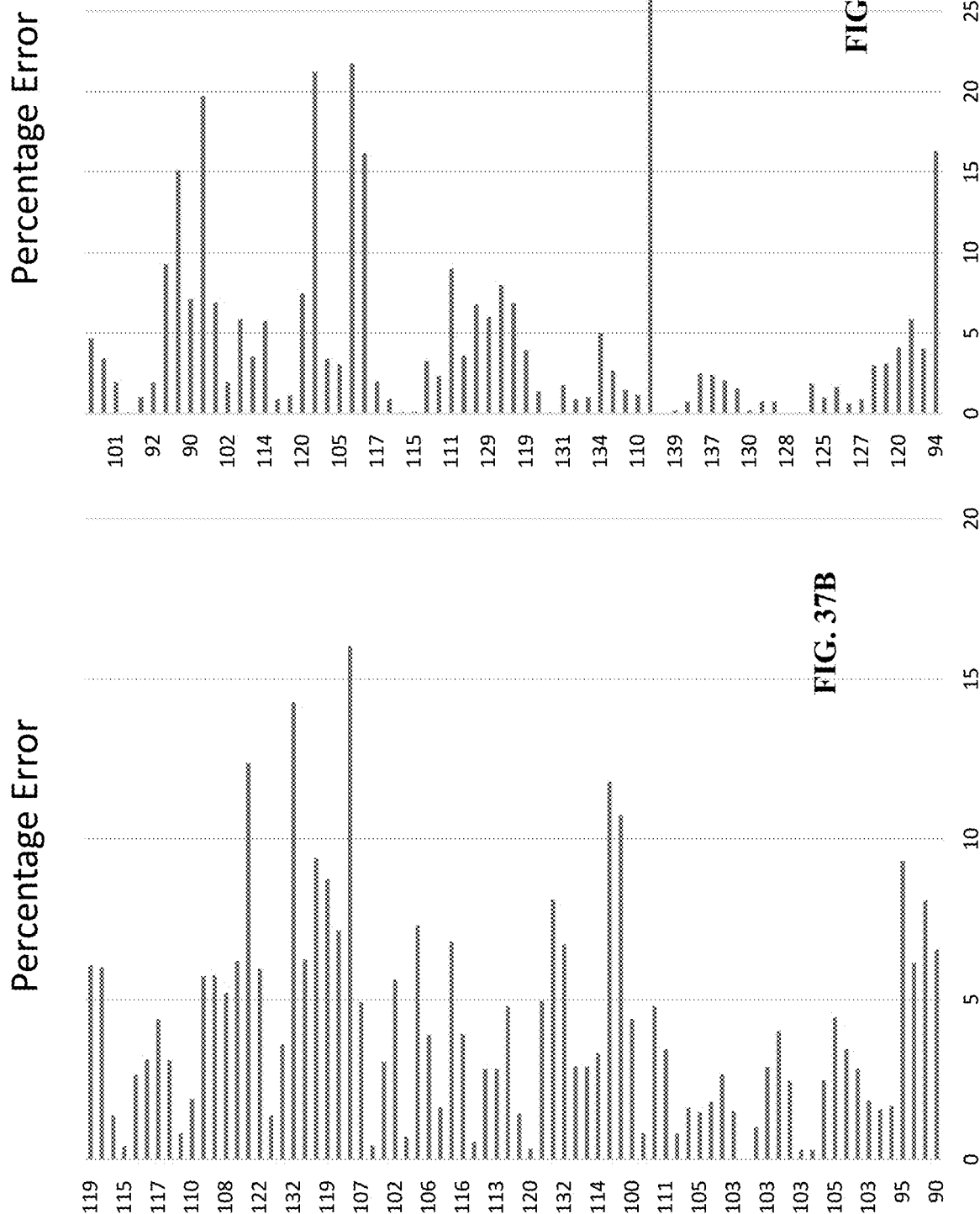

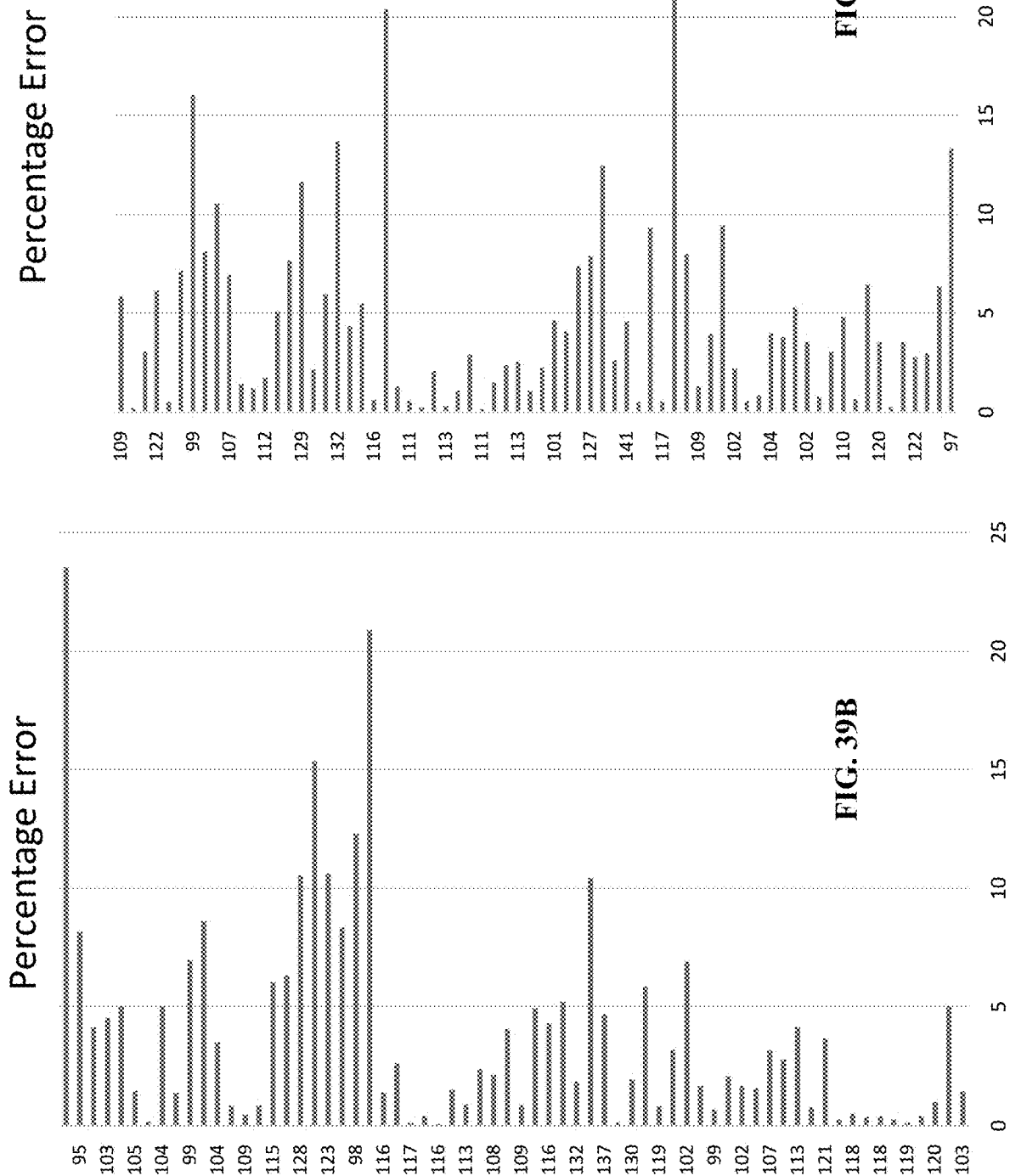

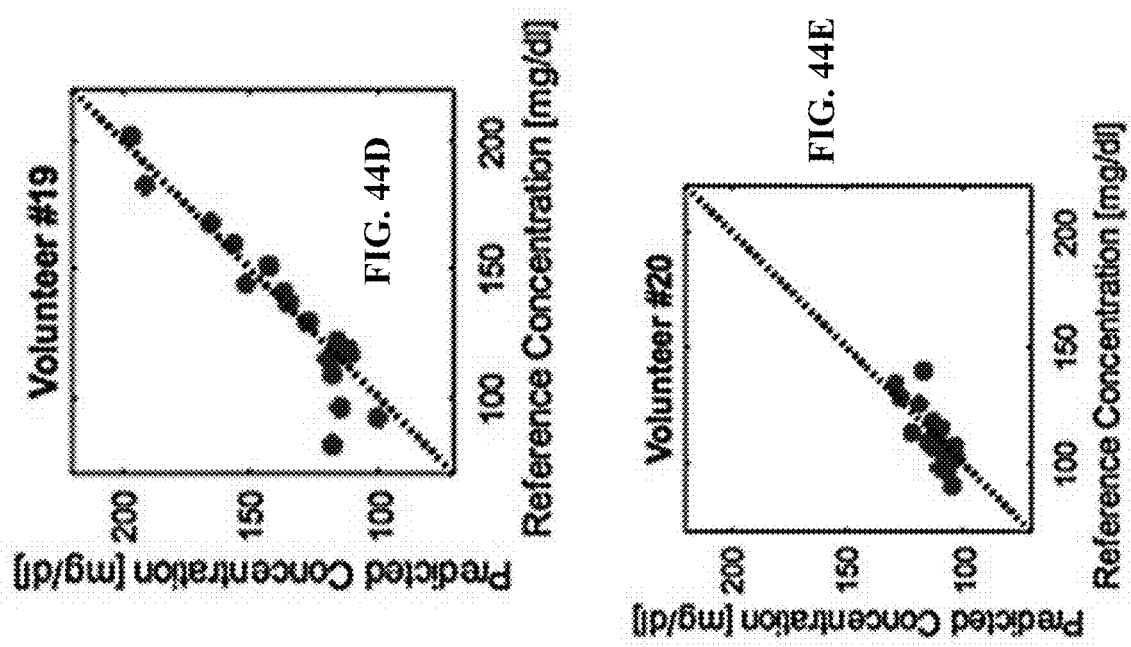
FIG. 44D
FIG. 44E
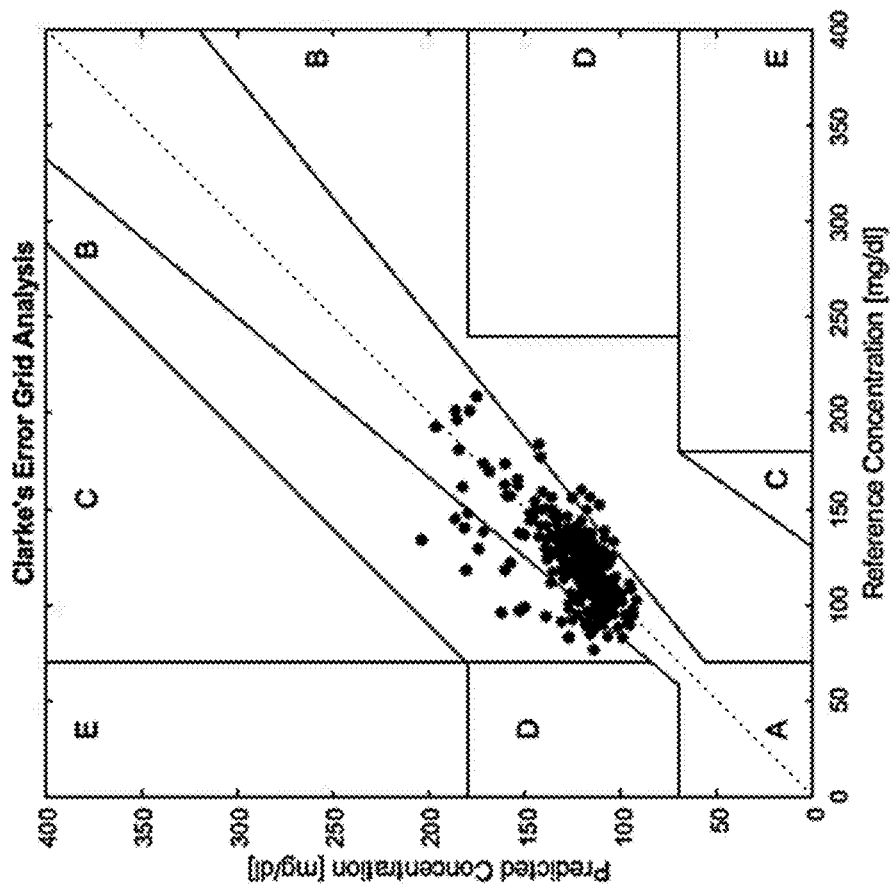
FIG. 43A

Rigid Antenna

| Volunteer | #1 | #2 | #3 | #4 | #5 | #6 | #7 | #8 | #9 | #10 | Total Average |
|---|---|---|---|---|---|---|---|---|---|---|---|
| LW PLS | 3.9 | 3.3 | 11.6 | 2.3 | 7.9 | 5.0 | 10.7 | 5.4 | 6.6 | 14.9 | 7.1 |
| PLS | 2.6 | 3.3 | 12.0 | 3.7 | 7.9 | 5.0 | 10.6 | 6.1 | 6.8 | 15.4 | 7.3 |
| GP | 2.0 | 2.8 | 11.3 | 1.8 | 7.0 | 5.4 | 8.2 | 5.2 | 5.8 | 15.4 | 6.5 |
| RBF | 2.4 | 2.6 | 12.4 | 1.4 | 7.4 | 5.6 | 7.8 | 5.0 | 16.0 | 14.2 | 7.5 |

FIG. 47

Flexible Antenna

| Volunteer | #1 | #2 | #3 | #4 | #5 | #6 | #7 | #8 | #9 | #10 | Total Average |
|---|---|---|---|---|---|---|---|---|---|---|---|
| LW PLS | 3.4 | 2.9 | 10.3 | 1.8 | 7.5 | 5.9 | Nan | 6.3 | 6.2 | 11.5 | 6.2 |
| PLS | 3.4 | 2.9 | 10.5 | 1.8 | 7.5 | 5.9 | Nan | 6.3 | 6.7 | 11.3 | 6.3 |
| GP | 2.4 | 3.4 | 12.2 | 1.7 | 6.7 | 7.1 | Nan | 5.2 | 4.2 | 13.2 | 6.2 |
| RBF | 2.8 | 3.5 | 16.3 | 1.6 | 9.0 | 13.9 | Nan | 4.7 | 14.7 | 13.6 | 8.9 |

FIG. 49

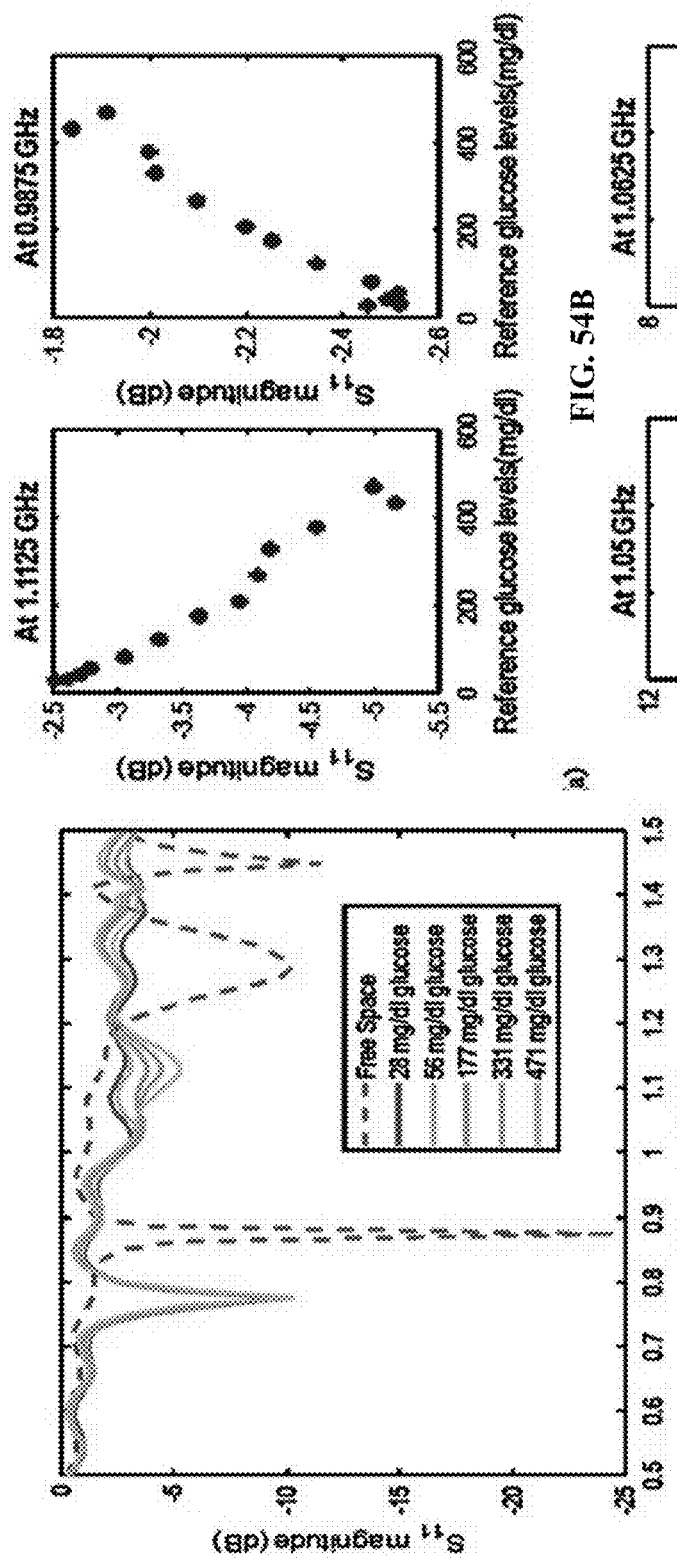
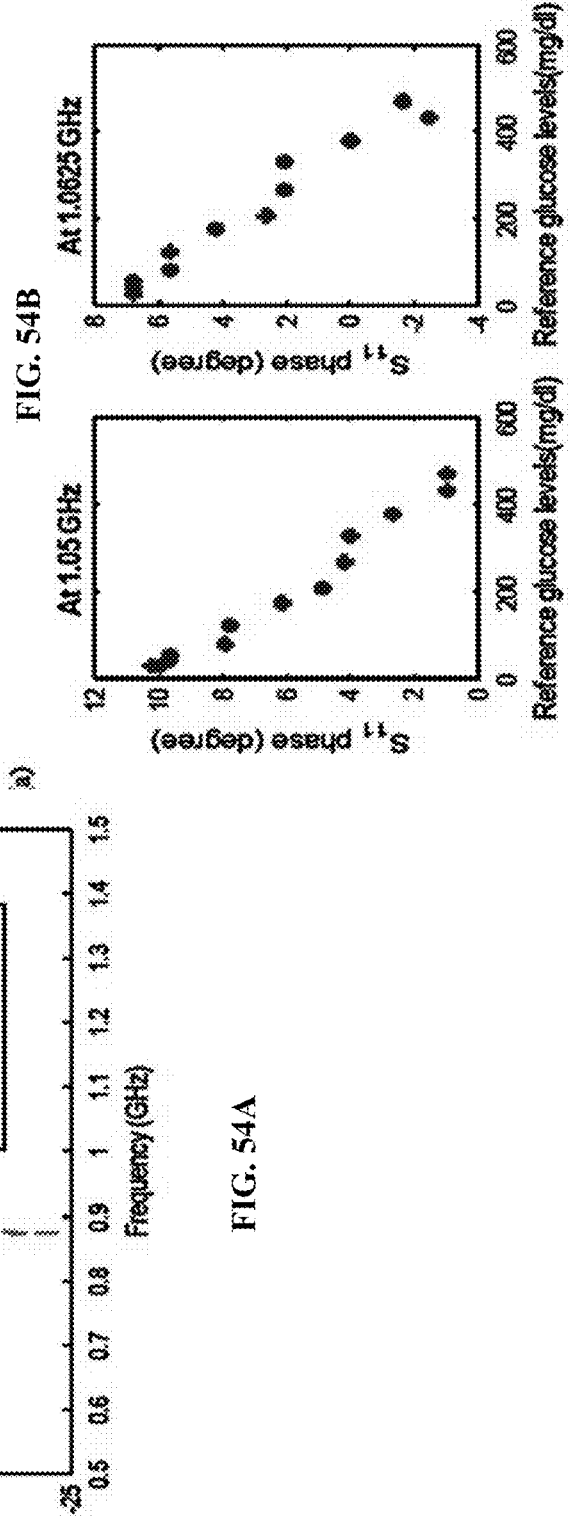
FIG. 54B
FIG. 54C
FIG. 54A

ANTENNA DESIGN FOR BIOMARKER MONITORING AND METHODS OF USE

CROSS REFERENCE TO RELATED APPLICATIONS

The present application claims priority to U.S. provisional application Ser. No. 62/690,110, filed Jun. 26, 2018, herein incorporated by reference in its entirety.

BACKGROUND

The invention generally relates to antennas and monitoring devices.

Many research groups have studied the potential of a radio frequency reflectometry technique in measuring blood glucose levels. Buford Randall Jean and Eric C, Green at Baylor University explored the usage of antennas to estimate the glucose levels. They tested different antenna's design and the results of regular blood and modified Blood composition for each sensor were compared. The best design was chosen upon the max shift of S11 and S21 with change in blood permittivity. The Single Spiral Micro-strip designed to resonant at 1.5 GHZ shows changes in its response when exposed to materials with different permittivity.

Another RF system was developed by J. Venkataraman and M. Sidley from Rochester Institute of Technology. Their device consists of a microstrip antenna mounted on the patient's arm. During their early research, they tested three different types of antennas in order to determine which one would deliver the best results in terms of monitoring the variations of the glucose levels. First a spiral and serpentine antenna were designed at 2.45 GHz and tested. Later, a planer dipole was developed with a resonate frequency at 1.4 GHz which outperform the two previous designs. They were able to achieve a shift of 1 MHz in resonate frequency for a shift of 14.62 mg/dl in glucose concentration.

Jinjin Shao et al. proposed a four-arm spiral microstrip antenna to detect the variation of glucose concentration. It's designed to resonate at 5 GHz with a very narrow bandwidth. They tested their sensor using a finger model in HFSS by varying its relative permittivity with a step of 0.01. A very small frequency shift was achieved by their sensor. M. S. Ali et al. investigated another RF sensor to monitor the glucose variation. They designed an ultra-wide band rectangular patch antenna resonating at 4.7 GHz with a bandwidth of 8.77 GHz ranging from 3.23 to 12 GHz and a gain of 6.09 dB. Their sensor composed of two UWB planar antennas and a signal processing technique based with an artificial neural network to predict the glucose levels.

H. C. Garcia et al. [8], in collaboration with mediwise, designed other noninvasive techniques. The sensor is composed of two rectangular microstrip patch antennas with dimensions of 1.5 by 1.5 mm designed to resonant at 60 GHz. The sensor was utilized to monitor several concentrations of water-based glucose-loaded liquid samples enclosed in an acrylic tank. Recently they tested their sensing device on patents during in-vivo Intravenous Glucose Tolerance Test (IVGTT). They were able to detect a sensitivity of 1.33 mmol/l (24 mg/dl) in water-based glucose-loaded liquid samples and 4 mmol/l (=72 mg/dl) in clinical trials. The present invention attempts to solve these problems as well as others.

SUMMARY OF THE INVENTION

Provided herein are systems, methods and apparatuses for an Antenna Design for Biomarker Monitoring.

The methods, systems, and apparatuses are set forth in part in the description which follows, and in part will be obvious from the description, or can be learned by practice of the methods, apparatuses, and systems. The advantages of the methods, apparatuses, and systems will be realized and attained by means of the elements and combinations particularly pointed out in the appended claims. It is to be understood that both the foregoing general description and the following detailed description are exemplary and explanatory only and are not restrictive of the methods, apparatuses, and systems, as claimed.

BRIEF DESCRIPTION OF THE DRAWINGS

In the accompanying figures, like elements are identified by like reference numerals among the several preferred embodiments of the present invention.

FIG. 1A is a schematic representing the simulated structure with the feeding line and FIG. 1B is a front view representing the fabricated structure with the feeding line.

FIG. 3A is a graph of the measured S11 Mag (a); FIG. 3B is a graph of the S11 Phase of the one sensor embodiment.

FIG. 19A is a graph showing the flexible antenna's response (S11) to glucose variation. Glucose concentration of the FBS solution is varied with very small steps from 50 mg/dl to 500 mg/dl. FIG. 19A is a graph showing S11 magnitude versus to the reference glucose levels obtained by the commercial invasive glucometer. The cyan line is the S11 fitted curve showing the trend of the antenna's response when the glucose levels increase. These S11 magnitude values are recorded at 1.15 GHz which correspond to one of the frequencies achieving high linear correlation between the S11 and the glucose reference levels with r=0.96. FIG. 19B is a graph showing the S11 phase versus to the reference glucose levels. These S11 phase values are recorded at 1.575 GHz, achieving a correlation of −0.98.

FIG. 28C is a graph showing the S11 magnitude versus the reference glucose levels obtained by the commercial invasive glucometer, showing a good correlation between the two curves (r=0.97).

FIGS. 29A-29D are graphs of the flexible antennae results.

FIG. 31C is a graph showing the reference glucose levels for PLS, GP, RBF, and LASSO.

FIG. 32C is a graph showing the reference glucose levels for PLS, GP, RBF, and LW PLS.

FIG. 37B is a bar graph showing the percentage error.

FIG. 38B is a bar graph showing the percentage error.

FIG. 39B is a bar graph showing the percentage error.

FIG. 40B is a bar graph showing the percentage error.

FIG. 43A is a graph showing the Clarke Error Grid Statistics for the in vivo results with Flexible Antenna (training ⅔, Testing ⅓)

FIGS. 44A-44E are graphs for the Flexible Antenna (training ⅔, Testing ⅓) for Volunteers 1-20.

FIG. 47 is a table showing the mean % Error for each volunteer for the rigid antenna in the In Vivo Experiment on Human subjects Experimental Setup.

FIG. 49 is a table of the In Vivo Experiment on Human subjects Experimental Setup for the flexible antenna and the Mean % Error for each volunteer.

FIG. 54A is a graph the S11 response to glucose variation during in vitro experiment. FIG. 54B are graphs of the S11 magnitude monitored at different frequencies as a function of glucose concentration levels; FIG. 54C are graphs of the phase monitored at different frequencies as a function of glucose concentration levels.

DETAILED DESCRIPTION OF THE INVENTION

Figures 1C, 1D:
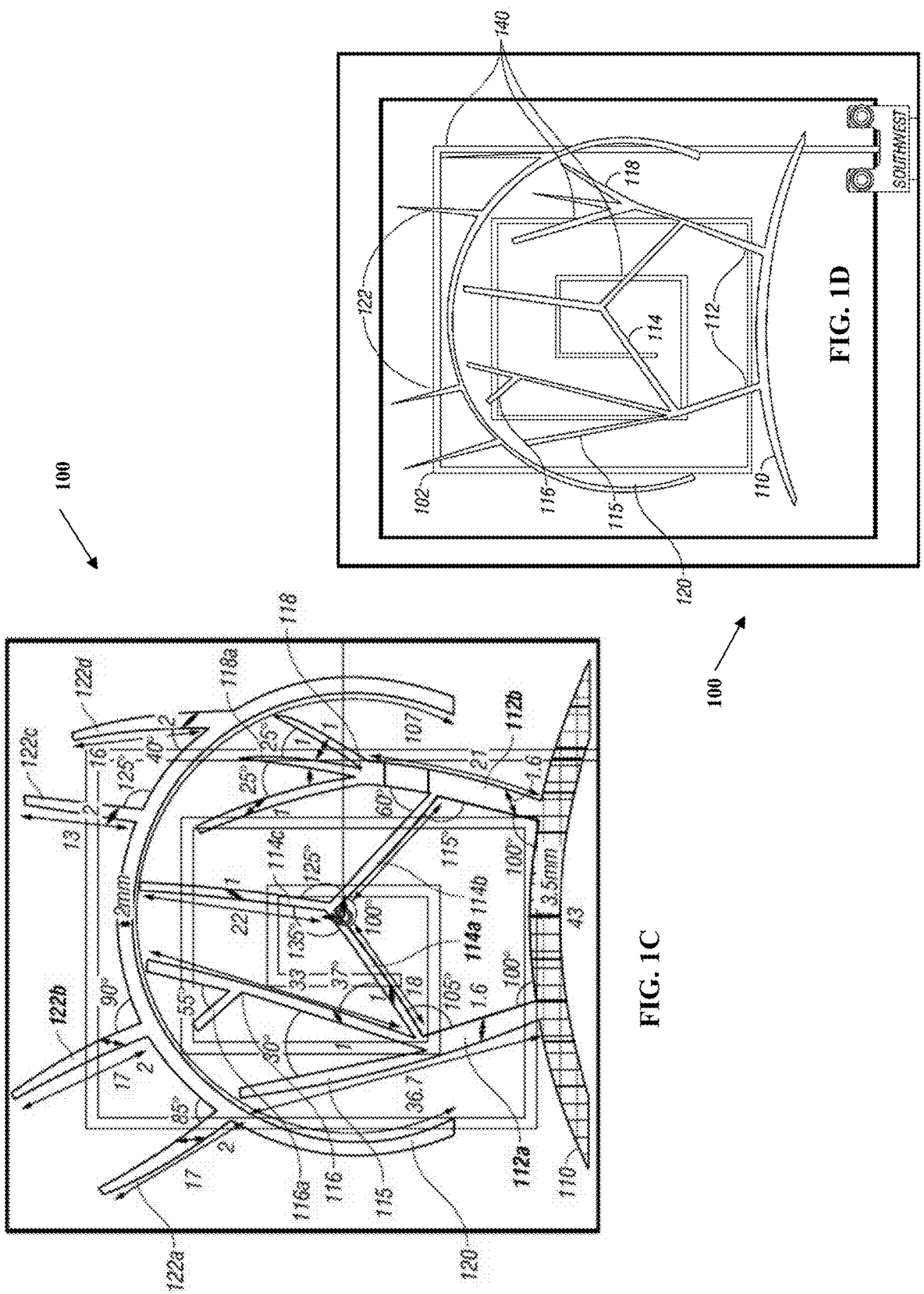
FIG. 1C is a schematic showing the slot geometries according to one embodiment.
FIG. 1D is a top view of the flexible antenna embodiment.

The foregoing and other features and advantages of the invention are apparent from the following detailed description of exemplary embodiments, read in conjunction with the accompanying drawings. The detailed description and drawings are merely illustrative of the invention rather than limiting, the scope of the invention being defined by the appended claims and equivalents thereof.

Embodiments of the invention will now be described with reference to the Figures, wherein like numerals reflect like elements throughout. The terminology used in the description presented herein is not intended to be interpreted in any limited or restrictive way, simply because it is being utilized in conjunction with detailed description of certain specific embodiments of the invention. Furthermore, embodiments of the invention may include several novel features, no single one of which is solely responsible for its desirable attributes or which is essential to practicing the invention described herein. The words proximal and distal are applied herein to denote specific ends of components of the instrument described herein. A proximal end refers to the end of an instrument nearer to an operator of the instrument when the instrument is being used. A distal end refers to the end of a component further from the operator and extending towards the monitored area of a patient's body.

The use of the terms "a" and "an" and "the" and similar referents in the context of describing the invention are to be construed to cover both the singular and the plural, unless otherwise indicated herein or clearly contradicted by context. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

Recitation of ranges of values herein are merely intended to serve as a shorthand method of referring individually to each separate value falling within the range, unless otherwise indicated herein, and each separate value is incorporated into the specification as if it were individually recited herein. The word "about," when accompanying a numerical value, is to be construed as indicating a deviation of up to and inclusive of 10% from the stated numerical value. The use of any and all examples, or exemplary language ("e.g." or "such as") provided herein, is intended merely to better illuminate the invention and does not pose a limitation on the scope of the invention unless otherwise claimed. No language in the specification should be construed as indicating any nonclaimed element as essential to the practice of the invention.

References to "one embodiment," "an embodiment," "example embodiment," "various embodiments," etc., may indicate that the embodiment(s) of the invention so described may include a particular feature, structure, or characteristic, but not every embodiment necessarily includes the particular feature, structure, or characteristic. Further, repeated use of the phrase "in one embodiment," or "in an exemplary embodiment," do not necessarily refer to the same embodiment, although they may.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical & medical arts.

The Antenna Design for Biomarker Monitoring measures biological and chemical markers and tracers in blood including glucose concentration without any extraction of blood. The Antenna Design for Biomarker Monitoring comprises a non-invasive method using Radio Frequency and Antenna Circuits and Systems. The Antenna Design for Biomarker Monitoring is a wearable device that can be a glove, semi-glove, or sock, or any similar wearable device that can non-invasively measure these blood physiological Biomarker, such as glucose levels in an instantaneous manner and continuous manner.

The device and design continuously measures biological, chemical markers and other tracers in the blood stream for physiological and pathophysiological screening in health and in disease in a non-invasive manner. Biomarkers can include novel/foreign/malignant or non-malignant cells or other newly developed molecules that may not be part of the typical constituents of the biological system. Biomarkers can also be traced not only in blood, but in the rest of the biological system, such as saliva, tissue, and the like.

Biomarkers as used herein is a broad term and is to be given its ordinary and customary meaning to a person of ordinary skill in the art (and is not to be limited to a special or customized meaning), and furthermore refers without limitation to a substance or chemical constituent in a biological fluid (for example, blood, interstitial fluid, cerebral spinal fluid, lymph fluid or urine) that can be analyzed. Biomarkers can include naturally occurring substances, artificial substances, metabolites, and/or reaction products. In some embodiments, the Biomarkers for measurement by the sensor heads, devices, and methods is a Biomarker. However, other Biomarkers are contemplated as well, including but not limited to acarboxyprothrombin; acylcarnitine; adenine phosphoribosyl transferase; adenosine deaminase; albumin; alpha-fetoprotein; amino acid profiles (arginine (Krebs cycle), histidine/urocanic acid, homocysteine, phenylalanine/tyrosine, tryptophan); andrenostenedione; antipyrine; arabinitol enantiomers; arginase; benzoylecgonine (cocaine); biotinidase; biopterin; c-reactive protein; carnitine; pro-BNP; BNP; troponin; carnosinase; CD4; ceruloplasmin; chenodeoxycholic acid; chloroquine; cholesterol; cholinesterase; conjugated 1-β hydroxy-cholic acid; cortisol; creatine kinase; creatine kinase MM isoenzyme; cyclosporin A; d-penicillamine; de-ethylchloroquine; dehydroepiandrosterone sulfate; DNA (acetylator polymorphism, alcohol dehydrogenase, alpha 1-antitrypsin, cystic fibrosis, Duchenne/Becker muscular dystrophy, analyte-6-phosphate dehydrogenase, hemoglobin A, hemoglobin S, hemoglobin C, hemoglobin D, hemoglobin E, hemoglobin F, D-Punjab, beta-thalassemia, hepatitis B virus, HCMV, HIV-1, HTLV-1, Leber hereditary optic neuropathy, MCAD, RNA, PKU, *Plasmodium* vivax, sexual differentiation, 21-deoxycortisol); desbutylhalofantrine; dihydropteridine reductase; diptheria/tetanus antitoxin; erythrocyte arginase; erythrocyte protoporphyrin; esterase D; fatty acids/acylglycines; free β-human chorionic gonadotropin; free erythrocyte porphyrin; free thyroxine (FT4); free tri-iodothyronine (FT3); fumarylacetoacetase; galactose/gal-1-phosphate; galactose-1-phosphate uridyltransferase; gentamicin; analyte-6-phosphate dehydrogenase; glutathione; glutathione perioxidase; glycocholic acid; glycosylated hemoglobin; halofantrine; hemoglobin variants; hexosaminidase A; human erythrocyte carbonic anhydrase I; 17-alpha-hydroxyprogesterone; hypoxanthine phosphoribosyl transferase; immunoreactive trypsin; lactate; lead; lipoproteins ((a), B/A-1, β); lysozyme; mefloquine; netilmicin; phenobarbitone; phenytoin; phytanic/pristanic acid; progesterone; prolactin; prolidase; purine nucleoside phosphorylase; quinine; reverse tri-iodothyronine (rT3); selenium; serum pancreatic lipase; sissomicin; somatomedin C; specific antibodies (adenovirus, anti-nuclear antibody, anti-zeta antibody, arbovirus, Aujeszky's disease virus, dengue virus, *Dracunculus medinensis, Echinococcus granulosus, Entamoeba histolytica*, enterovirus, *Giardia duodenalisa, Helicobacter pylori*, hepatitis B virus, herpes virus, HIV-1, IgE (atopic disease), influenza virus, *Leishmania donovani*, leptospira, measles/mumps/rubella, *Mycobacterium leprae, Mycoplasma pneumoniae*, Myoglobin, *Onchocerca volvulus*, parainfluenza virus, *Plasmodium falciparum*, poliovirus, *Pseudomonas aeruginosa*, respiratory syncytial virus, *rickettsia* (scrub typhus), *Schistosoma mansoni, Toxoplasma gondii, Trepenoma pallidium, Trypanosoma cruzi/rangeli*, vesicular stomatis virus, *Wuchereria bancrofti*, yellow fever virus); specific antigens (hepatitis B virus, HIV-1); succinylacetone; sulfadoxine; theophylline; thyrotropin (TSH); thyroxine (T4); thyroxine-binding globulin; trace elements; transferrin; UDP-galactose-4-epimerase; urea; uroporphyrinogen I synthase; vitamin A; white blood cells; and zinc protoporphyrin. Salts, sugar, protein, fat, vitamins, and hormones naturally occurring in blood or interstitial fluids can also constitute Biomarkers in certain embodiments. The Biomarkers can be naturally present in the biological fluid, for example, a metabolic product, a hormone, an antigen, an antibody, and the like. Alternatively, the Biomarkers can be introduced into the body, for example, a contrast agent for imaging, a radioisotope, a chemical agent, a fluorocarbon-based synthetic blood, or a drug or pharmaceutical composition, including but not limited to insulin; ethanol; *cannabis* (marijuana, tetrahydrocannabinol, hashish); inhalants (nitrous oxide, amyl nitrite, butyl nitrite, chlorohydrocarbons, hydrocarbons); cocaine (crack cocaine); stimulants (amphetamines, methamphetamines, Ritalin, Cylert, Preludin, Didrex, PreState, Voranil, Sandrex, Plegine); depressants (barbituates, methaqualone, tranquilizers such as Valium, Librium, Miltown, Serax, Equanil, Tranxene); hallucinogens (phencyclidine, lysergic acid, mescaline, peyote, psilocybin); narcotics (heroin, codeine, morphine, opium, meperidine, Percocet, Percodan, Tussionex, Fentanyl, Darvon, Talwin, Lomotil); designer drugs (analogs of fentanyl, meperidine, amphetamines, methamphetamines, and phencyclidine, for example, Ecstasy); anabolic steroids; and nicotine. The metabolic products of drugs and pharmaceutical compositions are also contemplated Biomarkers. Biomarkers such as neurochemicals and other chemicals generated within the body can also be analyzed, such as, for example, ascorbic acid, uric acid, dopamine, noradrenaline, 3-methoxytyramine (3MT), 3,4-Dihydroxyphenylacetic acid (DOPAC), Homovanillic acid (HVA), 5-Hydroxytryptamine (5HT), and 5-Hydroxyindoleacetic acid (FHIAA).

An example of pathophysiological alteration leading to diseases include, but are not limited to, hyperglycemia/diabetes, cholesterolemia, heart disease Biomarkers as well as other biological alterations that involve measuring variations of glucose level, cholesterol levels, Pro-BNP (pro-Brain Natriuretic peptide) and troponin levels, and other molecular Biomarkers in living tissue. For example in diabetes, the proposed prototype is envisioned to help monitor instantaneous glucose levels to be used: to determine the alteration in glycemia and variations from norm; and for autonomous interventions such as insulin injections; and to offer diabetic patients an improved and self-constrained control of the disease. Thus, along with an estimate of the bulk concentration, the device monitors the rate of change of concentrations to predict possible hyperglycemia and hypoglycemia early.

Figure 2A:
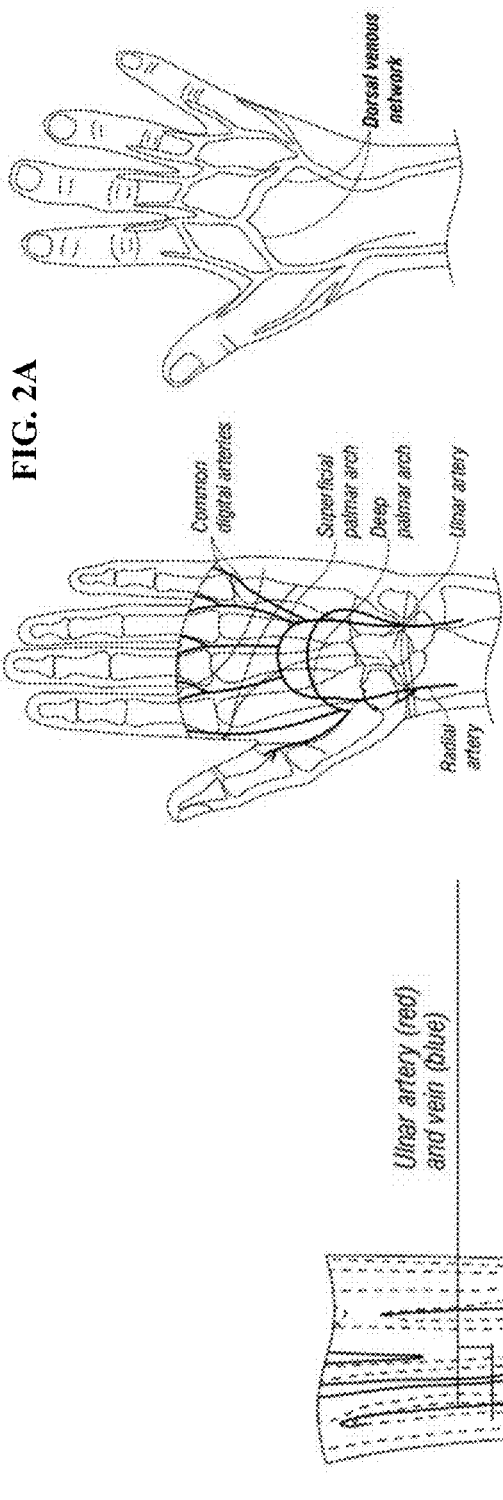
FIG. 2A is an image of the distribution of the arteries and veins in the hand.

The Antenna Design for Biomarker Monitoring comprises a sensor 100, as shown in FIG. 1A-1B composed of an antenna including a plurality of slots 102 corresponding to the arteries and veins of a human hand to non-invasively detect the concentration of blood constituents in human blood stream continuously through electromagnetic wave radiation, according to one embodiment. In other embodiment, the antenna design may include a plurality of slots corresponding to arteries and veins in other anatomical structures, such as the foot, arm, leg, neck, and the like. The correspondence between the slots and underlying vein structures allows to the antenna to focus/strengthen the sensing mechanism to a plurality of key blood vessels structures while minimizing the direct interaction with noncritical areas. Hence, the sensitivity of the sensor to blood glucose variations in the underlying vessels is increased. The sensor 100 comprises a first slotted arch 110 and a second slotted arch 120. The first slotted arch 110 and the second slotted arch 120 are not directly connected through slots 102. The first slotted arch 120 corresponds to the shape of the deep palmar arch, and the second slotted arch 120 corresponds to the shape of superficial palmar arch. The first slotted arch 110 includes at least two slotted main branches 112 that are connected by a λ-slotted branch 114. One slotted main branch 112 includes a single slot branch 115 and a Y-shaped branch 116 and another slotted main branch 112 includes a W-shaped branch 118, all of which corresponds to the dorsal metacarpal veins or the palmar digital arteries, as shown in FIGS. 2A-2B. The second slotted arch 120 includes at least four single slots 122 that correspond to the palmar digital arteries. In one embodiment, the antenna is used to transmit electromagnetic waves into human tissues in areas in close proximity to the main palmar veins in order to better monitor and detect the variation of the concentration of the blood constituent compared to other embodiments that do not track the vein structure. FIG. 1B is referred to as the Rigid Antenna below.

According to some embodiments, the slots may include a range of geometries, angles, and lengths for all the different branches. A range of the widths of the slots, and spacing between the slots, may be provided if slot/design modification is required. The stretching involves stretching the spaces between two slots and/or angle between two slots as well to better overlap the slots and targeted underlying vein. The specific desired ranges for the slots/spacings will be divided into groups. Otherwise, the variation in the design upon stretching would be large if it were to cover all desired ranges. The slot designs may be grouped into several size categories such as extra small, small, large, and extra-large, depending the size of the target underlying anatomy. Flexibility in one embodiment allows for matching in between the standard sizes. Flexibility in another embodiment allows for matching based on visual and measurement calibrations. In one embodiment, the design may be customized and stretchable for children, where the stretching enhances the coverage of the veins. Flexibility then allows in this embodiment stretching the product as the child grows over a period of several month.

Figure 2C:
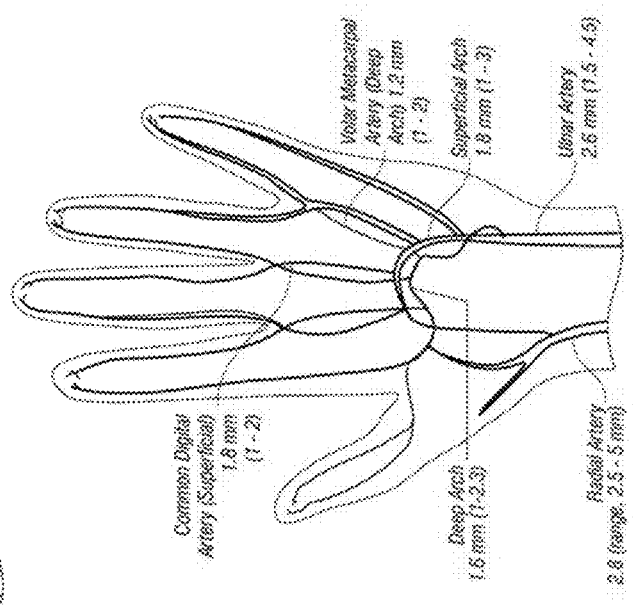
FIG. 2C is a schematic showing the geometry of the Arterial Patterns of the Deep and Superficial Palmar Arches.
Figure 2B:
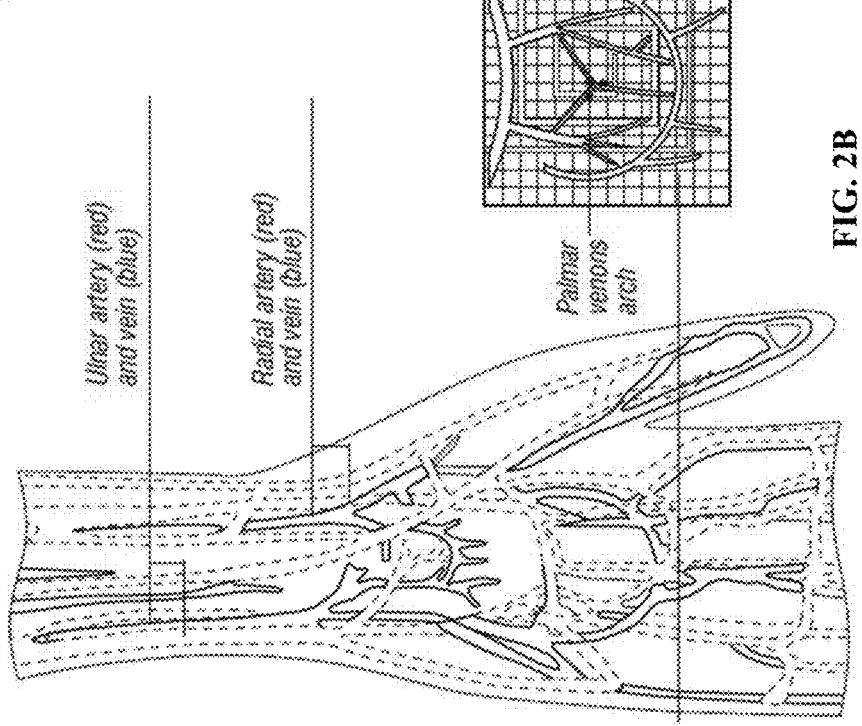
FIG. 2B is an image of the design in FIG. 1A overlayed over the hand.

The palmar digital arteries include Arterial Patterns of the Deep and Superficial Palmar Arches, as shown in FIG. 2C. The slots diameter may correspond to the diameters of the respective deep and superficial palmar arches. The radial artery includes a diameter of range of about 2.3 mm to about 5.0 mm. The ulnar artery includes a diameter range of about 1.4 mm to about 4.5 mm. The superficial arch includes a diameter range of about 1.0 mm to about 3.0 mm. The deep arch includes a diameter range of about 1.0 mm to about 2.3 mm. The common volar digital arteries (superficial arch) includes a diameter range of about 1.0 mm to about 2.0 mm. The common metacarpal arteries (deep arch) includes a range of about 1.0 mm to about 2.0 mm.

In one embodiment, the range of the slot width is obtained from the corresponding artery diameter and is in range of about 1.2 mm to about 2 mm for proper coverage of the veins. For the fabricated antenna arcs as illustrated in FIG. 1C, the dimensions are for a measurement of a typical small size adult female. In this embodiment, the sensor 100 comprises a first slotted arch 110 with a diameter or width about 3.5 mm and an arched length of about 43 mm. The second slotted arch 120 includes a diameter of about 2 mm, an inner arched length of about 107 mm, and an angle of curvature at about 55 degrees. The first slotted main branch 112a includes a slot width of about 1.6 mm and a length of about 36.7 mm and is set at angle of about 100 degree with respect to the first slotted arch 110. The second slotted main branch 112b includes a slot width of about 1.6 mm, a length of about 21 mm, and is set at an angle of about 100 degrees with respect to the first slotted arch 110. The λ-slotted branch 114 includes a first leg 114a with slot width of about 1 mm, a slot length of about 18 mm, and an angle of about 105 degrees with respect to the first slotted main branch 112a. The λ-slotted branch 114 includes a second leg 114b with slot width of about 1 mm, a slot length of about 18 mm, an angle of about 115 degrees with respect to the second slotted main branch 112b, and an angel of about 100 degrees with respect to the first leg 114a. The λ-slotted branch 114 includes a third leg 114c with a slot width of about 1 mm, a slot length of about 22 mm, and an angle of 135 degrees with respect to the first leg 114a, an angle of 125 degrees with respect to the second leg 114b. The first slotted main branch 112a includes a single slot branch 115 with a slot width of about 1 mm and an angle of about 30 degrees with respect to the Y-shaped branch 116. The Y-shaped branch 116 includes a slot width of about 1 mm, a slot length of about 33 mm, and an angle of about 37 degrees with respect to the first leg 114a. The Y-shaped branch 116 includes a Y-shape with an angle of about 55 degrees with respect to the Y-shape legs 116a. The second slotted main branch 112b includes a W-shaped branch 118 with a slot width of about 1 mm and an angle of about 25 degrees with respect to the W-shaped legs 118a. The second slotted arch 120 includes a first single slot 122a with a slot width of about 2 mm, slot length of about 17 mm, and an angle of about 85 degrees with respect to the second slotted arch 120. The second slotted arch 120 includes a second single slot 122b with a slot width of about 2 mm, slot length of about 17 mm, and an angle of about 90 degrees with respect to the second slotted arch 120. The second slotted arch 120 includes a third single slot 122c with a slot width of about 2 mm, slot length of about 13 mm, and an angle of about 125 degrees with respect to the second slotted arch 120. The second slotted arch 120 includes a fourth single slot 122d with a slot width of about 2 mm, slot length of about 16 mm, and an angle of about 40 degrees with respect to the second slotted arch 120. Further modifications can be obtained from human measurements to define standard sizes.

Figure 3D:
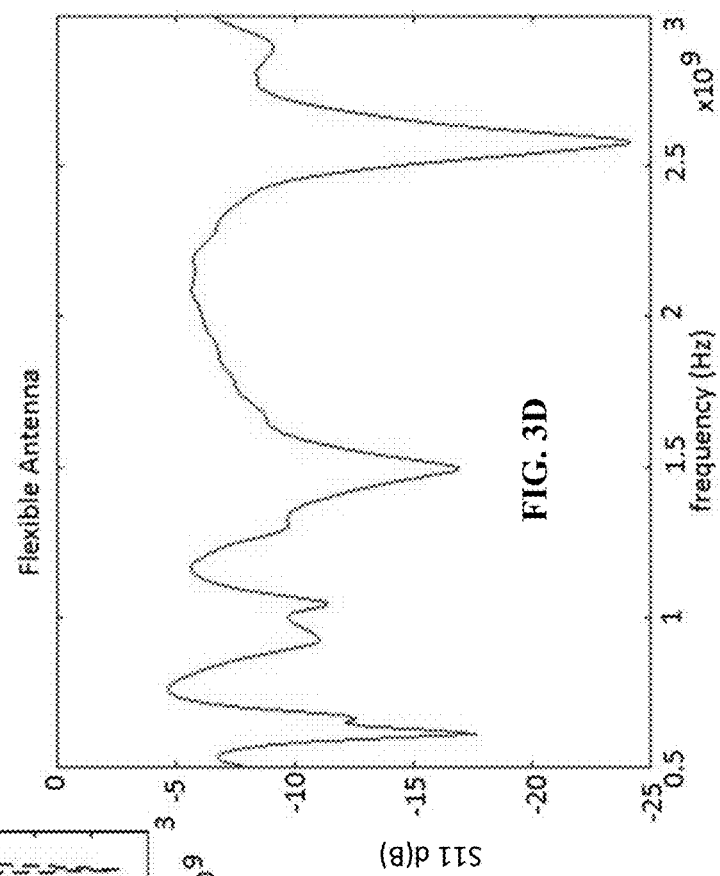
FIG. 3D is a graph of the Measured S11 in free Space of the flexible antenna embodiment.
Figure 3C:
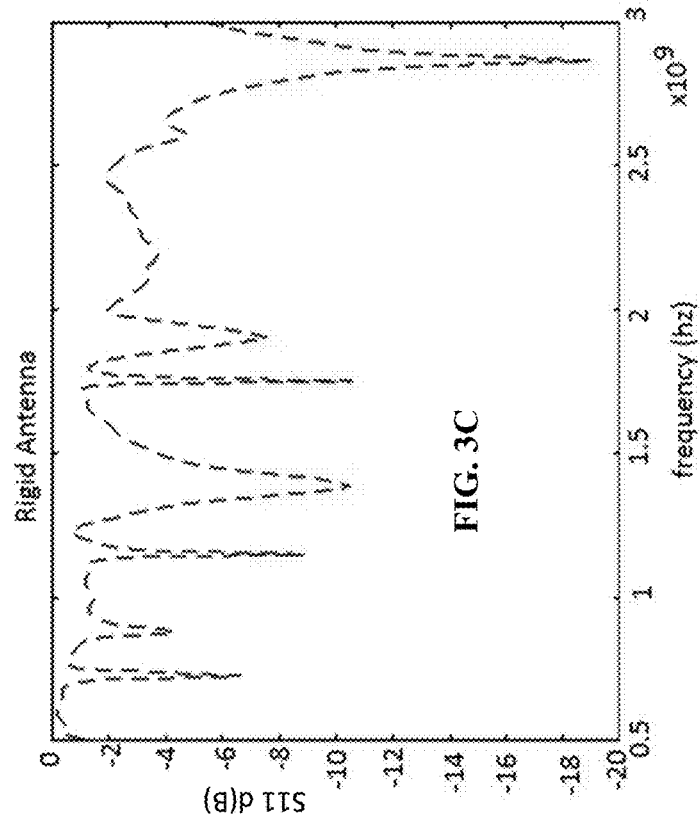
FIG. 3C is a graph of the Measured S11 in free Space of the rigid antenna embodiment.

In one embodiment, the antenna is a micro-strip antenna comprised of a web of slots that represent the human hand veins. The antenna is designed using a flexible dielectric substrate to be placed easily into a glove. In another embodiment, the antenna slots can be designed after the foot veins, and can be built on a flexible substrate to fit into a sock. As shown in FIGS. 1A-1C, the antenna comprises a spirally shaped feeding transmission line 140 with three turns 142 in a spiral configuration that are positioned on the bottom layer 130 of the antenna such that the transmission line is separated from the sensing surface. The spirally shaped feeding line 140 enhances the coupling between the feedlines and the slots on the top layer of the antenna. The antenna resonates when it is loaded with a typical human hand tissue to increase its sensitivity to the variation of the blood constituents. The human hand tissue comprises a skin layer, fat layer, blood layer, muscle layer and bone layer. The antenna is operational at multiple frequencies within the microwave region. Specifically, the antenna is designed to operate in the UHF, L-bands and lower S-bands ranging between about 500 MHz and about 3 GHz, as shown in FIGS. 3A-3B. The measured S11 in free space for the rigid antennae is shown in FIG. 3C. And the measured S11 in free space for the flexible antennae is shown in FIG. 3D. FIG. 1D is a top view of the flexible antenna embodiment.

In one embodiment, the antenna is designed to be multiband, where each component of the antenna is designed after pulmar venous and dorsal venous archs. The spiral feeding line allows different slots to be active and hence also enhances the multi-band behavior of the antenna. The antenna in another embodiment is designed to be reconfigurable to cover multiple frequencies within the frequency band ranging from about 500 MHz and about 3 GHz. The reconfiguration of the antenna is restrained to its frequency of operation by resorting to various reconfiguration components such as pin diodes, RF MEMs, varactors, and/or digitally tunable capacitors. The reconfiguring component will be positioned in strategic locations along the slots or the feeding line of the antenna. In another embodiment, mechanical reconfiguration techniques can also be used to reconfigure the frequency of operation of the antenna. Such techniques include actuators, piezo-electric transducers, and others in order to change the separation between the ground planes and the slots or to change the lengths of the slot web or feeding lines through stretching of the material composing the antenna as well as other means.

In other embodiments, the design can be adjusted to fit the physiology of multiple users by relying by relying on stretchable antenna material. For one embodiment, a glove along with embedded stretchable antenna can stretch to fit the topology of the pulmar veins of the specific user. In addition, the glove can be equipped with electro-mechanical peripheral circuitry to assist with the stretching or bending of the antenna topology to match the human anatomy. The fitting stretching can be assisted by human eye, medical expert, or automatically via feedback from vein detection circuitry. The vein detection will be based on optical sensors, the vein images will be processed and the electromechanical circuitry will automatically adjust the stretchable antenna to match the underlying image.

In one embodiment, the stretchable antenna material similar to [1] TY—JOURAU—Chen, ZhiboAU—Xi, JingtianAU—Huang, WeiAU—Yuen, Matthew M. F. PY—2017DA—2017/09/08TI—Stretchable conductive elastomer for wireless wearable communication applications JO—Scientific Reports SP—10958VL—71S—1AB] can be used in one embodiment.

The above embodiments tune the design for random customers and hence fit the design better to different population groups. Variation of material upon stretching may be analyzed and expanded.

In one embodiment, the stretching is limited to be 10% over the width and length of the slot, since there is an effect of stretching both dielectric and conductive material on the efficiency, resonant frequency and matching of the device. As such, no more than 10% of stretching over the width or length of the slot is allowed. Based on TY—JOURAU—Chen, ZhiboAU—Xi, JingtianAU—Huang, WeiAU—Yuen, Matthew M. F. PY—2017DA—2017/09/08TI—Stretchable conductive elastomer for wireless wearable communication applications JO—Scientific Reports SP—10958VL—71S—1AB, the radiation efficiency around the initial resonance frequency shifts monotonically as the stretching percentage increases. With the increasing strain, the resonance frequency shifts to a lower frequency due to the increased effective electrical length. The Ag-PDMS conductor can be considered as hyperelastic material; therefore, when the antenna is elongated in the length direction, the width and height shrink proportionally to keep the total volume constant during deformation, resulting in reduced impedance match and hence lower radiation efficiency.

The design tolerance to stretching can be altered in some embodiments, as follows: (a) Tolerating impedance match reduction: this can be tolerated as long as the stretched antenna maintains resonance levels are maintained moderately below −10 db. Hence, the design is configured to maintain resonance levels below −10 db under maximum stretching conditions (b) Tolerating Lower radiation efficiency upon stretching: this can be tolerated to a certain extent, and can be resolved by increasing the input power. (c) Tolerating changed response of the stretched design: This does not have implications on the sensitivity measurements, or glucose level tracking, since the stretched design will be used to measure the reference glucose level and the variations. The model will be developed independently for the stretched design.

Figure 4A:
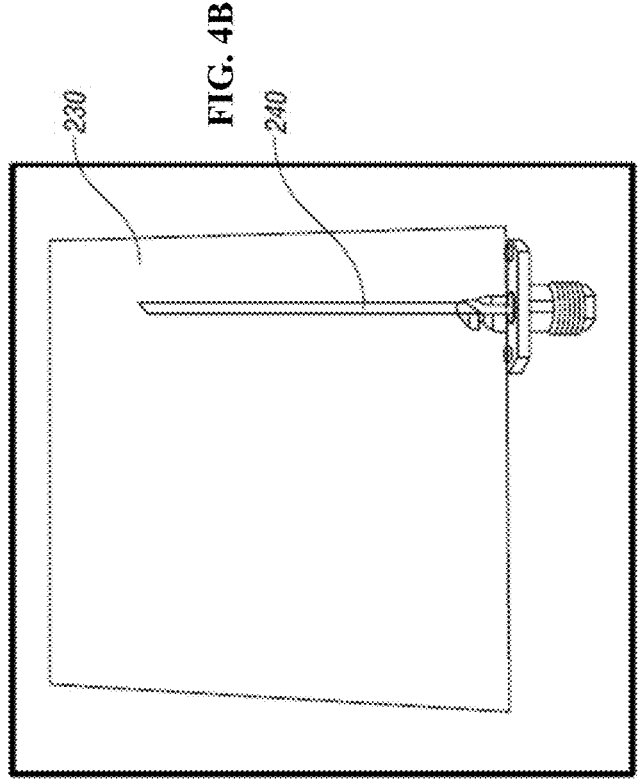
FIG. 4A is a top view of another embodiment with a modified structure.
Figure 4B:
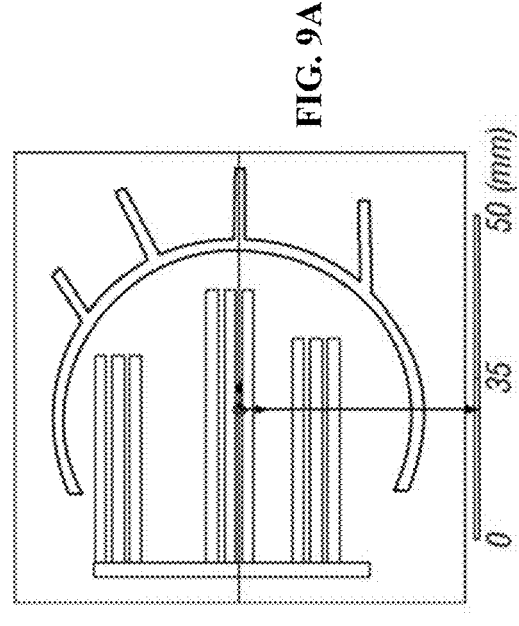
FIG. 4B is the back of another embodiment with a modified structure.
Figure 5A:
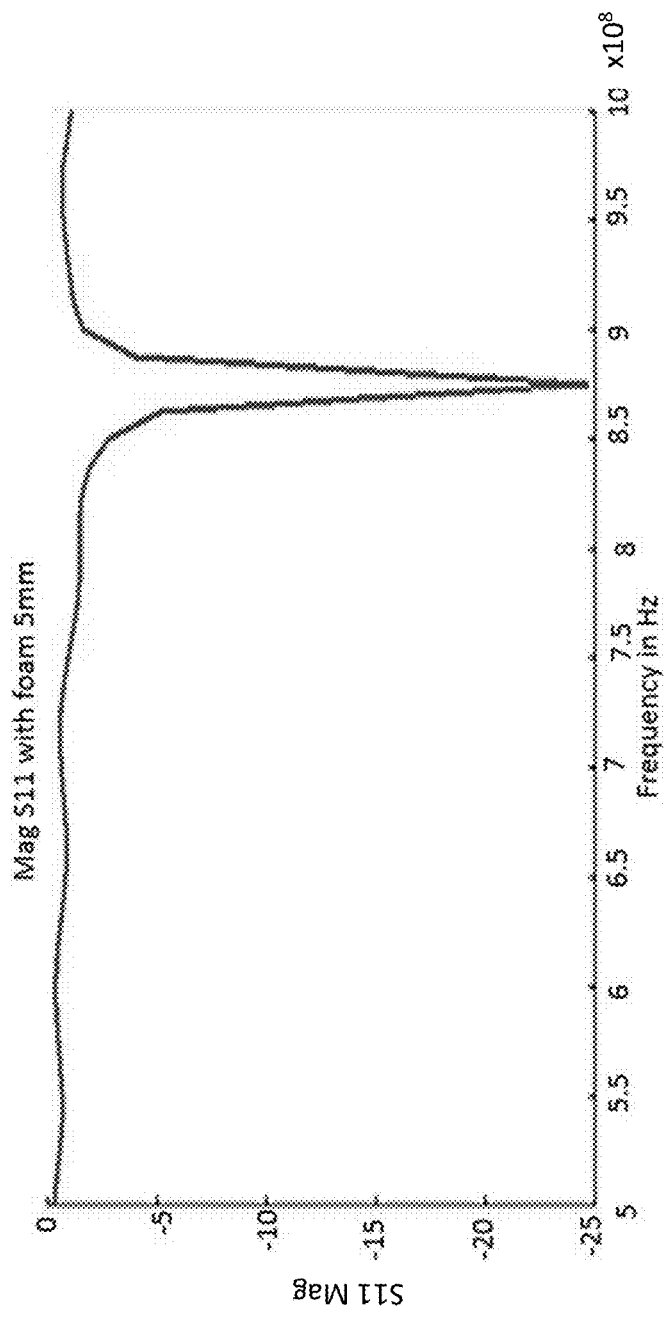
FIG. 5A is a graph of the measured S11 Mag with foam 5 mm and FIG. 5B is a graph of S11 Phase of the sensor embodiment with foam 5 mm.
Figure 5B:
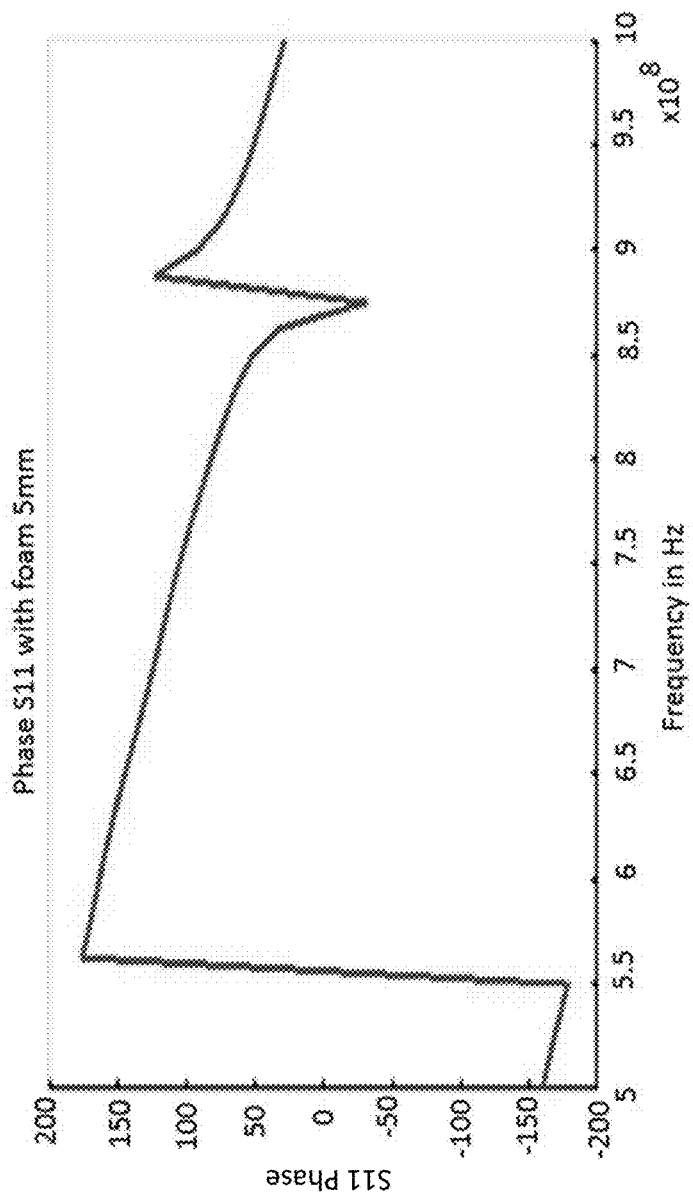

In another embodiment, as shown in FIG. 4A, an antenna including a plurality of slots 202 corresponding to the arteries and veins of a human hand to non-invasively detect the concentration of blood constituents in human blood stream continuously through electromagnetic wave radiation, according to one embodiment. The sensor 200 comprises a first slotted base 210 and a second slotted arch 220. The first slotted base 210 and the second slotted arch 220 are not directly connected through slots 202. The first slotted base 210 corresponds to the deep palmar arch, and the second slotted arch 220 corresponds to the shape of superficial palmar arch. The first slotted base 210 includes a first triple slot 212, a second triple slot 214, and a third triple slot 216. The second slotted arch 220 includes at least four single slots 222. As shown in FIG. 4B, the antenna comprises a single feeding transmission line 240 on the back of the flexible dielectric substrate 230. The measured S11 magnitude and the S11 phase of the sensor 200 are shown in FIGS. 5A and 5B.

Figure 6A:
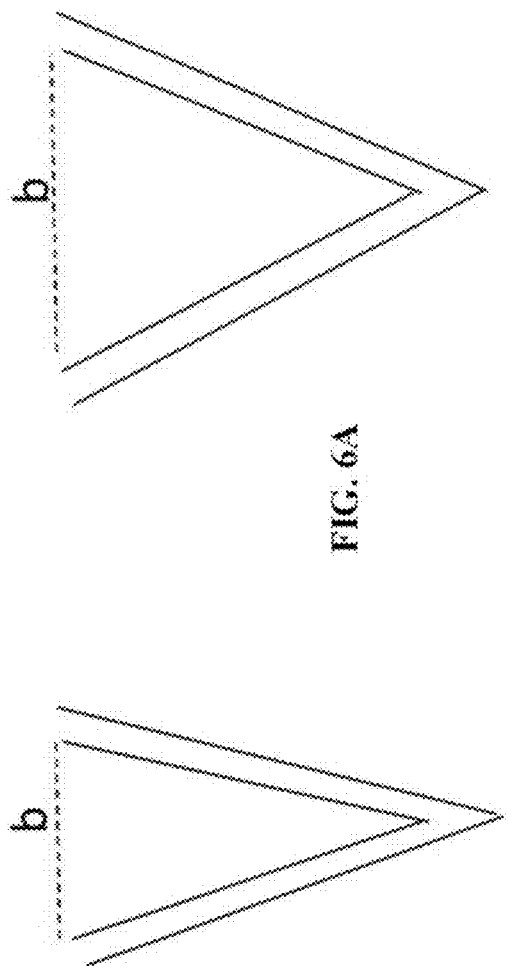
FIG. 6A is schematic diagram where blue lines will constitute microfluidic channels that will be filled with the same volume of liquid metal to enable a possible embodiment of reconfigurable antenna. The angle is adjusted to match the patient vein topology.
Figure 6B:
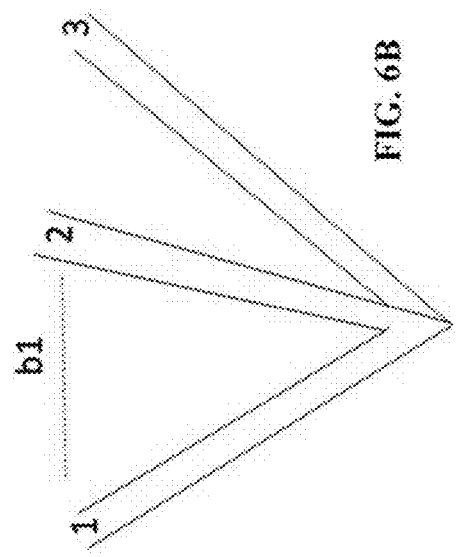
FIG. 6B is schematic diagram showing the reconfigured the antenna design for best topology matching.

As shown in FIG. 6A, in a third embodiment, microfluidic channels separated by distance b can be used to allow liquid metal to be rerouted in order to reconfigure the antenna performance. This helps to adapt the antenna shape to the change in the topology of the design to match the underlying vein topology for the different users. FIG. 6A shows an example where blue lines will constitute microfluidic channels that will be filled with liquid metal to enable a possible embodiment of reconfigurable antenna. The angle is adjusted to match the patient vein topology. Hence, both the angle (substrate material stretching) and rerouting can be used to reconfigure the antenna design for best topology matching as illustrated in the FIG. 6B.

For all, the above embodiments, when the design topology changes or upon reconfiguration, the antenna performance changes; however, an attached circuit to the device can detect the response at a sweep of different frequency over the pre-defined range of Operation based on the expected stretching distance. The response at the different frequency ranges will then be used to develop a model to predict glucose levels.

The signal measured from the antenna is converted using a computer program that allows the transformation of the magnitude and the phase of the reflected and/or transmitted signals into concentration of the blood constituents via trained models.

The non-invasive electromagnetic sensor 200 detects the concentration of some blood constituents in human blood stream continuously. The sensor 200 transmits electromagnetic waves into human tissues in order to monitor and detect the variation of the concentration of the blood constituent. The sensor device to convert the detected energy into magnitude and phase.

The sensor device 200 processes the detected magnitude and phase and convert it into concentration. The sensor comprises a slot antenna, as shown in FIGS. 4A-4B. The sensor 200 is operational at multiple frequencies within the frequency band ranging between about 500 MHz and about 1 GHz, as shown in FIG. 5A. The sensor includes the transmission line that is separated from the sensing surface. The sensor is reconfigurable to cover more frequencies within the frequency band ranging from about 500 MHz and about 1 GHz. The sensor includes slots that correspond to the arteries and veins in the human hand, in one embodiment. The sensor includes slots that correspond to the shape of the deep palmar arch, the superficial palmar arch, the palmar digital arteries and the dorsal metacarpal veins. The sensor is designed on dielectric substrate, in one embodiment. The sensor of designed using a flexible substrate to be placed easily into a glove, according to one embodiment. The sensor is connected to a network analyzer to convert the detected energy into magnitude and phase. The sensor is connected to a signal processing system to convert the magnitude and/or the phase into concentration of the blood constituents.

Figure 7A:
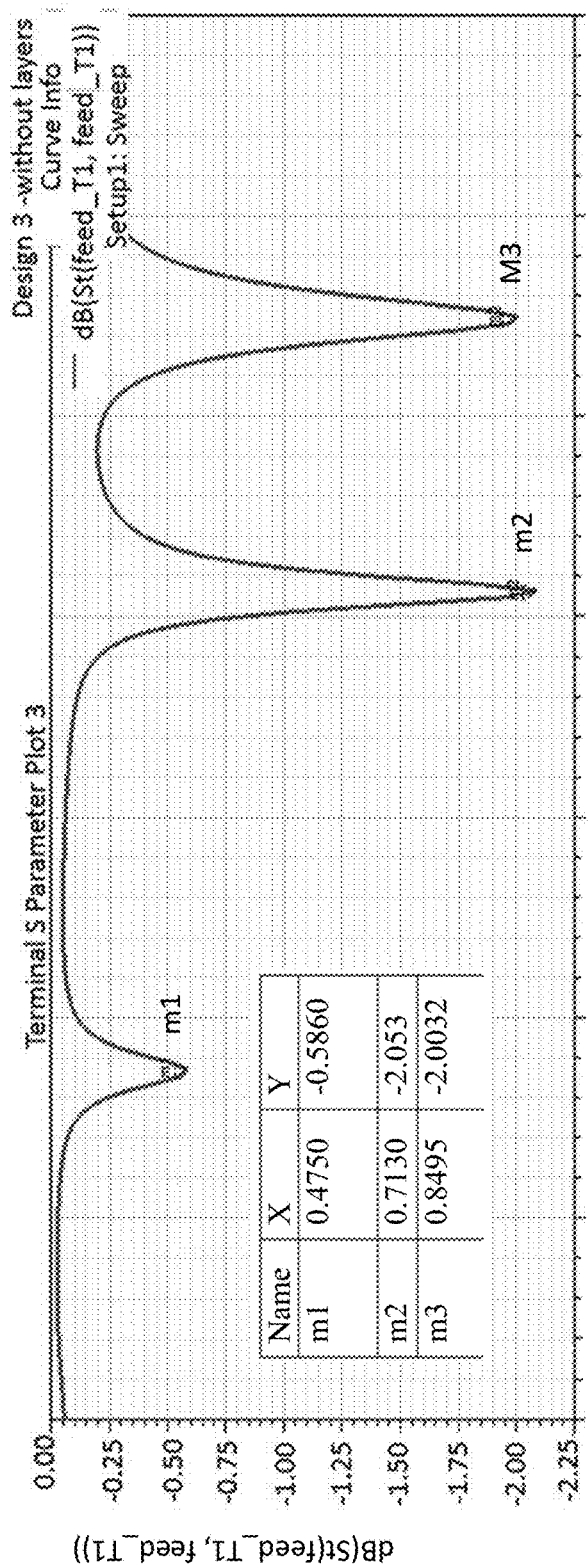
FIG. 7A is a graph showing a loaded with the hand its S11 drops below −10 dB.
Figure 7B:
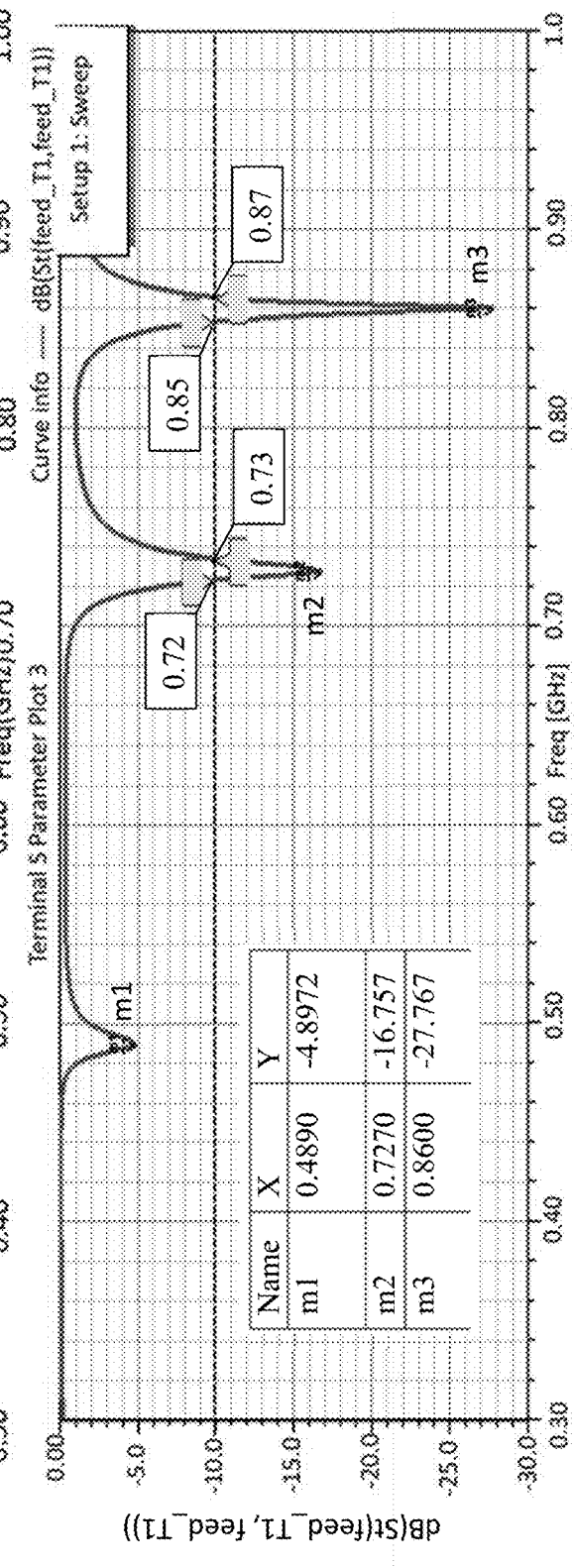
FIG. 7B is a graph showing S11 of the antenna with the loaded human hand.

As shown in FIGS. 7A-7B, this antenna is designed to be operational when loaded with a human hand model. This will make it more sensitive to the variation of the blood constituents levels. The human hand model is composed of 5 layers: a skin layer, fat layer, blood layer, muscle layer and bone layer. Here, the design is to adapt to the topology of the critical area/organ to enhance its sensitivity. The shape of this antenna corresponds to the hand's veins and arteries. The shape of this antenna corresponds to the shape of the deep palmar arch, the superficial palmar arch, the palmar digital arteries and the dorsal metacarpal veins. This distribution increases the sensitivity of the antenna to the variation of the blood constituents levels flowing in the hand's veins and arteries. The multiple slots make this antenna operational at multiple frequencies within the UHF frequency and microwave bands ranging between about 500 MHz and about 3 GHz, which provides a practical window to detect the variation of the blood glucose level at different frequencies for different patients.

Figure 8A:
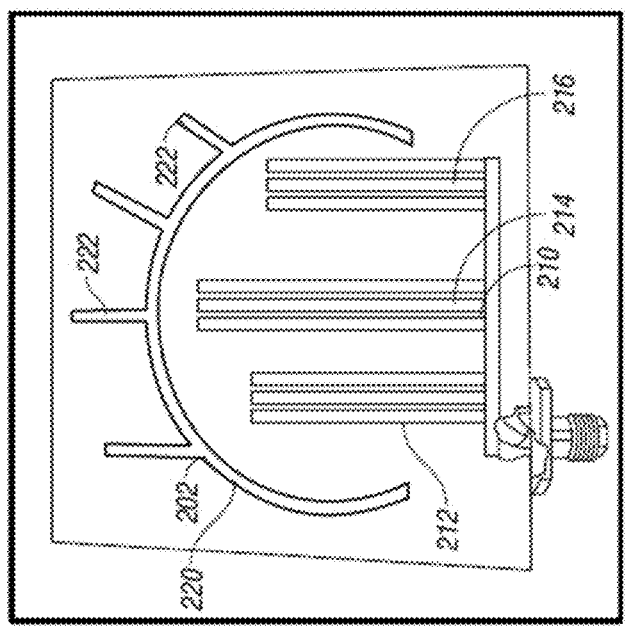
FIG. 8A is a schematic of a V-shape slot antenna.
Figure 9A:
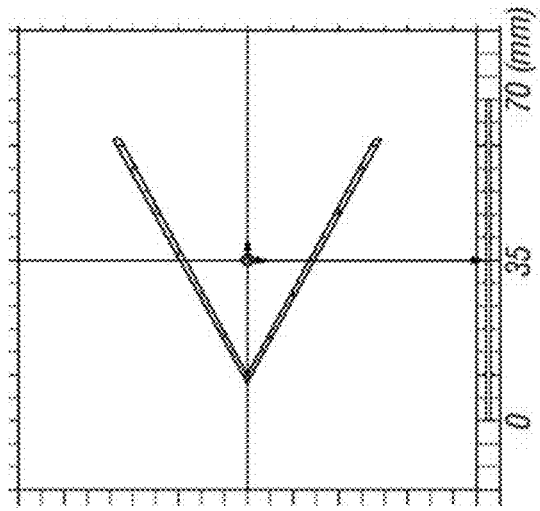
FIG. 9A is a schematic of the vein model antenna.
Figure 8B:
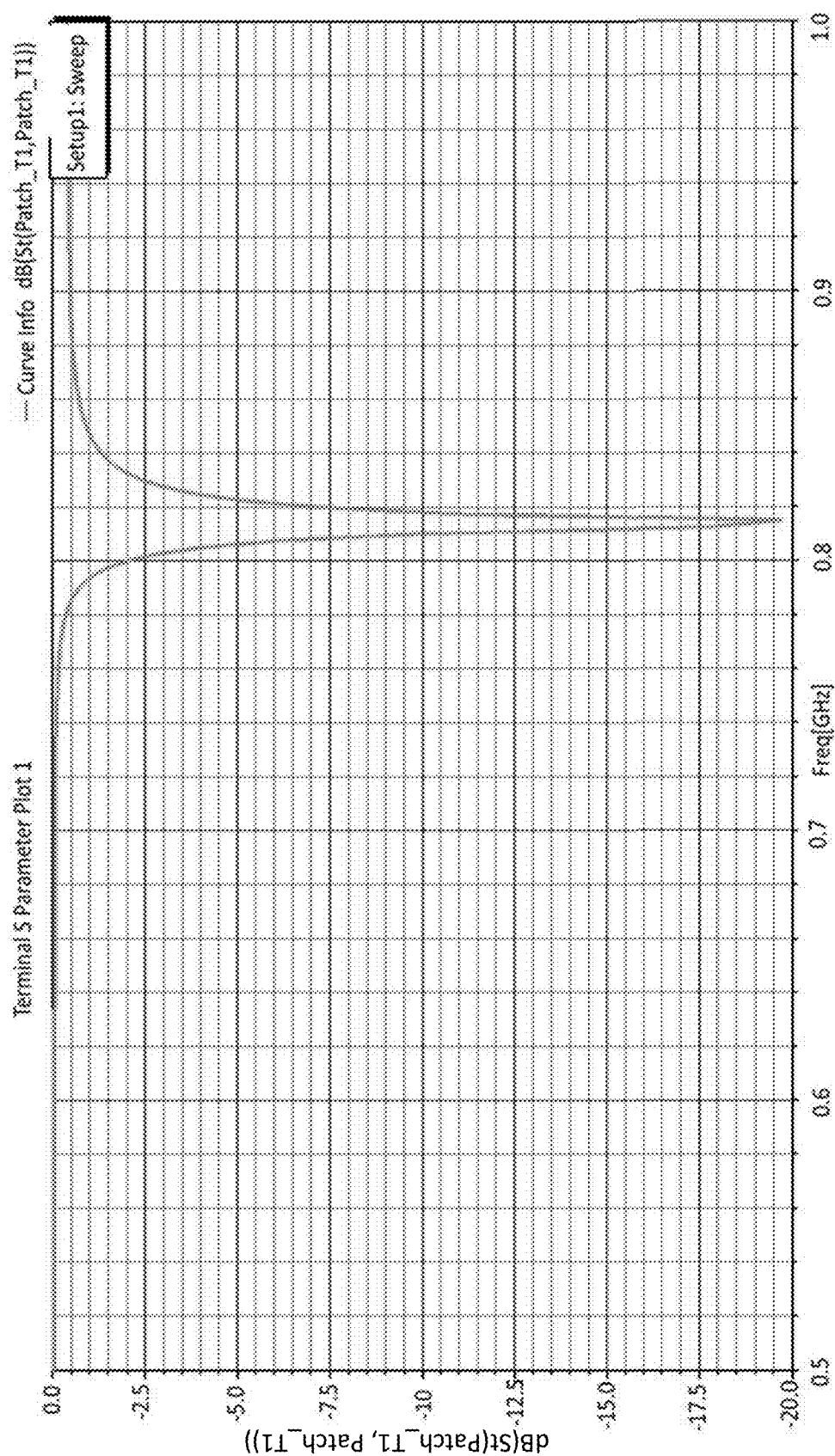
FIG. 8B is a graph of the terminal S parameter plot of the V-shape slot antenna.
Figure 9B:
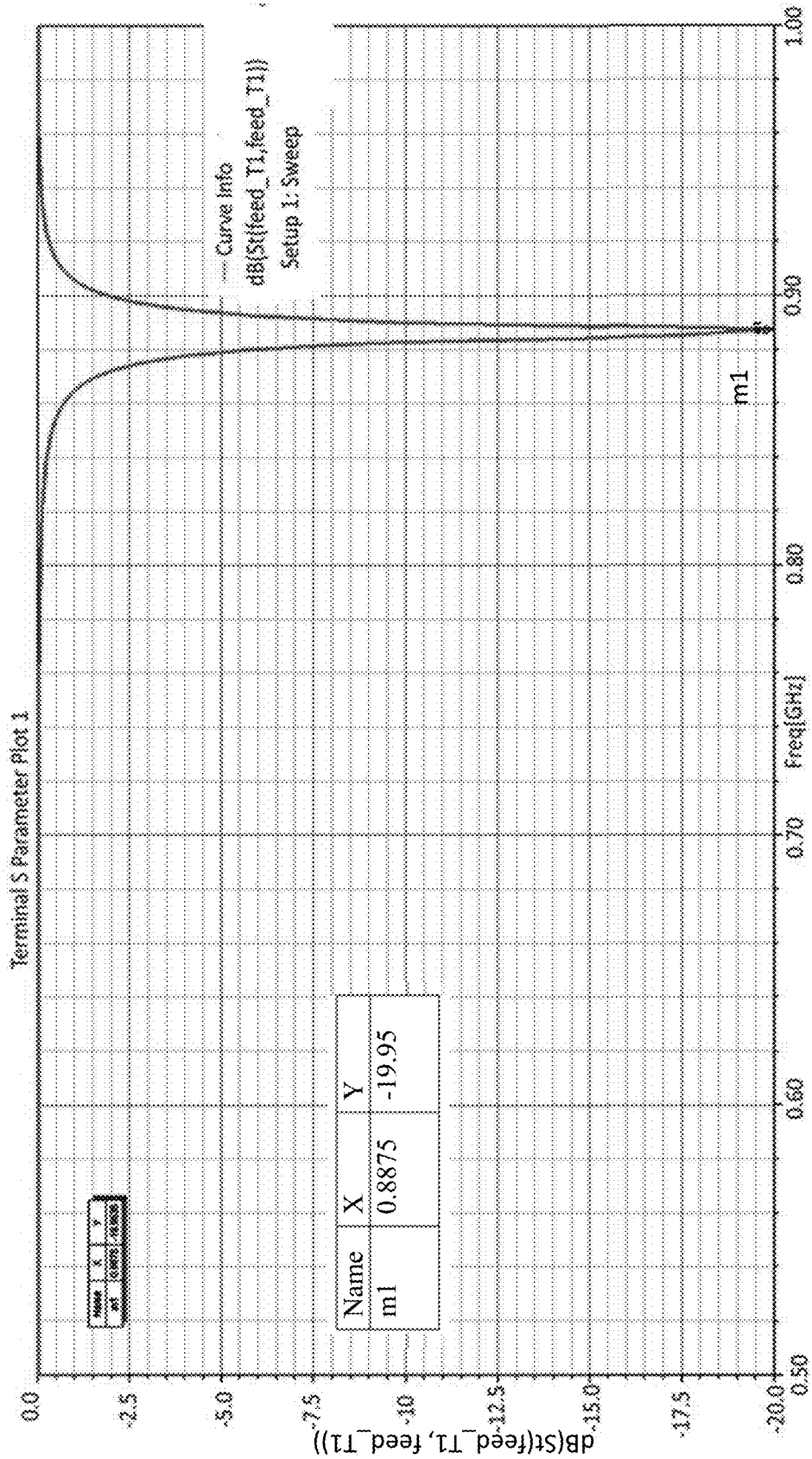
FIG. 9B is a graph of the terminal S parameter plot of the vein model antenna.

Sensitivity of the Specialized Antenna Versus a Generic Antenna:

To prove that the shape of this antenna increases the sensitivity of the system, the response of two antennas is compared (a random V-shape slot antenna that does not match the pattern of the underlying veins, as shown in FIG. 8A and the vein-shape slot antenna 200 as shown in FIG. 9A) loaded with a vein model using HFSS. The permittivity of the vein-model slot antenna 200 was varied between about 60 and about 80 (which is in the range needed for blood glucose estimation). The shift in frequency of both antennas was monitored, as shown in FIGS. 8B and 9B.

Figure 10A:
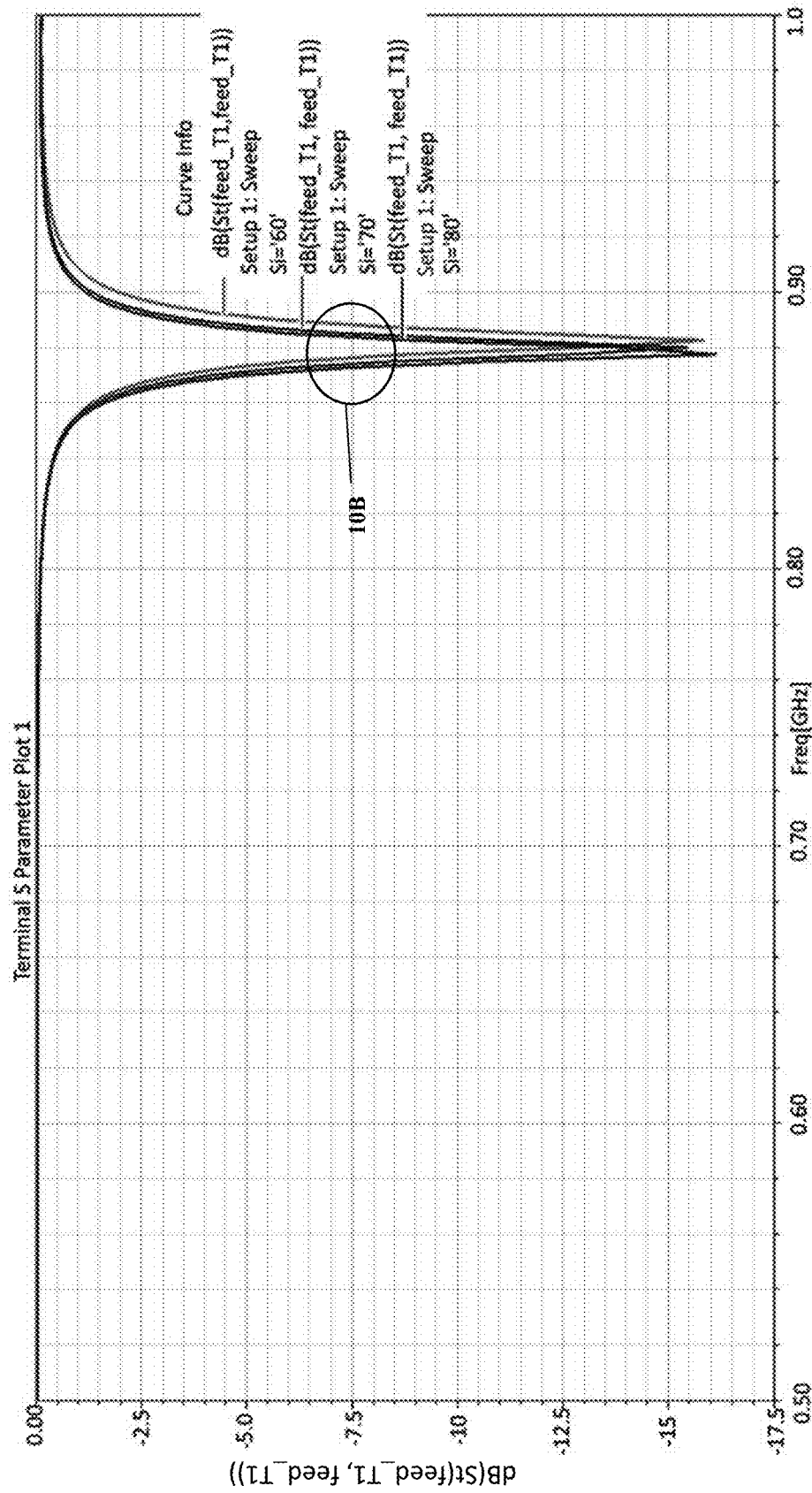
FIG. 10A is a graph of the terminal S parameter plot of the vein model antenna.
Figure 10B:
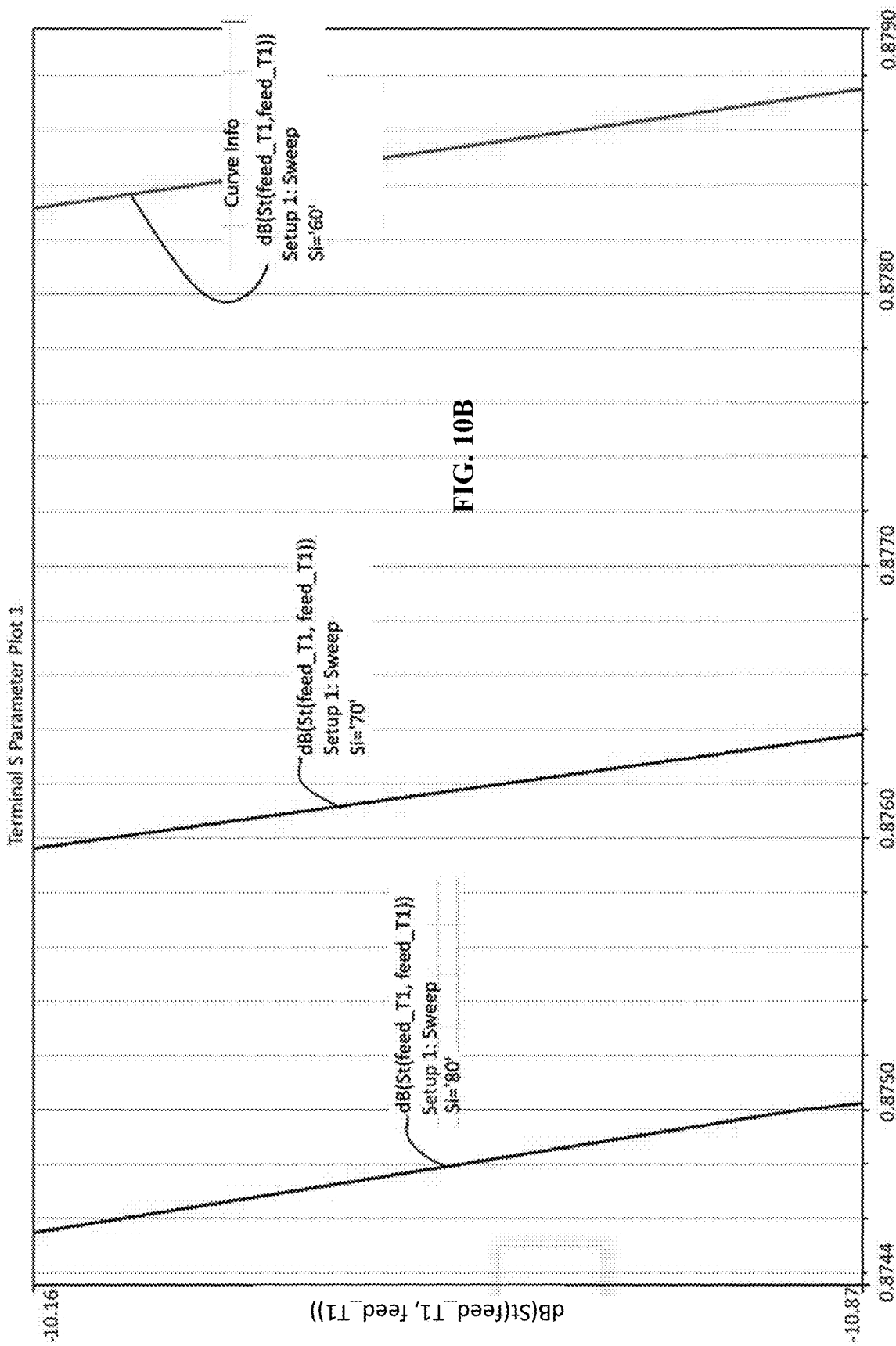
FIG. 10B is an enlarged view of the shift between S11 corresponding to the permittivity 60.

Sensitivity check for the vein topology design 200 showed the shift between the S11 corresponding to a permittivity 60 and that of the 80 is 3.8 MHz GHz, as shown in FIGS. 10A-10B.

Figure 11A:
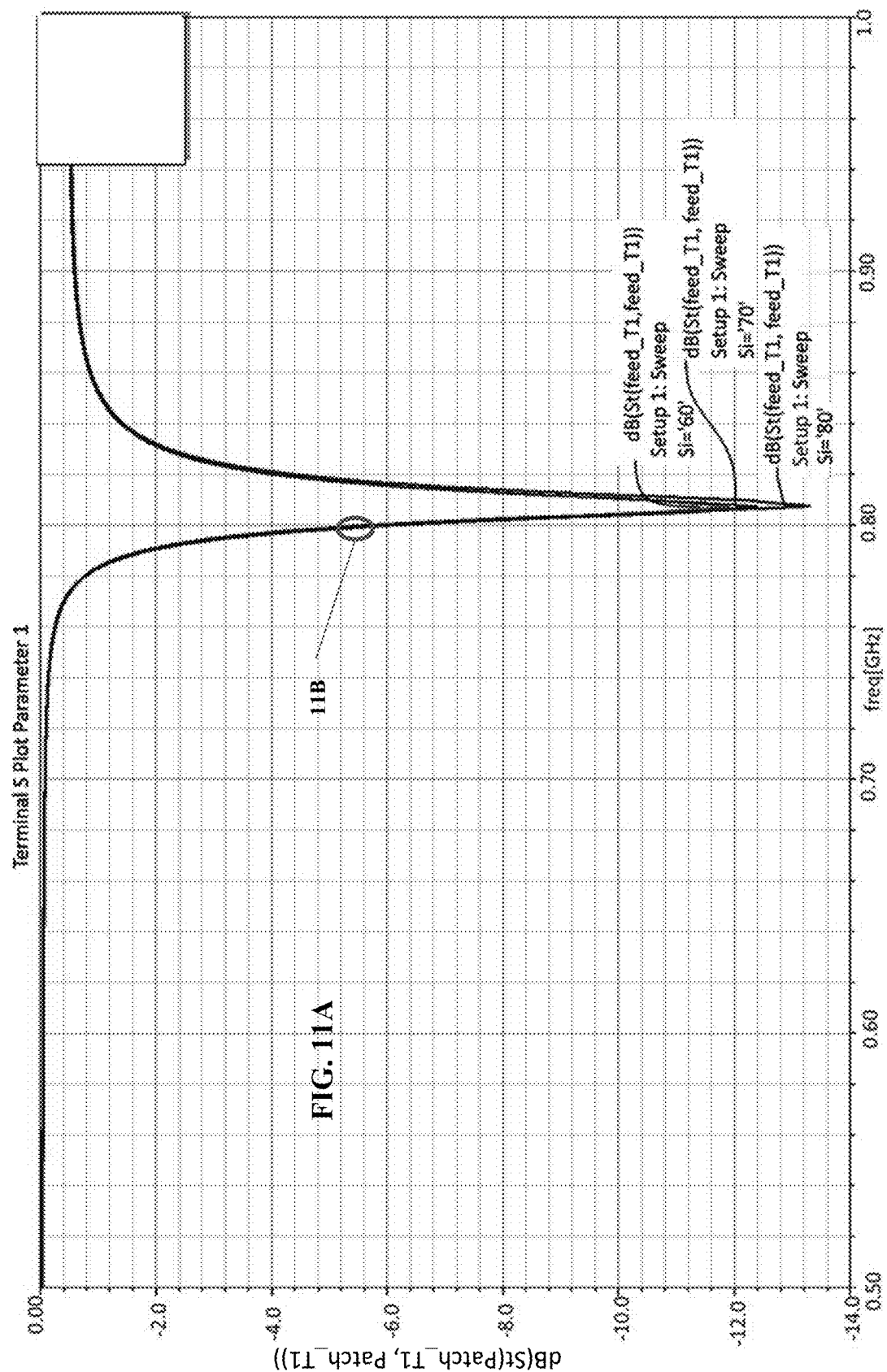
FIG. 11A is a graph of terminal S parameter plot to compare the V shape.
Figure 11B:
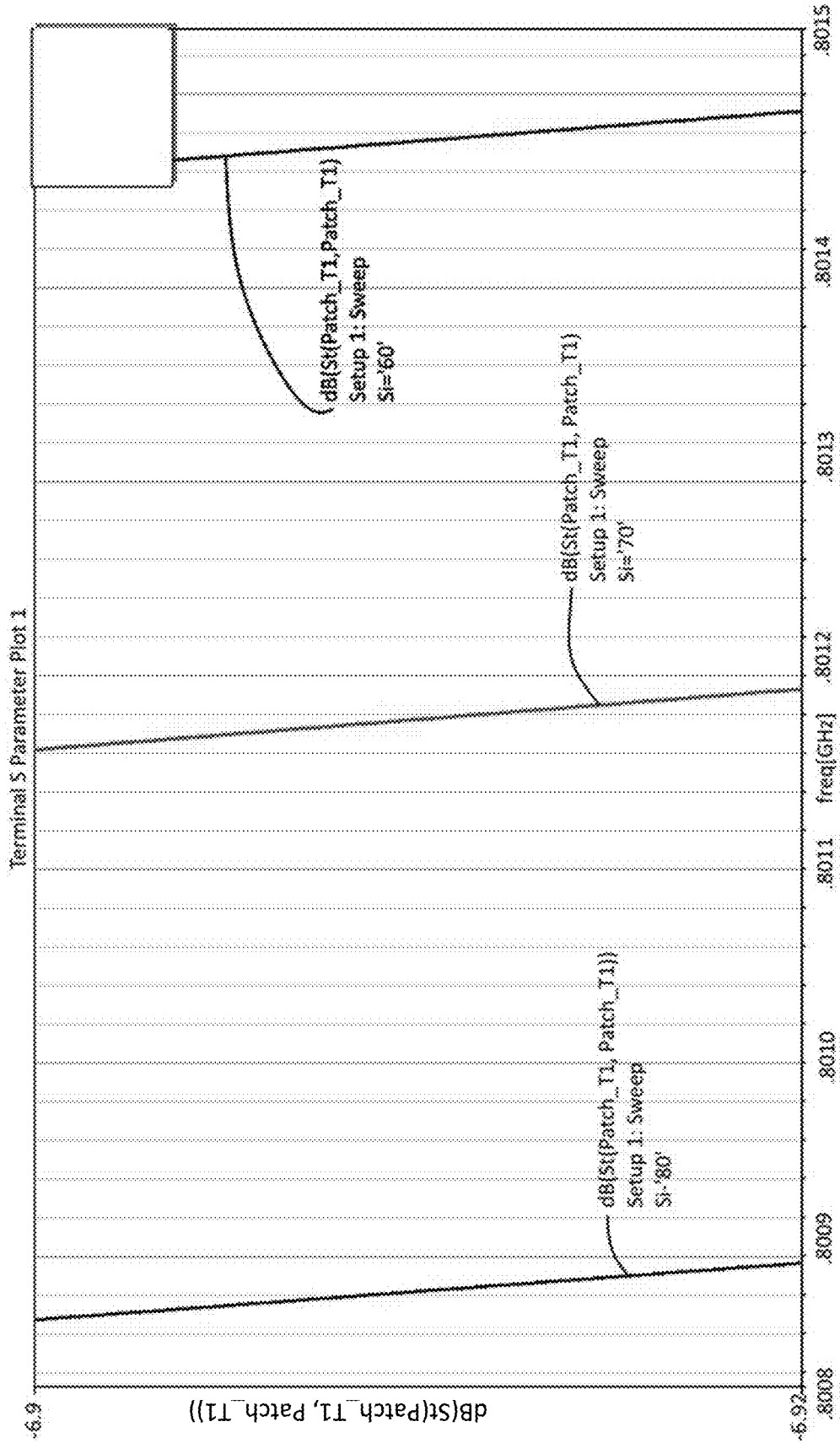
FIG. 11B is an enlarged view of the shift between S11 corresponding to the permittivity 60.

A simple V shape slot antenna operating at almost the same frequency (0.815 GHz) and having the same dimensions (7 cm by 7 cm) is compared to the slot design 200, as shown in FIGS. 11A-11B. The shift between the S11 corresponding to a permittivity 60 and that of the 80 is 0.6 MHz. The shift obtained using our sensor is almost 6 times greater than the response of this antenna. Hence, the shape of our antenna improves its sensitivity to the variation of permittivity hence the variation of glucose levels.

Figure 12:
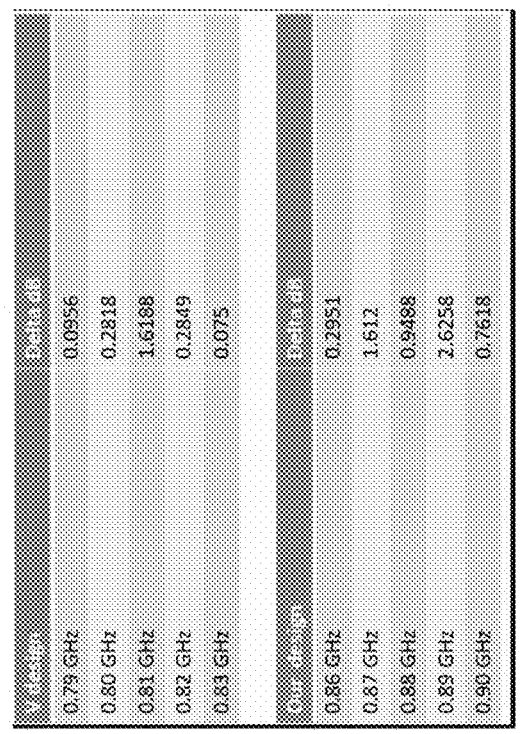
FIG. 12 is a table of the Sensitivity Check and dB drop near resonant frequency.

The Sensitivity Check of dB drop near resonant frequency is shown in FIG. 12. The two designs have different resonant frequencies. Higher sensitivity is obvious when the design follows the vein pattern. This is reflected in higher magnitude drop in dB around the respective resonant frequencies.

Figure 13A:
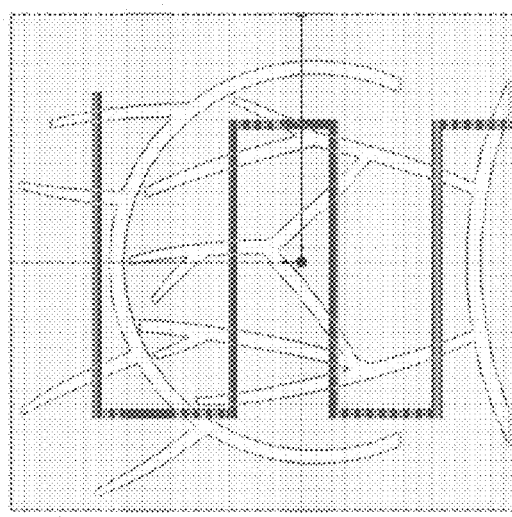
FIG. 13A is a schematic of the transmission line feeding the antennae in s spiral configuration.
Figure 13B:
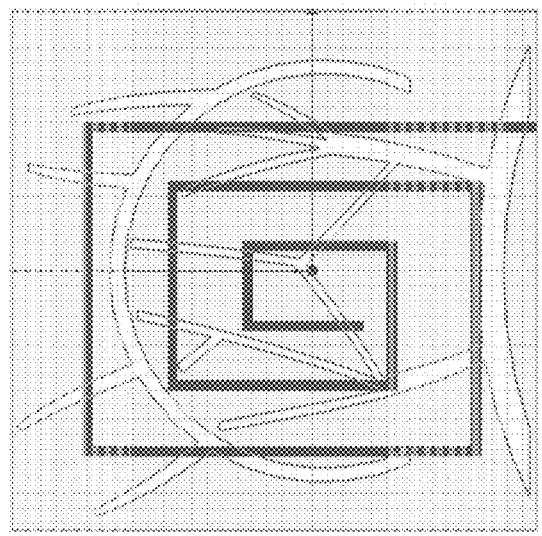
FIG. 13B is a schematic of the transmission line feeding the antennae in a coaxial configuration.

Feeding Methods:

In one embodiment, the antenna is fed using a transmission line. Different shapes of transmissions lines could be used to increase the coupling of the slots, as shown in FIGS. 13A-13B. For one sensor embodiment, a spiral transmission line as shown in FIG. 13B covers as many slots as possible. This makes the antenna operational at lower frequencies within the UHF band and additional resonant frequency appears. (add the simulations for spiral and periodic and simple straight transmission lines) Coaxial feed method could be used to improve the feeding system of the sensor, according to one embodiment.

Other embodiments for the feeding line can be designed to guarantee matching while enabling cross-over between the different slots and feeding line.

Sensor Substrate:

In one embodiment, the antenna is mounted along with different sensors (humidity, sweat, temperature . . . ) inside an anti-sweat/humidity gloves. The sensor is designed on a dielectric substrate with a very thin height. The same sensor can be designed on a flexible substrate to take the shape of each patient's hand. The flexible antenna can also be designed using an adhesive-flexible material such as silicon layers, skin-mounted adhesive and then fixed directly on the patient's hand. "Flexible" is the quality of bending easily without breaking and including a bend radius between about 5 mm and about 1000 mm. flexible plastic substrates, such as polyimide, PEEK, polyester (PET), polyimide (PI), polyethylene naphthalate (PEN), polyetherimide (PEI), along with various fluropolymers (FEP) and copolymers or transparent conductive polyester film allowing the antennae and sensor to conform to a desired shape, or to flex during its use. An alternative approach to flexible substrates is various etching techniques to thin down the traditional silicon substrate to few tens of micrometers to gain reasonable flexibility, referred to as flexible silicon (~5 mm bending radius).

Adjustment to Different Patients:

The response of the antenna is expected to change from one patient to another depending on many criteria including but not limited to: Skin thickness, color, type (hairy and glabrous skin); Skin perfusion, hydration; Sweating; Patient metabolism and body mass index; and other medical conditions such as cholesterol, diabetes.

To adjust the response of the antenna, first the linear region is detected using signal processing techniques and then the resonance frequency of the antenna is adjusted to cover this linear zone. The reconfigurable resonance frequency will improve the sensitivity of the sensor and make it more personalized for each patient.

Possible Alternate Implementations of the Design:

This sensor can detect the variation of permittivity hence it can be used in different applications such as: Blood Glucose detection and any other blood Biomarkers, hydration monitoring/blood flow, Cholesterol, Bone fracture healing monitoring, cardiac activity: heart rate, blood pressure, and Material/liquid characterization. A similar design can be used to administer localized radiation-based treatment jointly with/without medication to specific underlying patterns/structures.

Metrics that are Measured:

The sensor is connected to a network analyzer to convert the detected energy into magnitude and phase. For the antenna, S11 parameters are detected including, but not limited to: Magnitude, and Phase or impedance, and to derive the Power level.

Predictive Modeling for Selection of Critical Features:

The sensor is connected to a signal processing system to convert the magnitude and/or the phase into concentration of the blood constituents. The Predictive modeling for selection of critical features comprises 1) Measuring the S11 parameters using the sensor; 2) Preprocessing of the data outlier and noise removal using different techniques (wavelet, moving average filters or other types of filters); 3) extracting feature; 4) Modeling, calibrating and tuning; and 5) recalibrating model for enhanced accuracy.

Preprocessing of the data comprises outlier and noise removal using different techniques (wavelet, moving average filters or other types of filters);

Extracting features comprise S11 Magnitude, S11 phase and/or impedance is sampled into different frequency components. The features are then normalized (between −1 and 1): Remove the reference value (equivalent to the values corresponding to a glucose concentration of 80 mg/dl for example); Remove the mean of each metric; Divide by the maximum of each metric.

Modeling, calibrating and tuning comprises regularized regression in one embodiment is used to predict the glucose concentrations (Lasso, PLS, Hybrid models . . . ). Single feature model and multiple-feature models can be used in some embodiments. Time based models can be used.

In one embodiment, the antennae is a Rigid Antennae as shown in FIG. 1B with the following parameter for the Substrate: Rogers RO3203, Thickness t=0.51 mm, Dielectric $\varepsilon_r$=3.02; (The thickness and dielectric values may vary to +/−5% due to fabrication methods for this type of substrate.) As such, the Thickness t may be between about 0.45 mm and about 0.54 mm; and the Dielectric $\varepsilon_r$ is between about 2.80 and about 3.20. In one embodiment, the dimensions: 70*70*0.51 $mm^3$; Feeding: Spiral; Frequency range of interest: about 0.5 GHz-about 3 GHz; Measured parameters: Reflection coefficients (S11): magnitude and phase. The dimensions may range between about 50-100 mm for the width, about 50-100 mm for the length, and about 0.2 mm to 1.0 mm for the thickness. Alternative substrate material can be utilized and requires redesign of the antenna component, according to one embodiment.

The specific substrate RO3203 has 4 different standard thicknesses at (0.25 mm) 0.020" (0.50 mm) 0.030" (0.75 mm) 0.060" (1.52 mm). In other embodiments, the thickness or another substrate from another provider, or same provider but different production number, (may be with different dielectric constant or material), the antenna component is redesigned accordingly.

In another embodiment, the antennae includes a flexible substrate, as shown in FIG. 1D, including the following parameters, Substrate: PET (polyethylene terephthalate); Thickness t=136 um; Dielectric Constant $\varepsilon_r$=2.99; tangent delta=5.79e-3; (The thickness, dielectric constant, and tangent delta values may vary due to fabrication errors for a specific substrate series.) Substrate providers offer different substrate materials and thickness. Most popular are Kapton® Polymides. As such, for example, for the specific substrate, the Thickness t may be between about 129 μm and about 143 μm the dielectric constant may also be subject to fabrication process variation and so does the tangent delta. Dimensions: 70*80*0.51 $mm^3$; Feeding: Spiral; Frequency range of interest: is between about 0.5 GHz-3 GHz; Measured parameters: Reflection coefficients (S11): magnitude and phase. PET is used in one embodiment as the polymer; other types flexible material exist such as paper substrates, and other flexible substrate requires a complete redesign of the entire antenna component. While a wide range of thickness may be incorporated into the embodiments, most flexible films are provided in a narrow range of relatively thin dimension from about 12 µm to about 125 µm (1/2 mil to 5 mils) as thinner and thicker material are possible in other embodiments. Kim, Sangkil, and Manos M. Tentzeris. "Parylene coated waterproof washable inkjet-printed dual-band antenna on paper substrate." International Journal of Microwave and Wireless Technologies 10.7 (2018): 814-818.

Modeling Techniques

The reflection coefficient S11 phase and magnitude measurements obtained for a given antenna (rigid or flexible) at multiple frequencies are used for the estimation of glucose levels, according to one embodiment.

Different regression techniques are tested to best identify the most suitable models that capture the underlying variation in glucose level. Radial basis function (RBF), Gaussian Process (GP), Locally weighted Partial least square (LW_PLS) enable several desired properties, including, but not limited to: sparsity, reduced variance and capture more accurately the local behavior. Particularly, there is a need for localized model coverage to enhance accuracy in the regions corresponding to low glucose level. Other regression techniques include Partial least square (PLS) and Least absolute shrinkage and selection operator (LASSO).

The PLS is a regression technique based on sparsity and maximizing correlations. It generates new regressors, called PLS directions, which are formed by linearly combining the original variables, depending on their univariate influence on the target. Hence the importance of this technique is that it creates the PLS directions by maximizing both their variance of the new regressors (similar to principal components) and the correlation of the regressors with the output variables.

Radial Basis Function (RBF) is a nonlinear regression technique that utilizes basis function (Radial basis function): $y=f(x)=\Sigma_K w_k b_k(x)$ for the 1D case. A radial function is a function that is radially symmetric around some point xc called the function's center. Different RBFs could be used. Optimization methods are utilized to find the best function centers and parameters.

Gaussian process (GP) is a modeling technique that also provides uncertainty information about the estimate at a given point xq. This technique relates the point xq to the different training points x using a covariance function, k(x, xq) based on their distance, so again it can emphasize the local influence of the training points depending on the model parameters.

In Locally weighted PLS, PLS is used to build a local linear regression model specific for each new point, x0, whose performance is to be predicted. The model provides distance based weights for each training point, based on the distance between x0 and the different training points. The process is iterative and the model underneath uses linear regression in the form of PLS (unlike RBF and GP). So it employs PLS directions as new regressors.

For each x0, the newly generated local model strongly depends on the similarity/proximity between x0 and the training samples. In the model, the Euclidean distance was distance.

EXAMPLES

The following examples are put forth so as to provide those of ordinary skill in the art with a complete disclosure and description of how the compounds, compositions, articles, devices and/or methods claimed herein are made and evaluated, and are intended to be purely exemplary of the invention and are not intended to limit the scope of what the inventors regard as their invention. However, those of skill in the art should, in light of the present disclosure, appreciate that many changes can be made in the specific embodiments which are disclosed and still obtain a like or similar result without departing from the spirit and scope of the invention.

Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

Example 1: In Vitro Experiment on Serum

Figure 14:
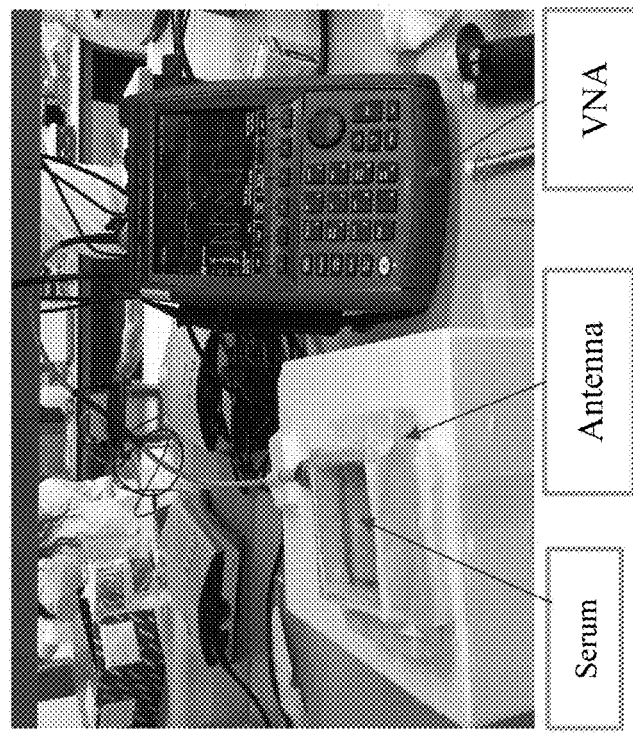
FIG. 14 is a schematic showing the experimental setup.
Figure 13A:
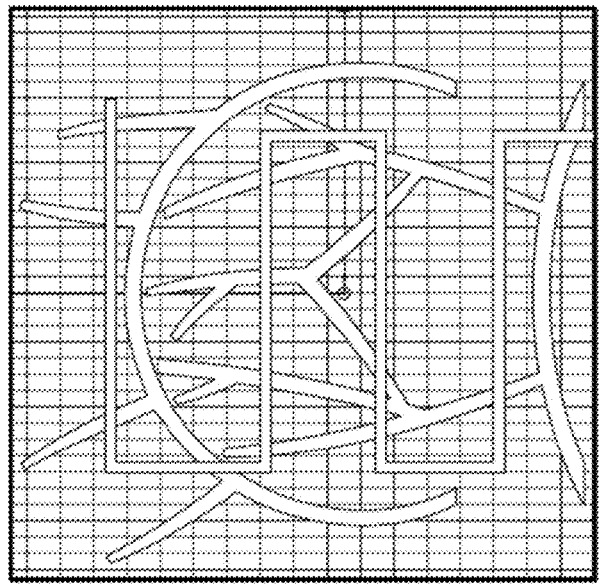
Figure 13B:
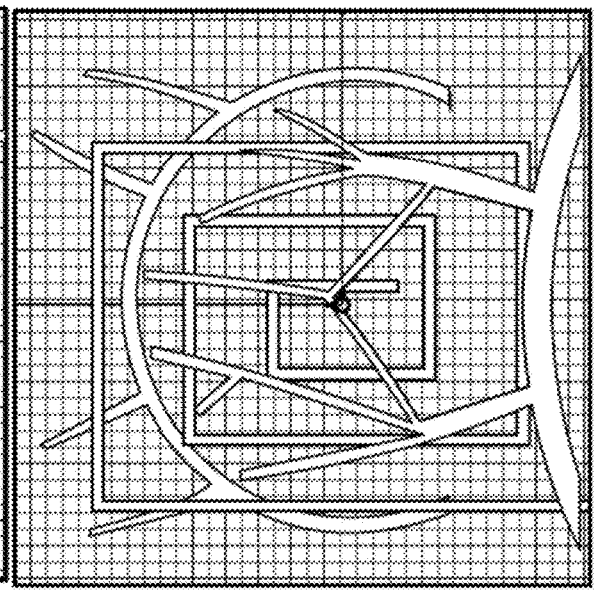
Figure 14:
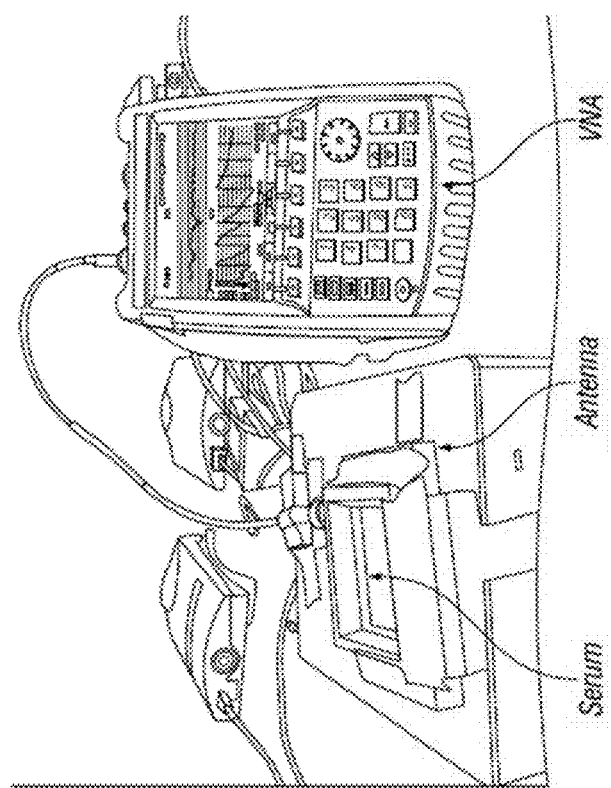

Experimental Setup for the in vitro experiment is shown in FIG. 14. A foam container is filled with 30 ml of Fetal Bovine Serum FBS/glucose solutions, which is very close to the blood in terms of composition. Foam dimension: same size of the antenna (70*70 mm$^2$) and a thickness of 0.5 cm. The container is kept fixed during the whole experiment.

An initial measurement is done. A reference glucose level is taken using the Glucotrack glucometer from Roche. For each measurement, 10 repeated readings for the S11 magnitude and phase are taken using the vector network analyzer (VNA). This is to average out any error resulting from the measurements. The S11 values were recorded over the whole desired frequency range.

After each measurement, the glucose level was increased slightly for the next measurements. A small amount of glucose, equivalent to 10 mg/dl, is added to the FBS solutions. After each addition of glucose, the FBS solution is mixed and left for 10 minutes to insure the homogeneity of the solution. The same procedure is repeated until the glucose levels of the FBS reaches around 500 mg/dl. Same experiment is done on both the rigid and flexible antennas: A total of 41 measurements were taken for the rigid antenna and 38 measurements for the flexible one.

Figure 15A:
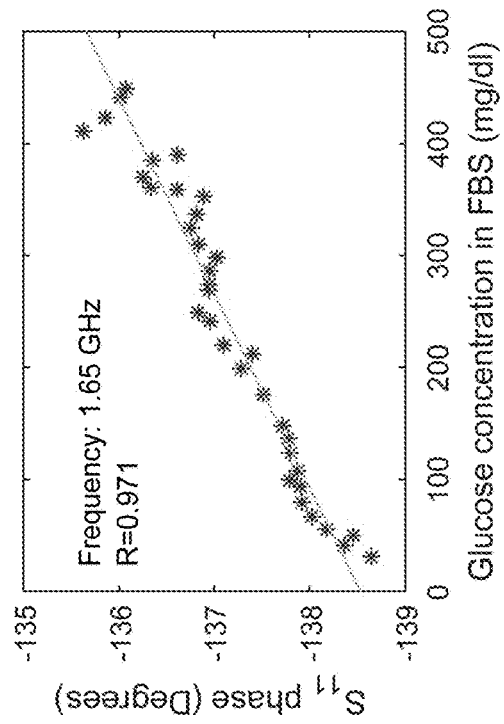
FIG. 15A is a graph showing the response to glucose during in serum-based experiments using the semi-flexible antenna (Rigid) and the semi-flexible antenna's response (S11) to glucose variation. Glucose concentration of the fetal bovine serum (FBS) solution was varied with very small steps from 50 mg/dl to 445 mg/dl. The normalized S11 versus the reference glucose levels obtained by the commercial invasive glucometer. The cyan line is the S11 fitted curve showing the trend of the antenna's response when the glucose levels increase.
Figure 15B:
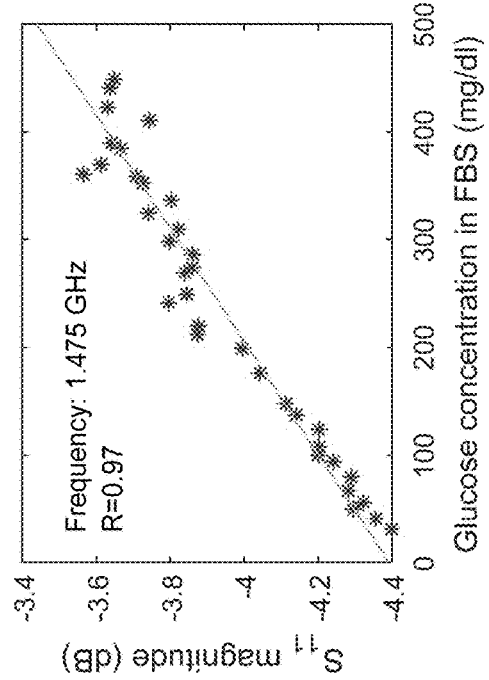
FIG. 15B is a schematic of the in vitro experiment configuration; a foam container, filled with FBS-glucose solution is placed on top of the antenna. The top sensing layer of the antenna, containing the biologically inspired slots as previously discussed, is positioned facing the FBS solution.
Figure 15C:
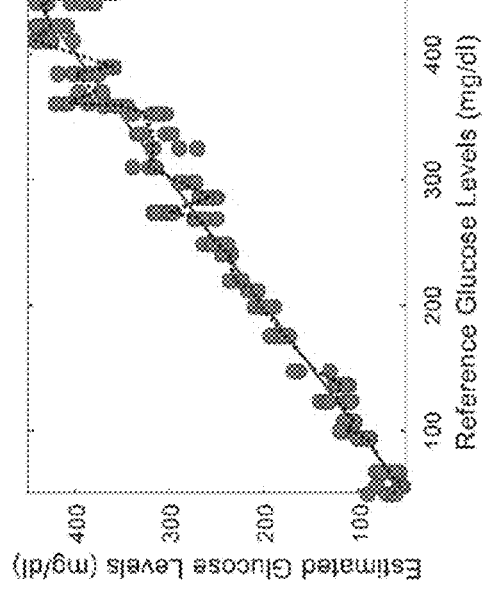
FIG. 15C is a graph showing the glucose levels estimation and model performance. The estimated glucose levels obtained by the proposed sensing system versus the reference glucose levels in the FBS solution (in red), using Gaussian process.

FIGS. 15A-15C show the response to glucose during in serum-based experiments using the semi-flexible antenna embodiment. Individual OGTT models were developed. Normalization performed within each OGTT. 10 random replications (division in test and train data) were performed for each OGTT to give better idea about the error. Only GP(Gaussian process) was adopted. FIG. 15A shows the semi-flexible antenna's response (S11) to glucose variation. Glucose concentration of the FBS solution was varied with very small steps from 50 mg/dl to 445 mg/dl. The normalized S11 versus the reference glucose levels obtained by the commercial invasive glucometer. The cyan line is the S11 fitted curve showing the trend of the antenna's response when the glucose levels increase. These S11 values are recorded at different frequencies, corresponding to the highest correlations between the S11 and the glucose reference levels. These features and others are used for the estimation of BG levels through GP regression modeling. FIG. 15B is a schematic of the in vitro experiment configuration, including a foam container, filled with FBS-glucose solution is placed on top of the antenna. The top sensing layer of the antenna, containing the biologically inspired slots, is positioned facing the FBS solution. FIG. 15C shows the glucose levels estimation and model performance. The estimated glucose levels obtained by the proposed sensing system versus the reference glucose levels in the FBS solution (in red), using Gaussian process. The data is randomly divided into two sets: ⅔ to build the model and ⅓ to test its performance. Because of the limited number of observations in the datasets, this process is repeated 10 times. The green filled circles represent the predicted glucose levels obtained during the 10 repetitions of process and the blue dotted curve is the mean predicted value. Using the wrapper for the feature and the kernel selection, rational quadratic is utilized as kernel function along with 11 features to build the model. The mean absolute relative difference (MARD) between the reference and the predicted GL is 4.96%.

Results—Flexible Antenna

For a given patient, all three tolerance tests (OGTTs) normalized to one reference value although they were spaced out in time. A prediction was included on the three OGTT. In some cases, leave one out error was calculated. Or datasets were divided to ⅔ ⅓ and predicted error. Testing across different possible models.

Figure 16A:
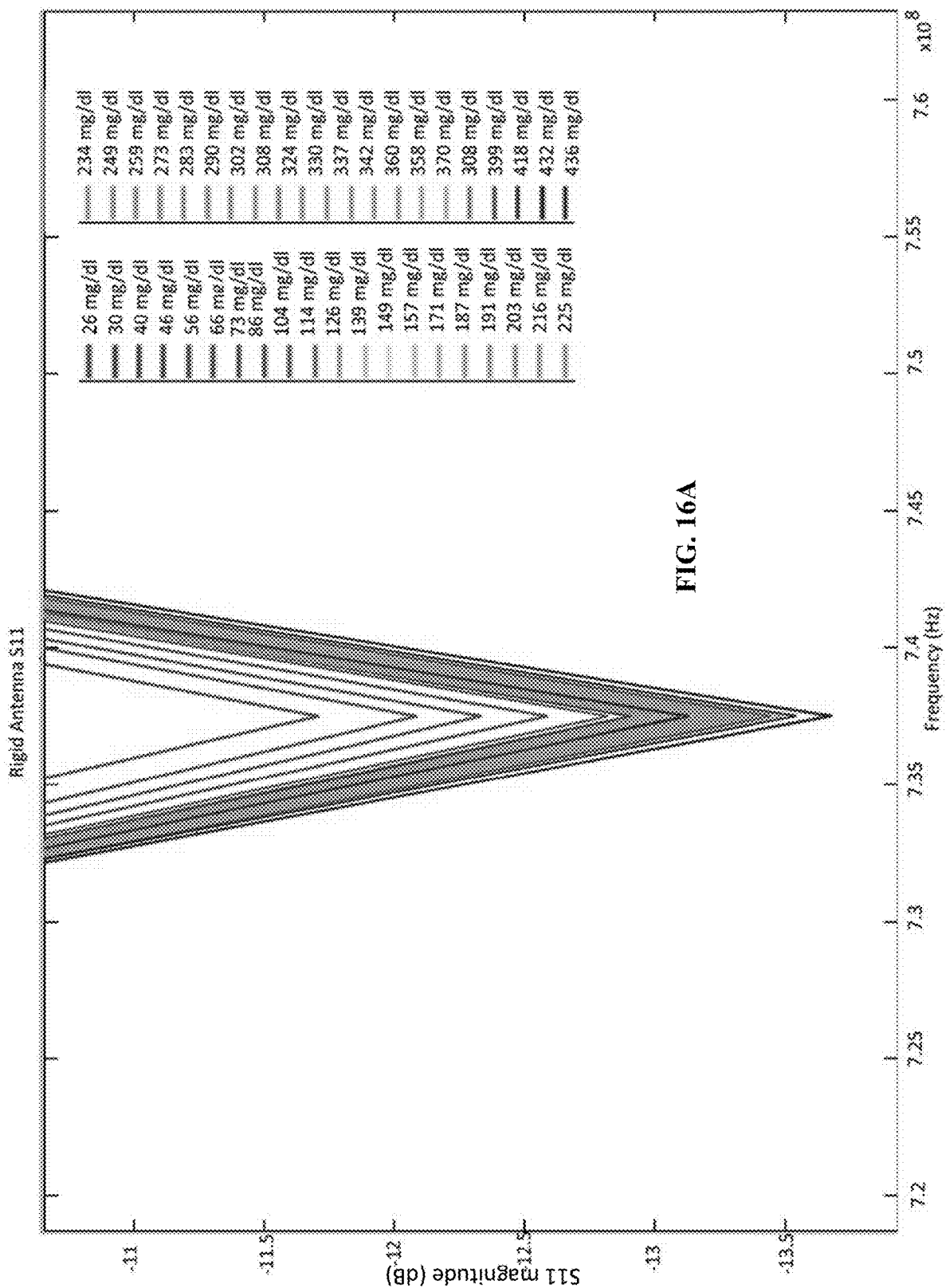
FIG. 16A is graph demonstrating different S11 magnitude plots over the regions 1.5 and 2 GHz, for different serum glucose levels.

FIG. 16A is demonstrating different S11 magnitude plots over the regions 1.5 and 2 GHz, for different serum glucose levels for the flexible antenna embodiment.

Figure 16B:
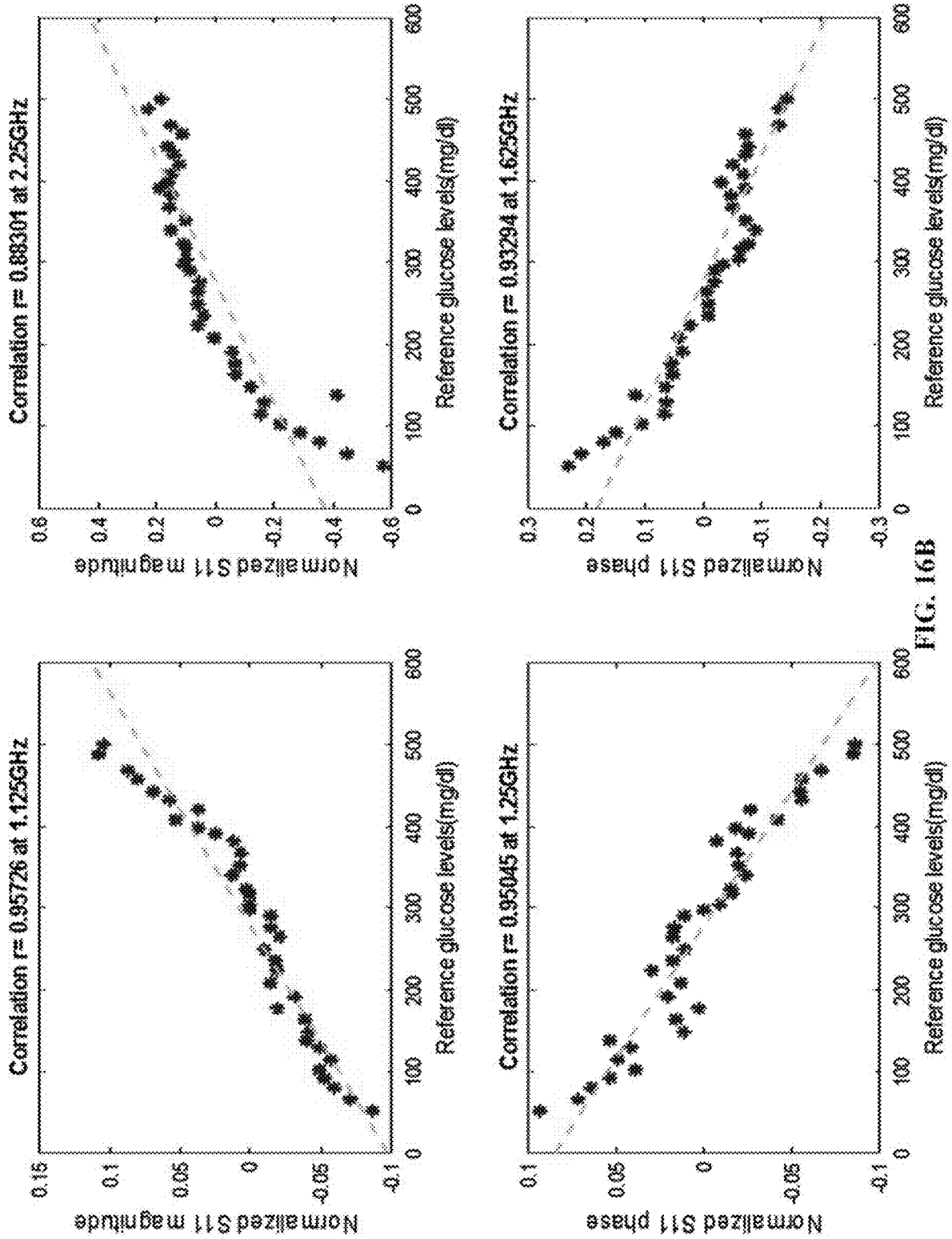
FIG. 16B are graphs showing an example of the Normalized S11 magnitude and phase recorded at different frequencies Vs the reference glucose levels.

FIG. 16B is an example of the Normalized S11 magnitude and phase recorded at different frequencies Vs the reference glucose levels for the flexible antenna embodiment.

Figure 16C:
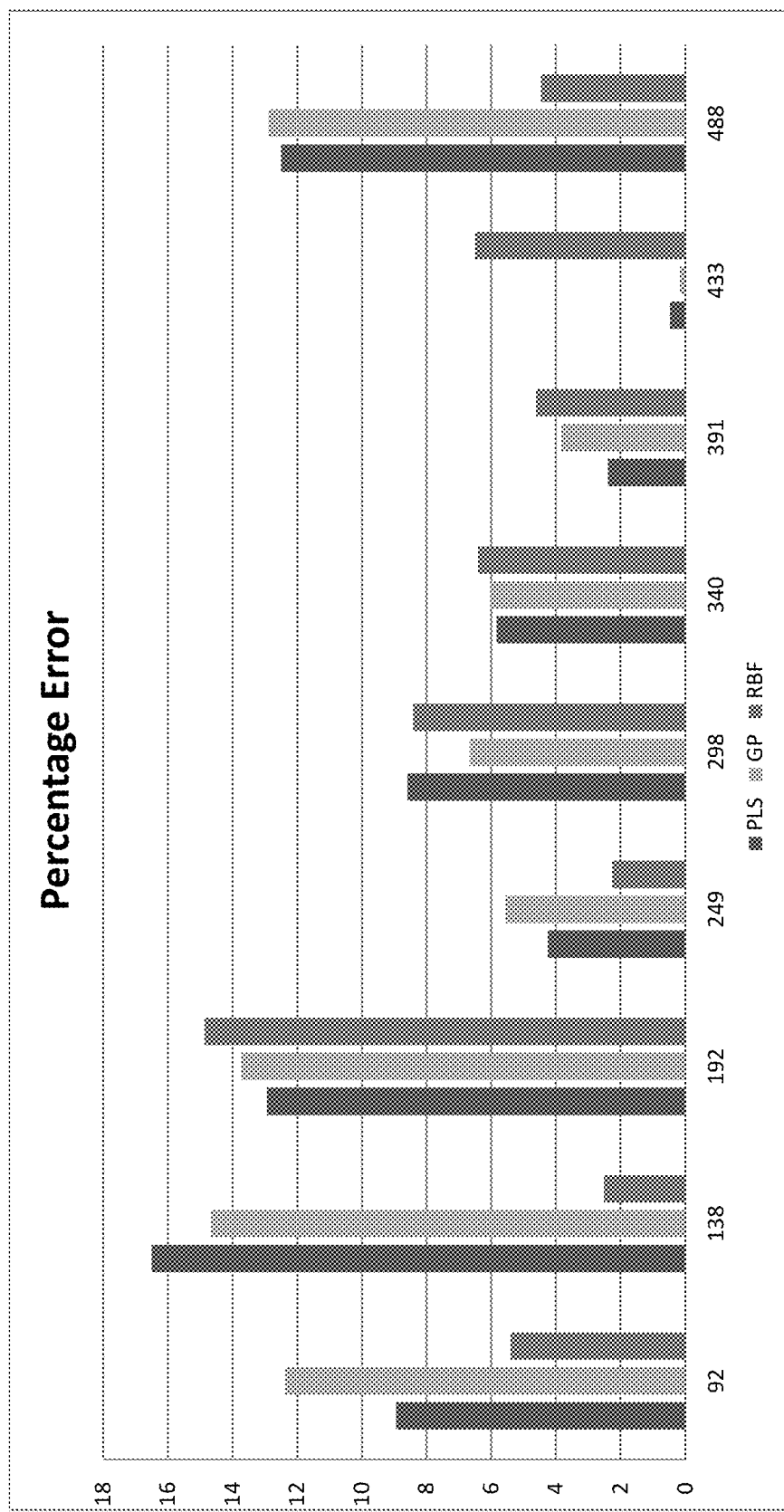
FIG. 16C is a graph showing when the data is split into (⅔) training and (⅓) testing.

FIG. 16C is a graph showing when the data is split into (⅔) training and (⅓) testing.

TABLE 1

| Percentage Error | PLS | GP | RBF |
|---|---|---|---|
| mean | 8.049582 | 8.437529 | 6.161266 |
| max | 16.49812 | 14.69032 | 14.86161 |
| min | 0.476658 | 0.159306 | 2.26402 |

Figure 18B:
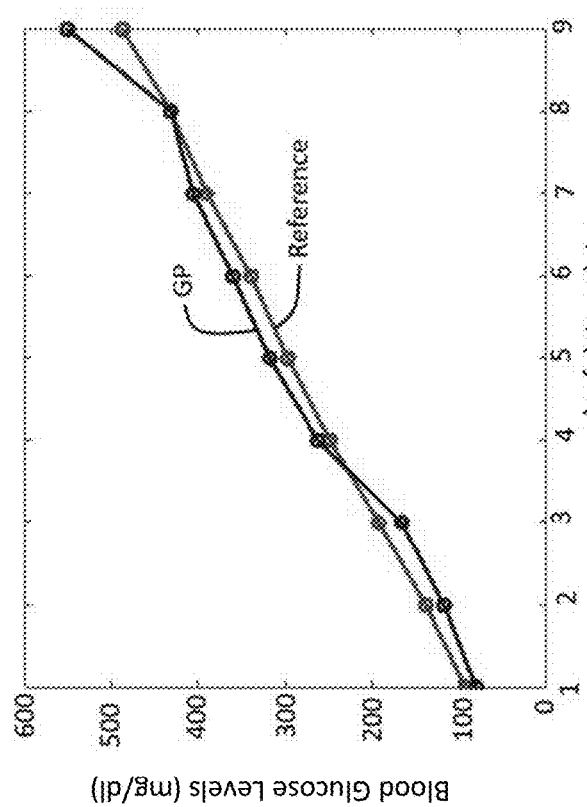
FIGS. 18A-18C are graphs showing when the data is split into ⅔ training and ⅓ testing.
Figure 18A:
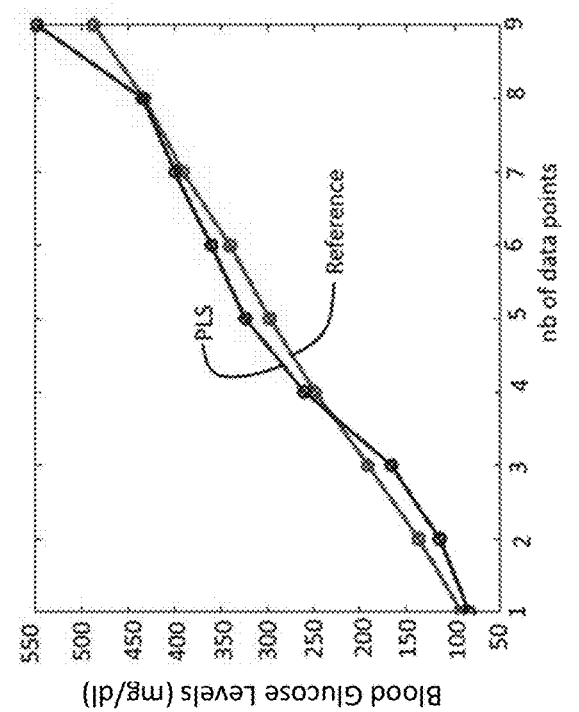
Figure 18C:
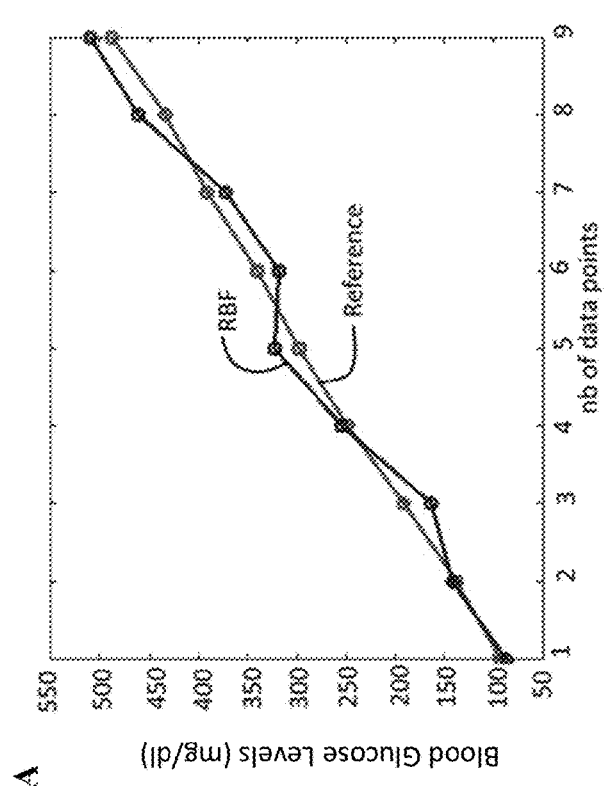

FIGS. 18A-18C are graphs showing when the data is split into ⅔ training and ⅓ testing for the flexible antenna embodiment.

Figure 19A:
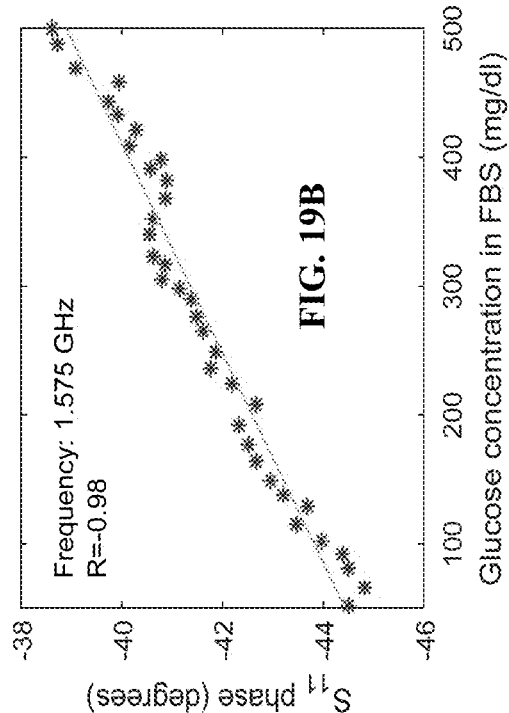
FIGS. 19A-19B show the response to glucose during in serum-based experiments using flexible antenna.
Figure 19B:
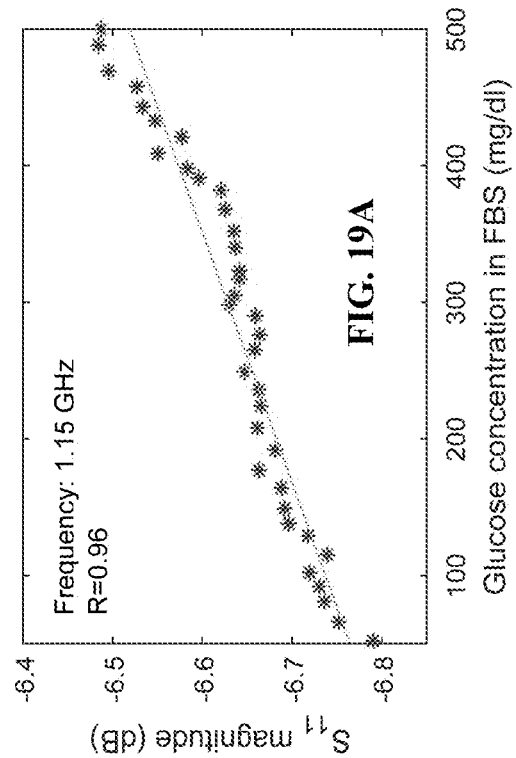
Figure 19C:
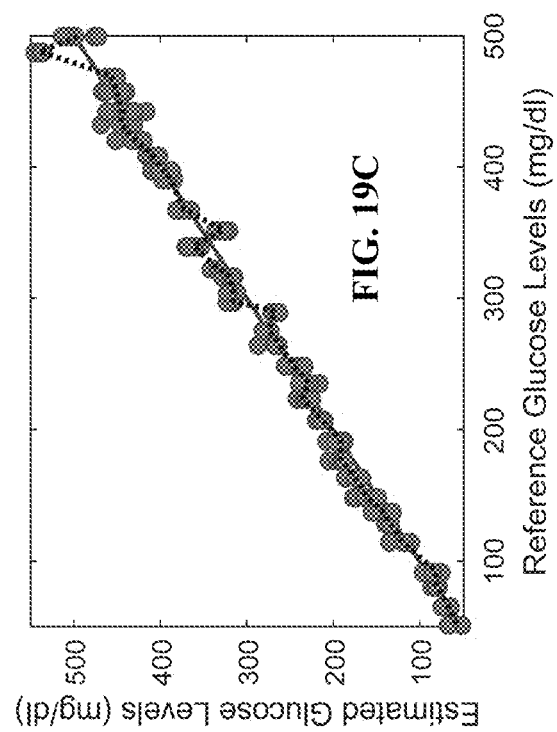
FIG. 19C is a graph showing the estimated glucose levels obtained by the proposed sensing system versus the reference glucose levels in the FBS solution.

FIGS. 19A-19B show the response to glucose during in serum-based experiments using flexible antenna. FIG. 19A shows the flexible antenna's response (S11) to glucose variation. Glucose concentration of the FBS solution are varied with very small steps from 50 mg/dl to 500 mg/dl. Left: S11 magnitude versus to the reference glucose levels obtained by the commercial invasive glucometer. The cyan line is the S11 fitted curve showing the trend of the antenna's response when the glucose levels increase. These S11 magnitude values are recorded at 1.15 GHz which correspond to one of the frequencies achieving high linear correlation between the S11 and the glucose reference levels with r=0.96. FIG. 19B is a graph showing the S11 phase versus to the reference glucose levels. These S11 phase values are recorded at 1.575 GHz, achieving a correlation of −0.98. FIG. 19C shows the estimated glucose levels obtained by the proposed sensing system versus the reference glucose levels in the FBS solution. The mean absolute relative difference (MARD) between the estimated and reference values is 3.09%.

Figure 20A:
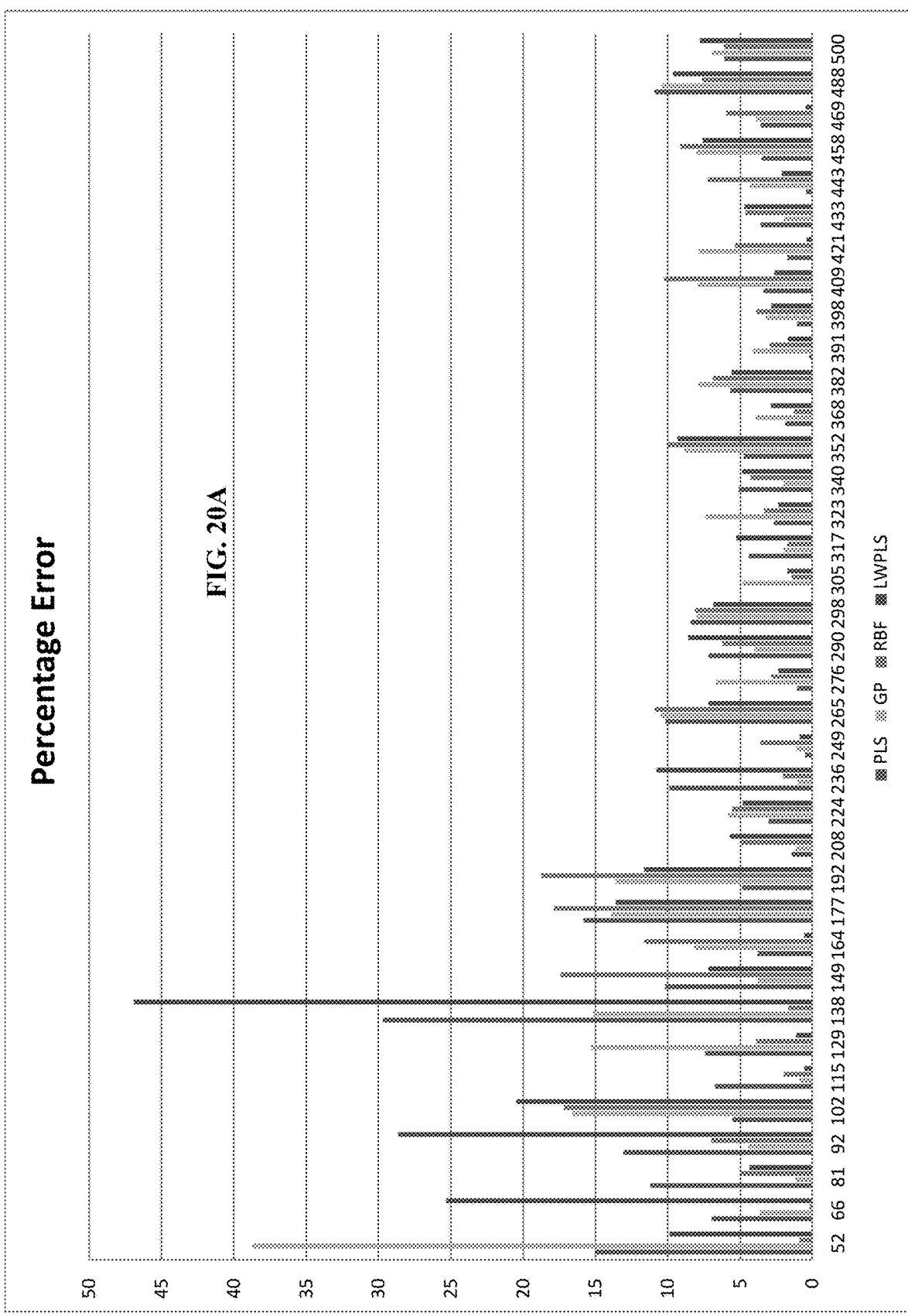
FIG. 20A is a graph showing Flexible Antenna Leave One Out.
Figure 20C:
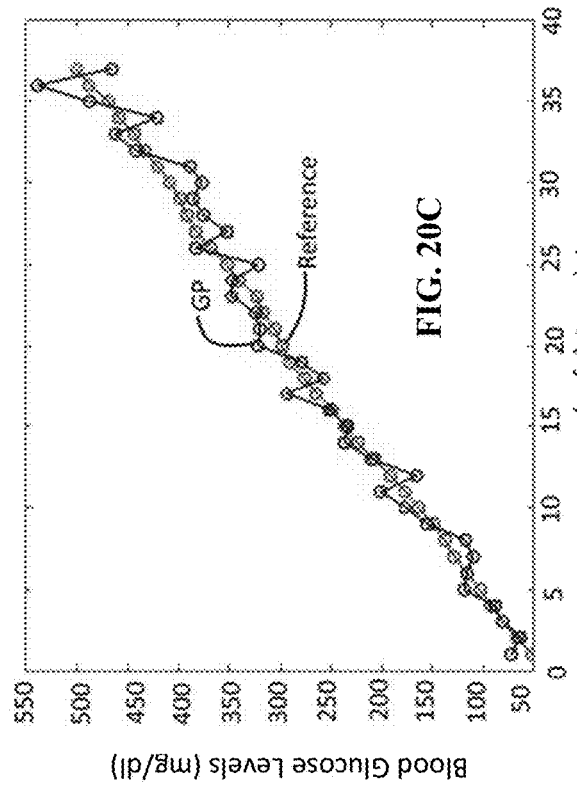
FIGS. 20B-20E are graphs showing the Flexible Antenna Leave One Out.
Figure 20E:
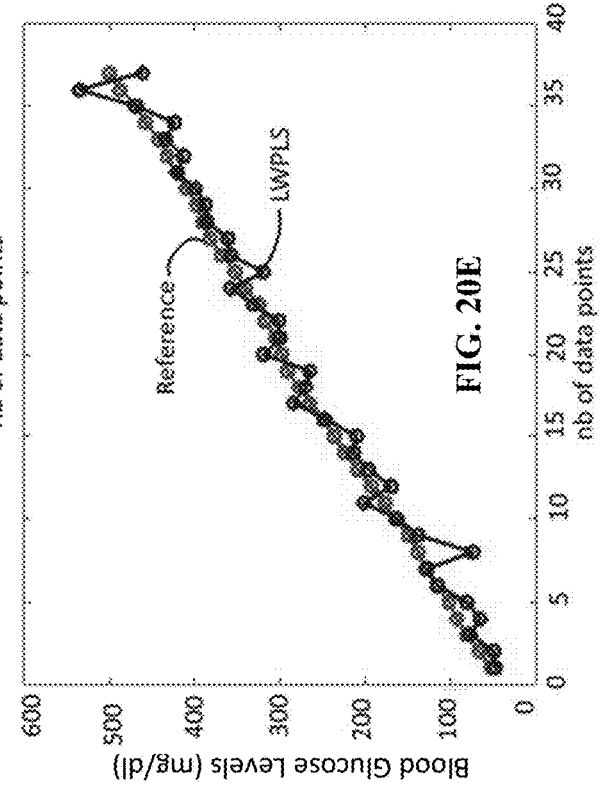
Figure 20B:
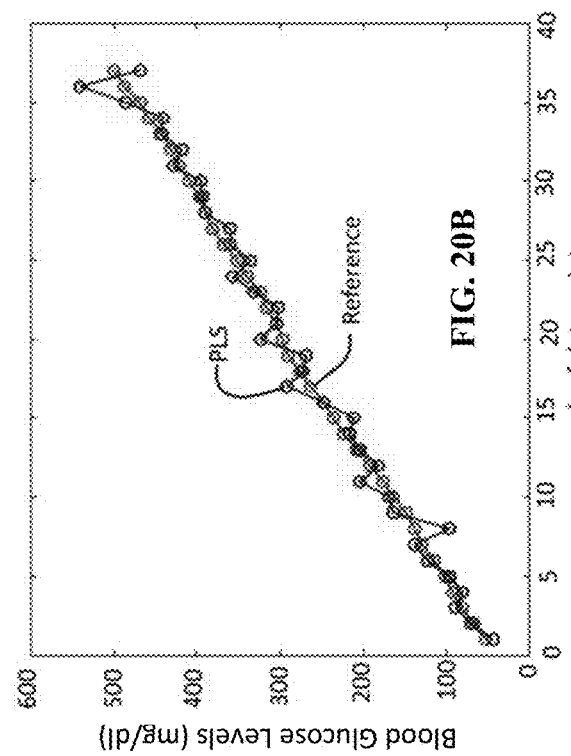
Figure 20D:
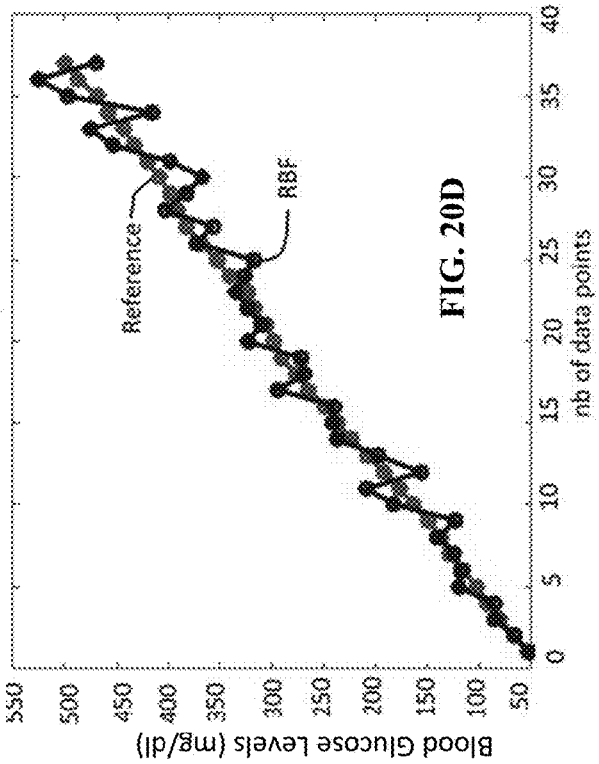

FIG. 20A is a graph showing Flexible Antenna Leave One Out for the PLS, GP, RBF, and LW PLS modeling techniques, as shown in Table 2.1 below.

TABLE 2.1

| | PLS | GP | RBF | LW PLS |
|---|---|---|---|---|
| Mean | 6.260251 | 7.291513 | 6.501052 | 7.832199 |

FIGS. 20B-20E are graphs showing the Flexible Antenna Leave One Out for the PLS, GP, RBF, and LW PLS modeling techniques.

Figure 21A:
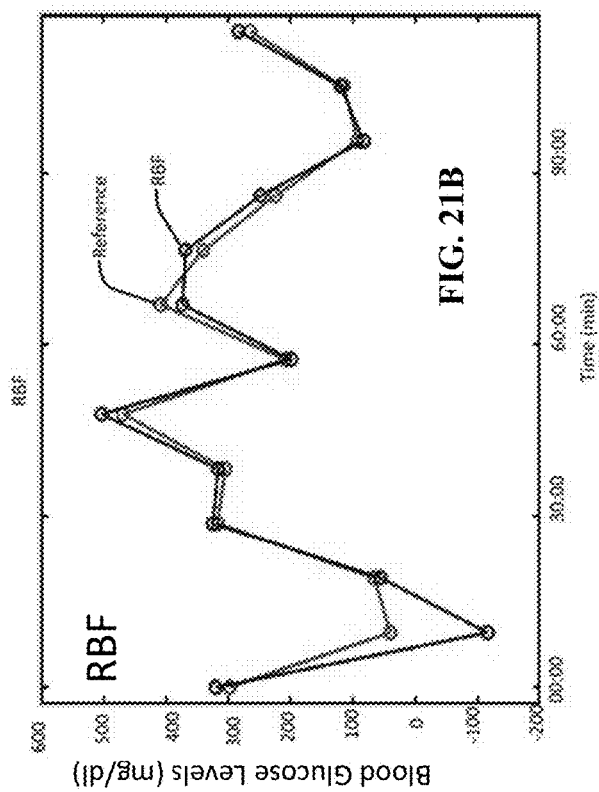
FIGS. 21A-21C are graphs of the estimated glucose level values, when the data is split into ⅔ training and ⅓ testing.
Figure 21B:
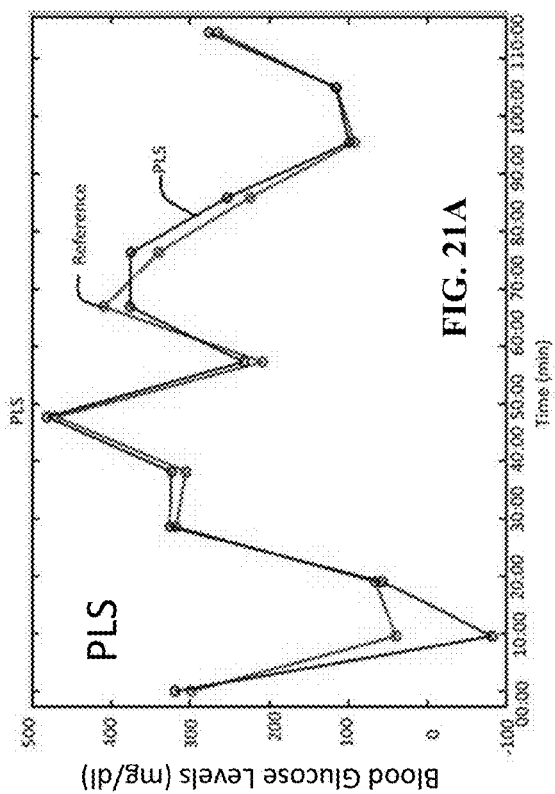
Figure 21C:
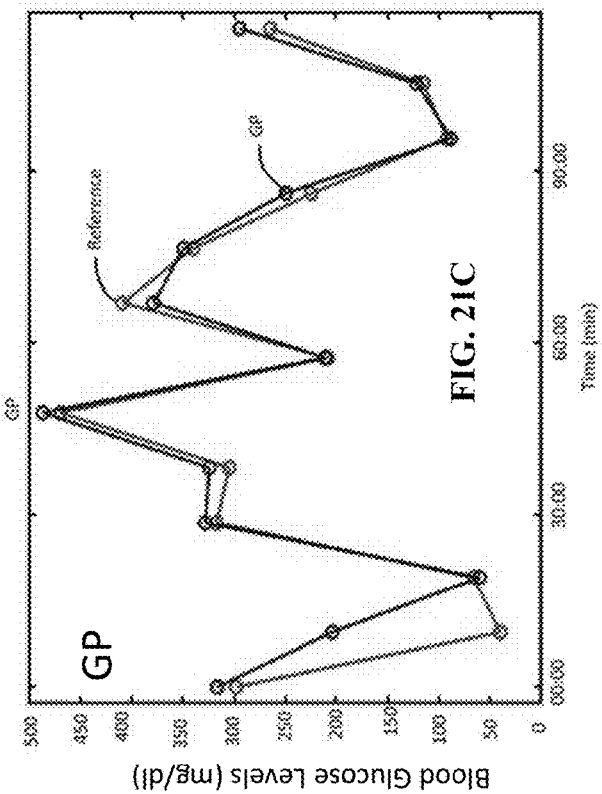
Figure 22A:
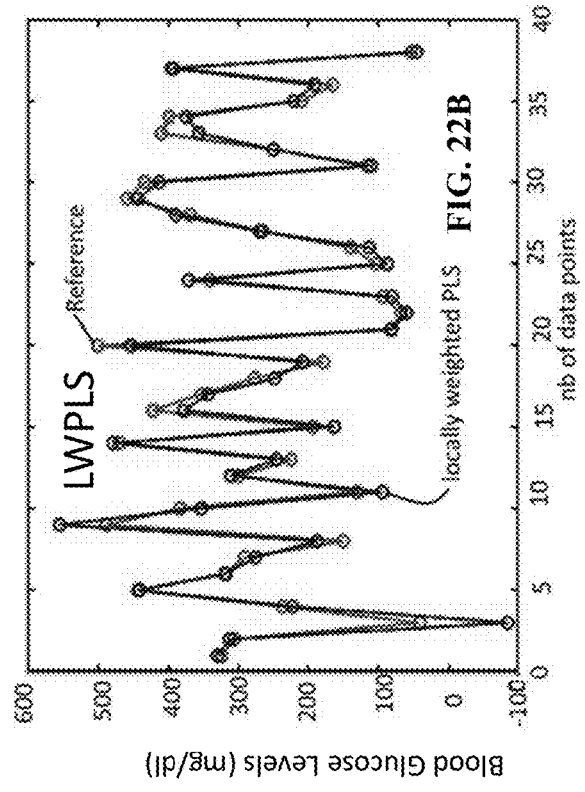
FIGS. 22A-22D are graphs showing when one is left Out: where each point is considered a test point, and the remaining points are used to build the model.
Figure 22B:
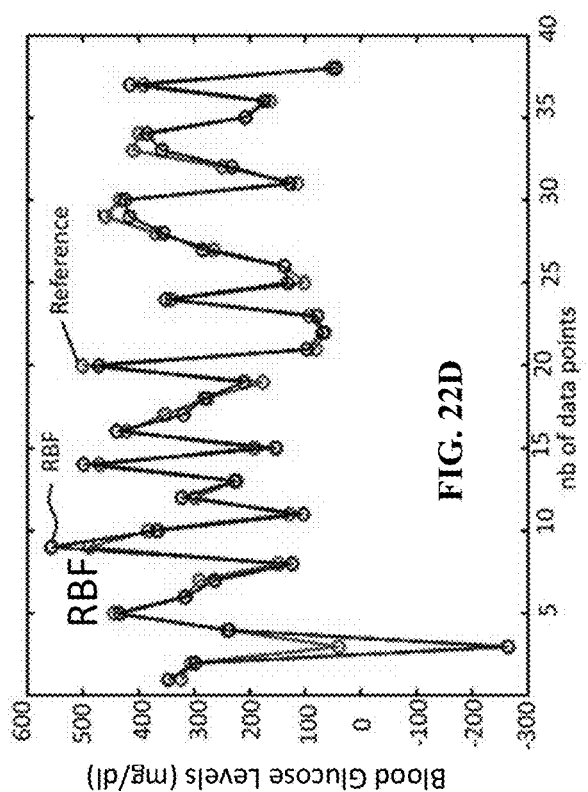
Figure 22C:
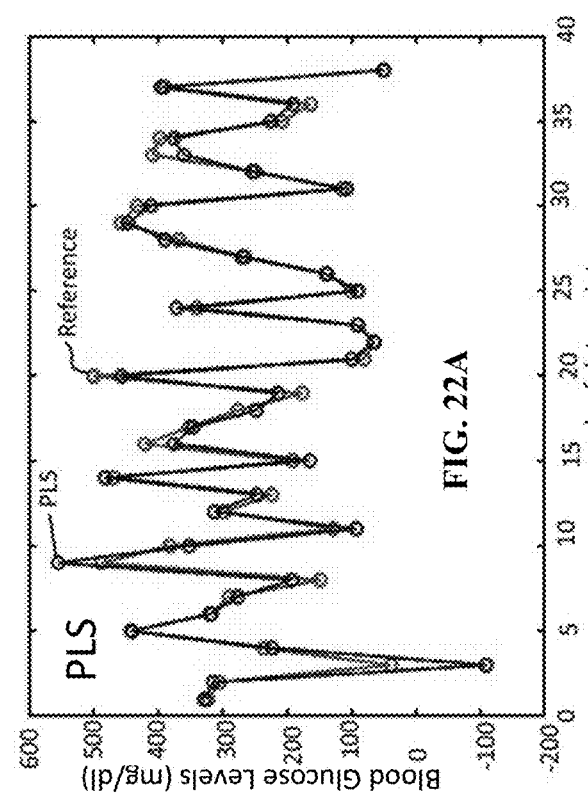
Figure 22D:
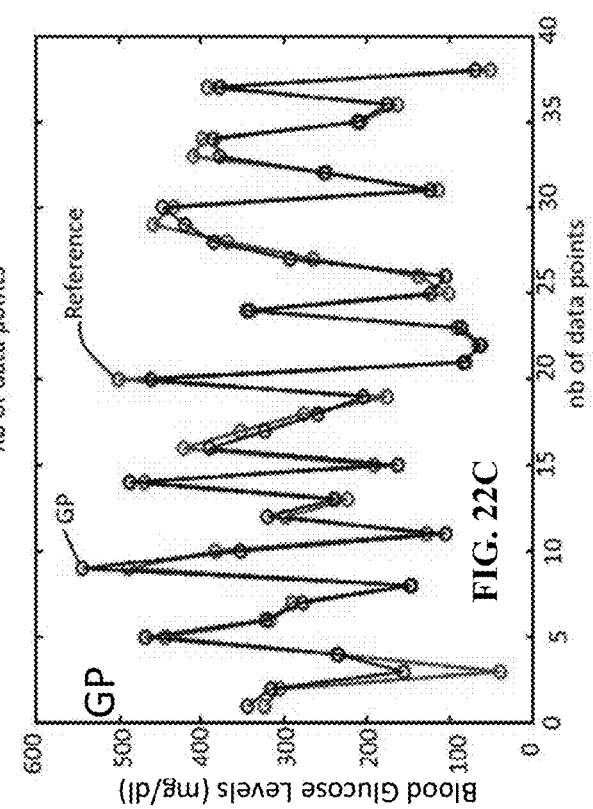
Figure 23A:
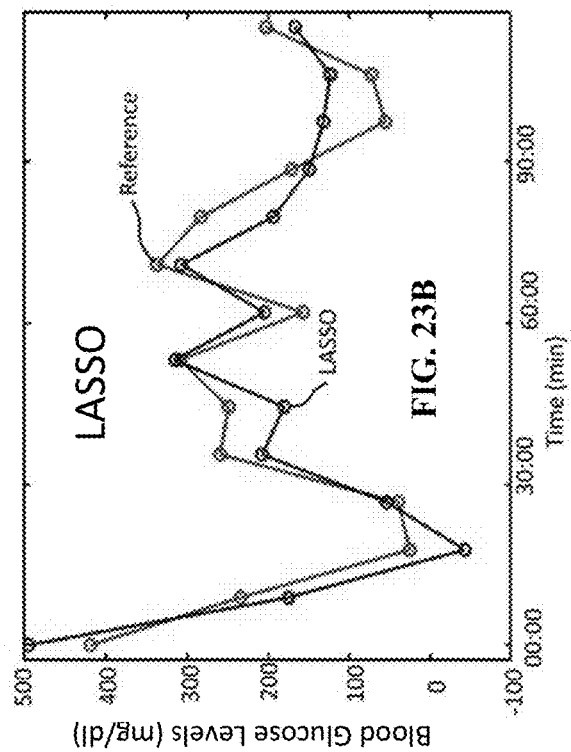
FIGS. 23A-23D are graphs showing the data is split into (⅔) training and (⅓) testing: showing test data for the rigid antenna.
Figure 23B:
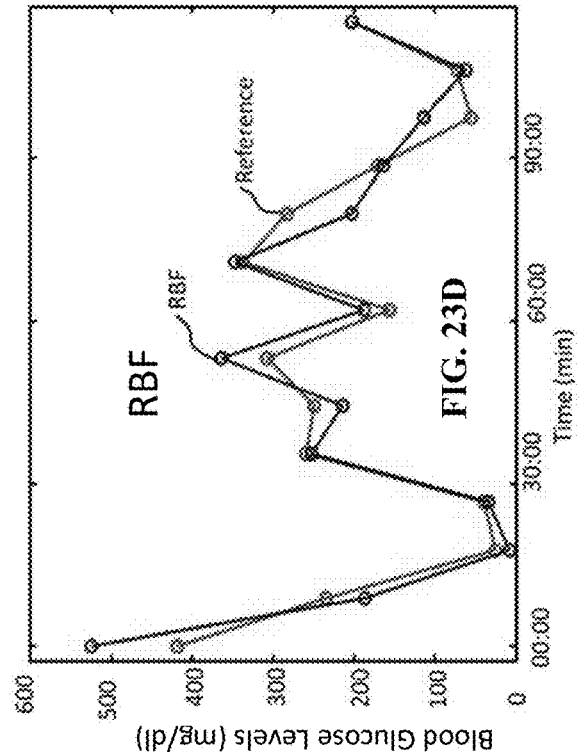
Figure 23C:
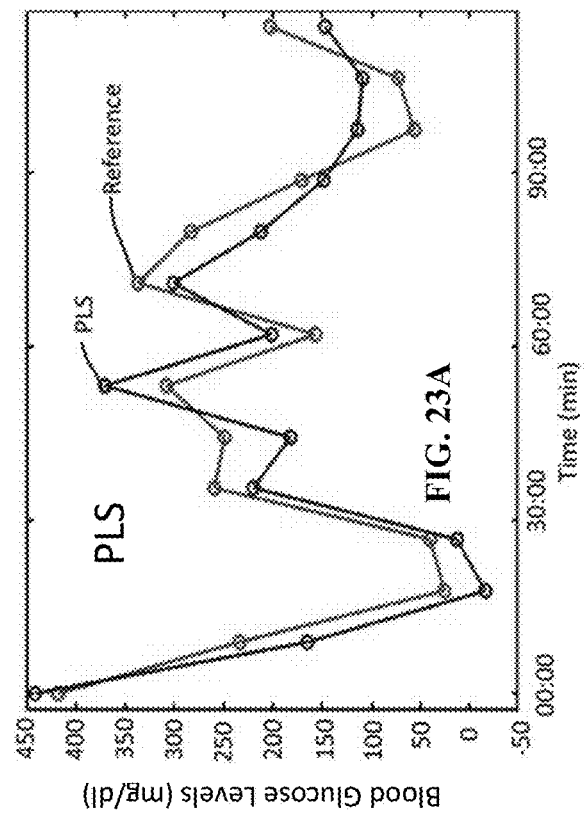
Figure 23D:
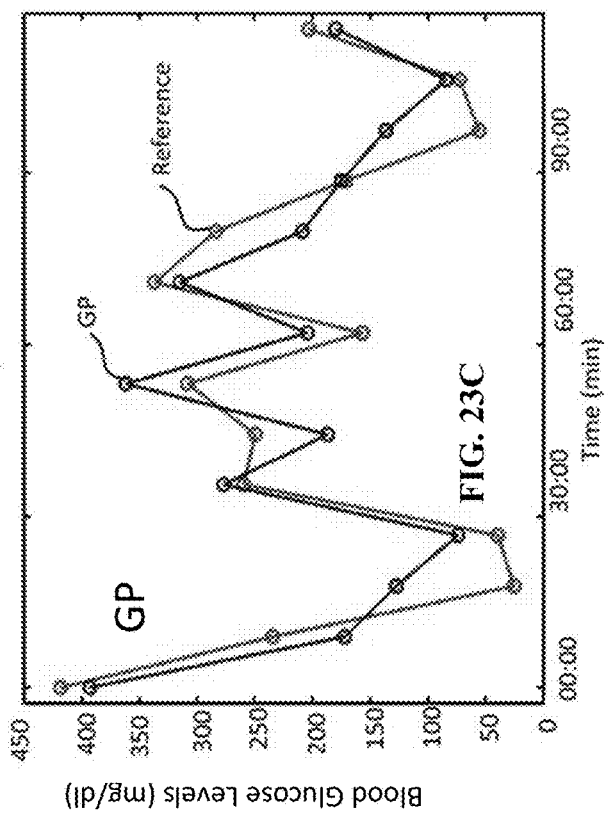
Figure 24A:
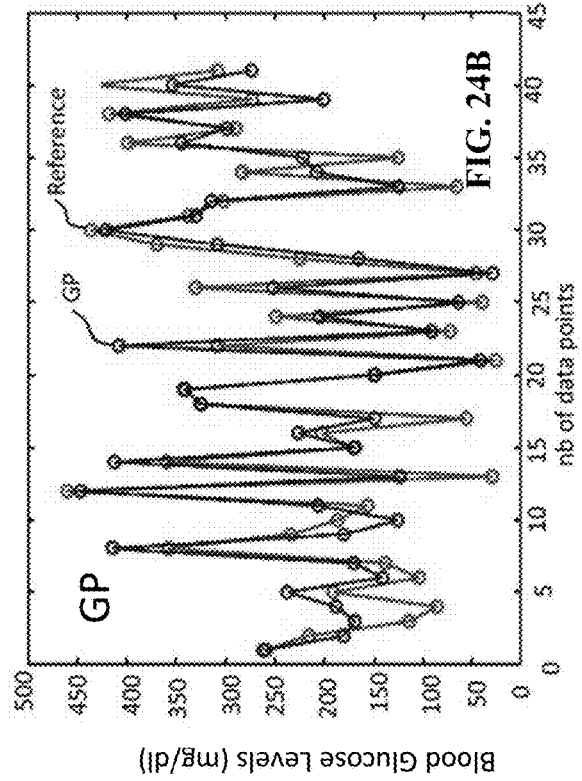
FIGS. 24A-24D are graphs showing the rigid antenna when one is left out for the rigid antennae: each point is considered a test point, and the remaining points are used to build the model.
Figure 24B:
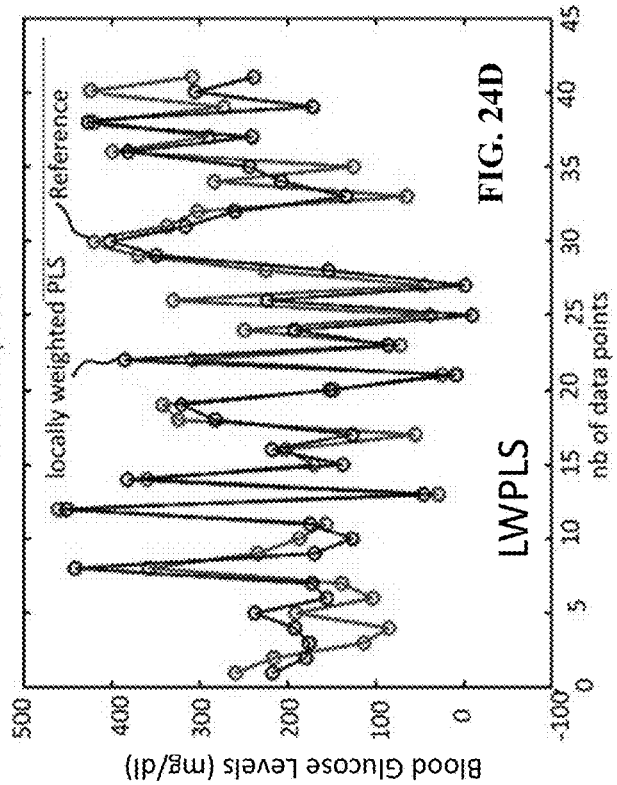
Figure 24C:
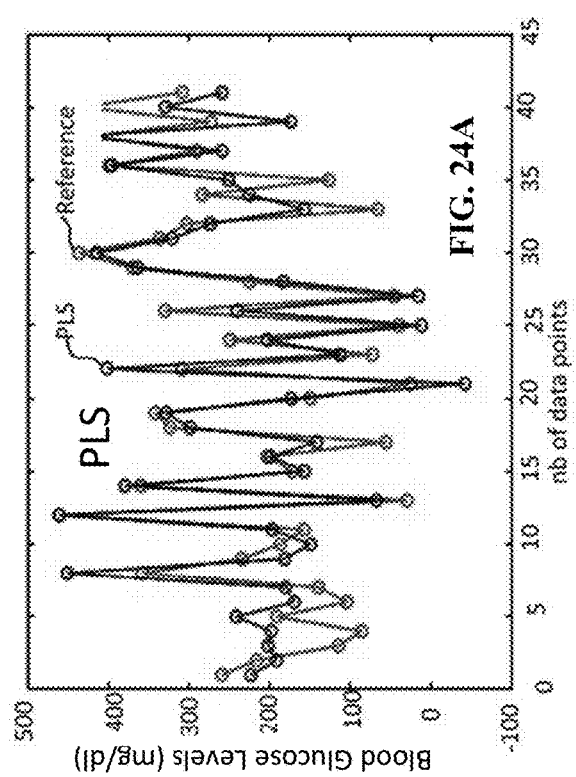
Figure 24D:
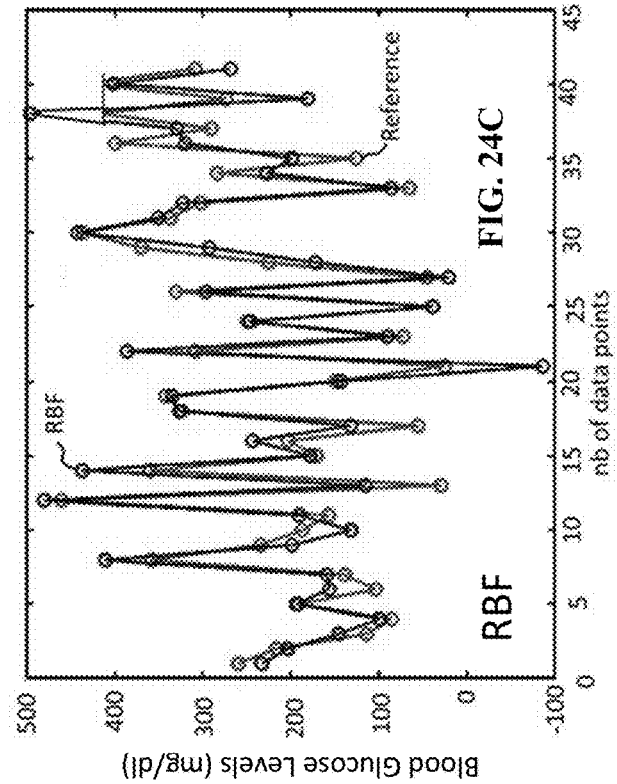

FIGS. 21A-21C are graphs of the estimated glucose level values, when the data is split into ⅔ training and ⅓ testing for the flexible antenna embodiment and the PLS, GP, and RBF modeling techniques.

FIGS. 22A-22D are graphs showing when one is left Out: where each point is considered a test point, and the remaining points are used to build the model for the PLS, GP, and RBF modeling techniques.

FIGS. 23A-23D are graphs showing the data is split into (⅔) training and (⅓) testing: showing test data for the rigid antenna for the PLS, LASSO, GP, and RBF modeling techniques.

FIGS. 24A-24D are graphs showing the rigid antenna when one is left out for the rigid antennae: each point is considered a test point, and the remaining points are used to build the model for the PLS, GP, RBF, and LW PLS modeling techniques.

Example 2: Sensitivity Test

Figure 25B:
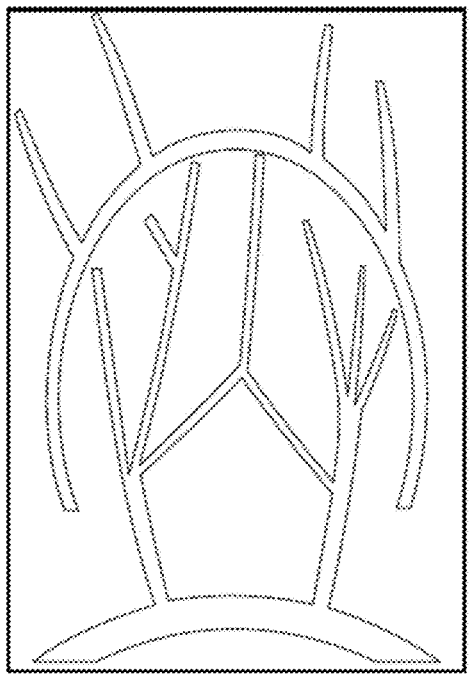
FIG. 25B is top view of the antenna for the experiment 1.
Figure 25D:
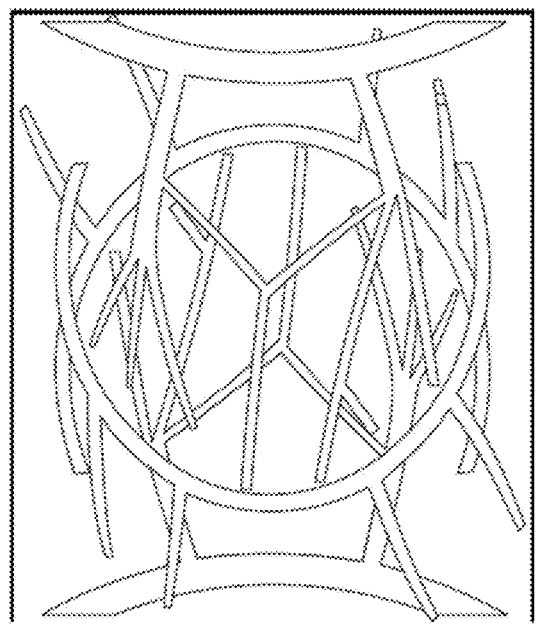
FIG. 25D is a top view of the antenna for the experiment 2.
Figure 25A:
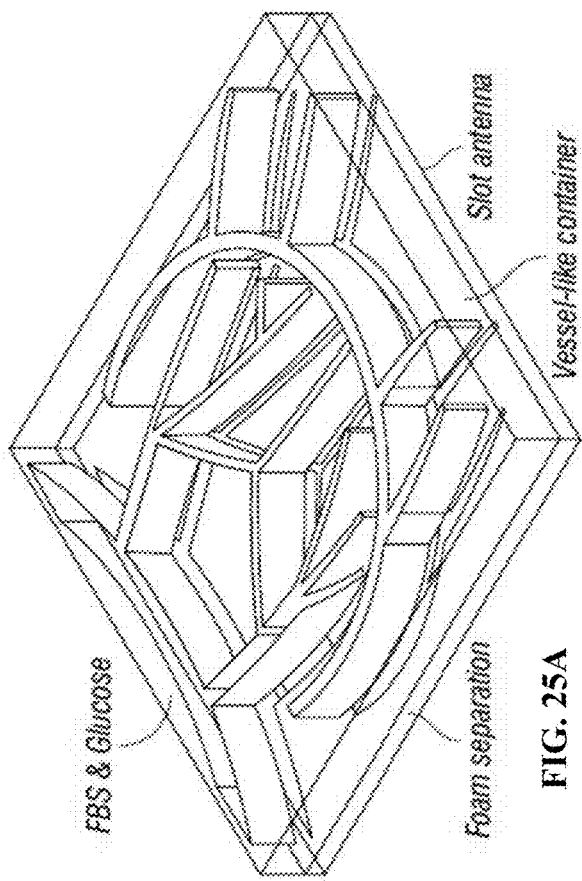
FIG. 25A is a perspective view of the schematic for experiment 1.
Figure 25C:
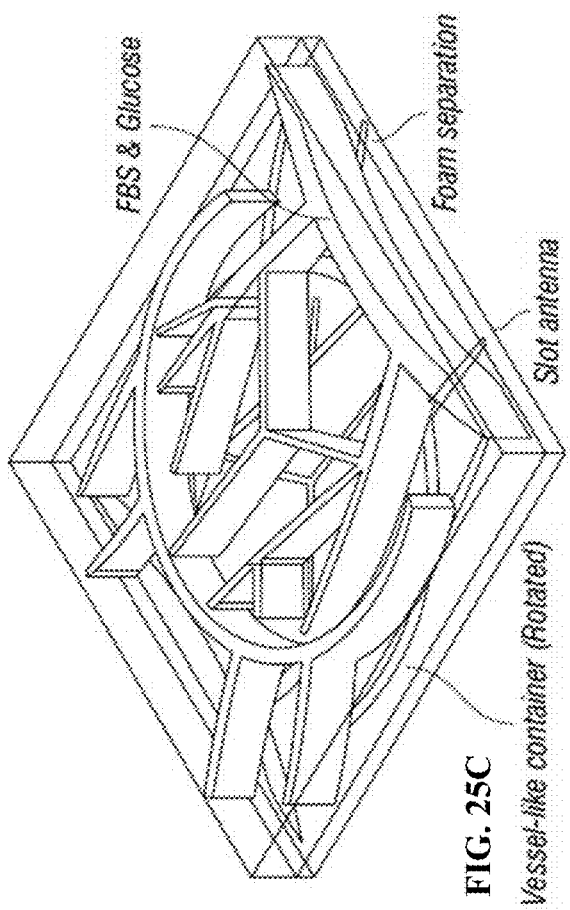
FIG. 25C is a perspective view of the schematic for Experiment 2.

FIG. 25A is the experiment 1 setup and FIG. 25B is top view of the antenna for the experiment 1. A vessel like container made of foam is filled with 14 ml of FBS. Two experiments were conducted to prove the importance of concentrating the EM waves on the veins. As shown in FIG. 25A, the vessel-like container, filled with FBS, is positioned parallel to the antenna's slots, as shown in FIG. 25B. Experiment 2, as shown in FIG. 25C, the antenna is shown in FIG. 25D and is fixed (same position as the previous experiment) and the vessel-like container rotated 180°.

An initial measurement is done. A reference glucose level is taken using the Glucotrack glucometer from Roche. 10 savings for the S11 magnitude and phase are taken using the VNA. After each measurement a small amount of glucose, equivalent to 100 mg/dl, is added to the FBS solutions. After each addition of glucose, the FBS solution is mixed and left for 10 minutes to insure the homogeneity of the solution. The same procedure is repeated until the glucose levels of the FBS reaches around 500 mg/dl. This experiment is done using the rigid antenna: A total of 7 data points were collected in both experiments The S11 variation Vs the Glucose level at the freqs giving the best correlation between the S11 and the Ref glucose. Parallel, as shown in FIG. 26A includes a Magnitude: 0.625 GHz with r=0.9963, and a Phase: 2.06 Ghz with r=0.9973. Rotated, as shown in FIG. 26B includes a Magnitude: 0.7 GHz with r=0.9852, and a Phase: 1.89 GHz with r=0.9234.

Figure 26B:
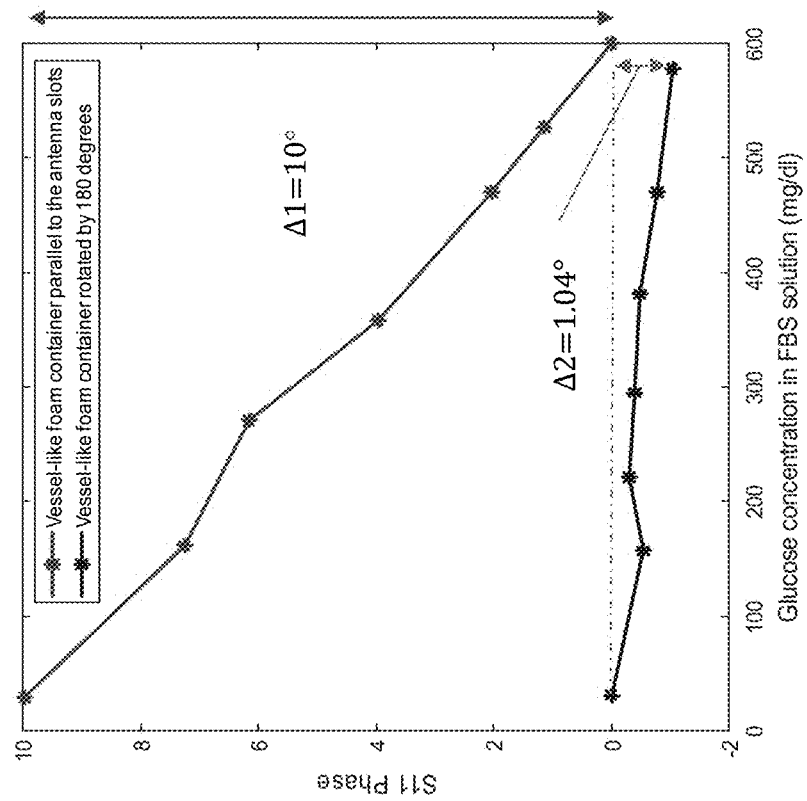
FIG. 26B is graph showing the Rotated.
Figure 26A:
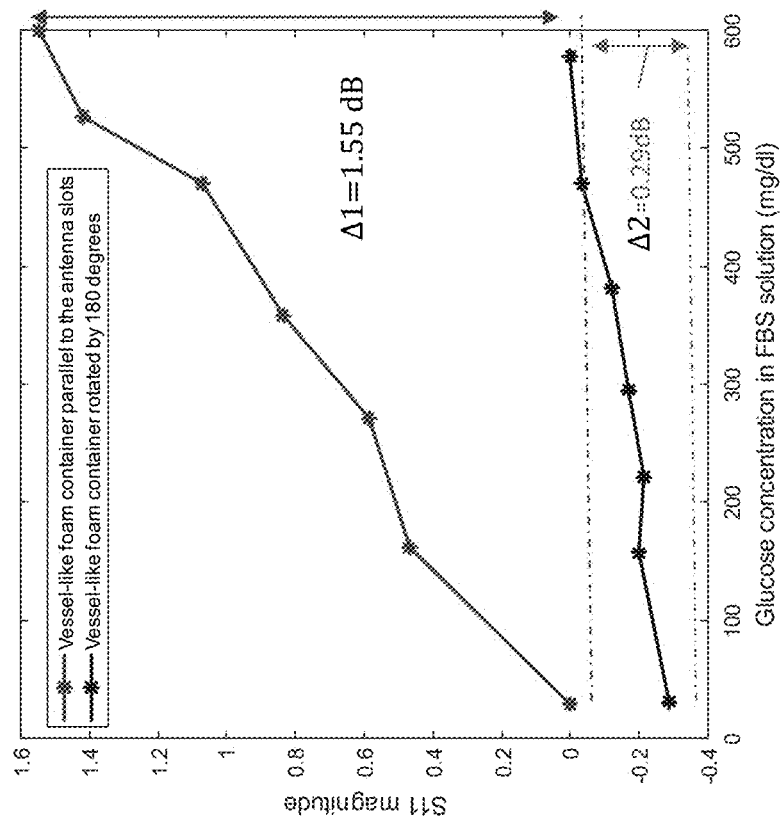
FIG. 26A is a graph showing the S11 variation Vs the Glucose level at the freqs giving the best correlation between the S11 and the Ref glucose for the Parallel.

FIGS. 26A-26B shows the importance of the blood vessels inspired slots. The FBS-glucose solution is filled inside a vessel-like container. FIGS. 25A-25B shows the antenna is placed parallel to the vessel-like container, superposing the slots of the antenna upon that of the container (configuration 1). FIGS. 25C-25D: the vessel-like container is left in the same position as in FIG. 25A and the antenna is rotated with a 180° (configuration 2). FIGS. 26A-26B shows the comparison between the antenna's response (S11) versus the reference glucose levels obtained from the two configurations. The S11 magnitude and phase in both experiments corresponds the frequencies achieving the highest correlation between the S11 parameters and the reference glucose levels. S11 versus the reference glucose levels obtained using the configuration 2 (red) and using configuration 2 (blue). FIG. 26A shows S11 magnitude, showing a total change of 1.55 dB in configuration 1 and 0.29 dB in configuration 2 for glucose levels ranging from 10 to around 600 mg/dl. Right: S11 phase, showing a total change of 10 degrees in configuration 1 and 1.04 degrees in configuration 2.

Example 3: Ex-Vivo Experiment on Rat Skin

Figures 27A, 27B:
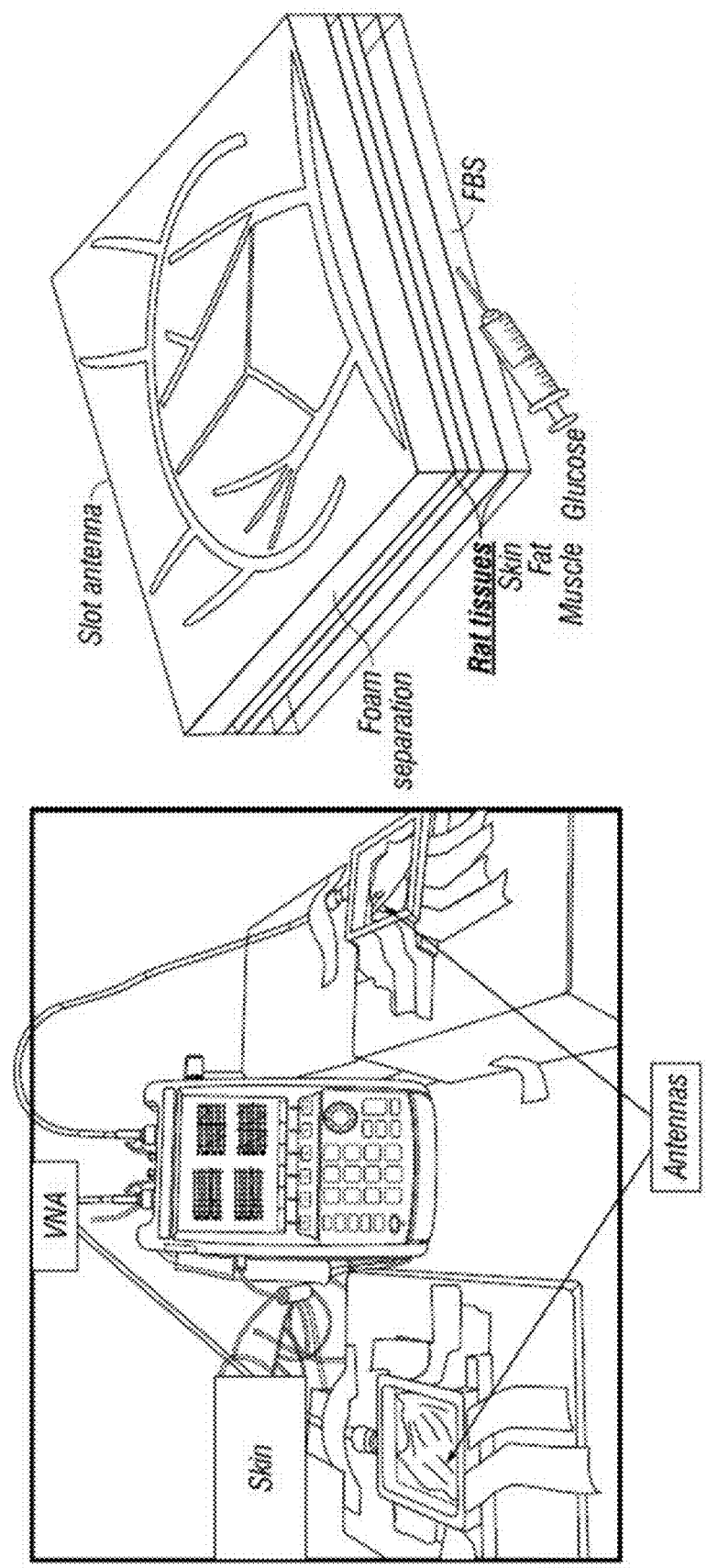
FIG. 27A is a schematic Experimental Set-up for the ex-vivo experiment.
FIG. 27B is a photo showing the experimental setup for the Ex-vivo experiments using the flexible antenna and Ex-vivo experiment covering the hypo- to hyper-glycemic range. The skin and the FBS layers are separated by a thin nylon sheet and the glucose levels of the FBS solution is varied from the hypo to the hyper glycemic levels (ranging between 10 to 500 mg/dl).

Experimental Set-up is shown in FIG. 27A. Fresh abdominal rat skin is dissected and cut into a 70 by 70 mm and preserved in Phosphate-buffered saline (PBS) solution. The skin with the PBS is paced in a foam container. Foam dimension: same size of the antenna (70*70 mm) and a thickness of 0.5 cm. The container is kept fixed during the whole experiment. A thin nylon container is filled with 14 ml of Fatal Bovine Serum FBS/glucose solutions which is very close to the blood in terms of composition. An initial measurement is done and a reference glucose level is taken using the Glucotrack glucometer from Roche. 10 savings for the S11 magnitude and phase are taken using the VNA.

Figure 28A:
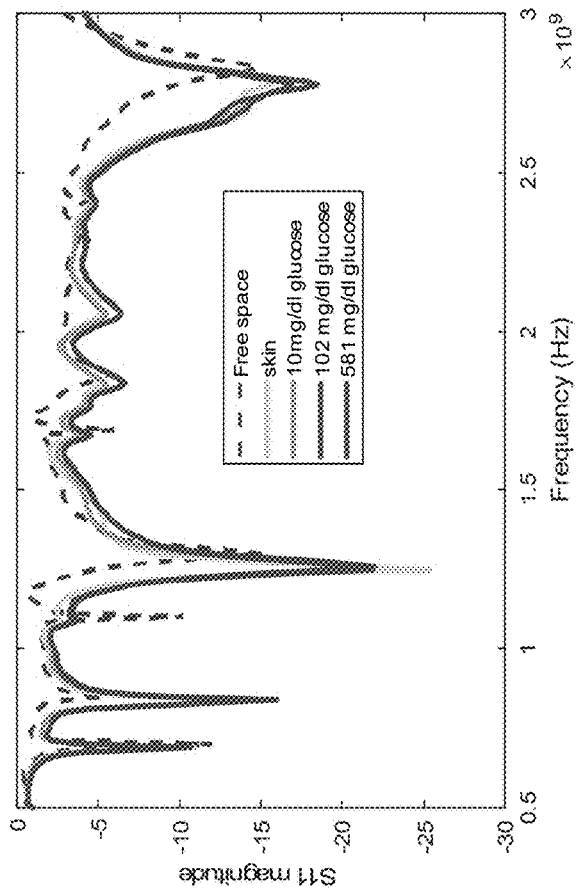
FIGS. 28A and 28B are graphs showing the effect of the skin on the S11 response for both rigid and flexible antennas, respectively.
Figure 28B:
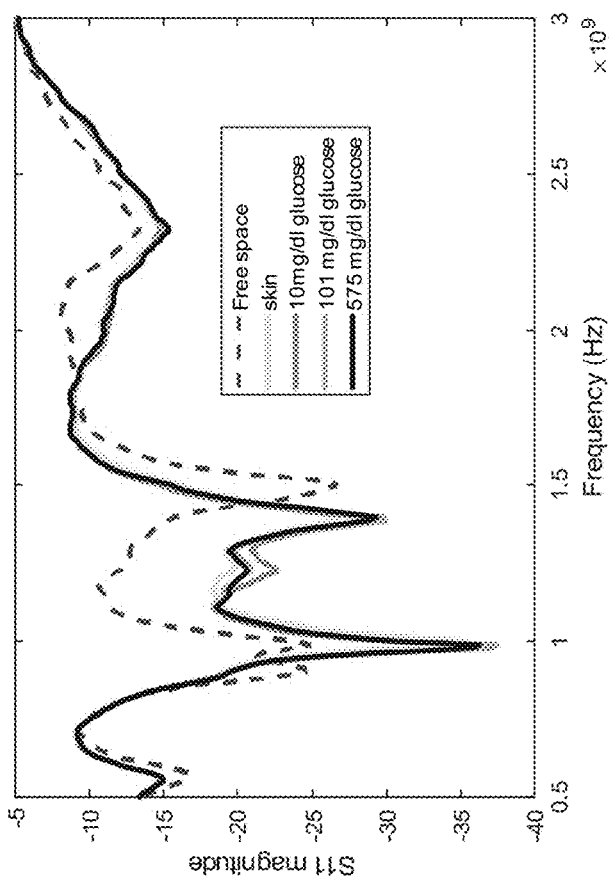

After each measurement a small amount of glucose, equivalent to 100 mg/dl, is added to the FBS solutions. After each addition of glucose, the FBS solution is mixed and left for 10 minutes to insure the homogeneity of the solution. The same procedure is repeated until the glucose levels of the FBS reaches around 500 mg/dl. Same experiment is done on both antennas: A total of measurements of 14 were taken for the rigid antenna and from the flexible one. The effect of the skin on the S11 response for both rigid and flexible antenna embodiments is shown in FIGS. 28A and 28B. The antennas are both operational (S11 below −6 dB) when loaded with a lossy medium (the skin). The flexible antennae results are shown in FIGS. 29A-29D.

Figure 28C:
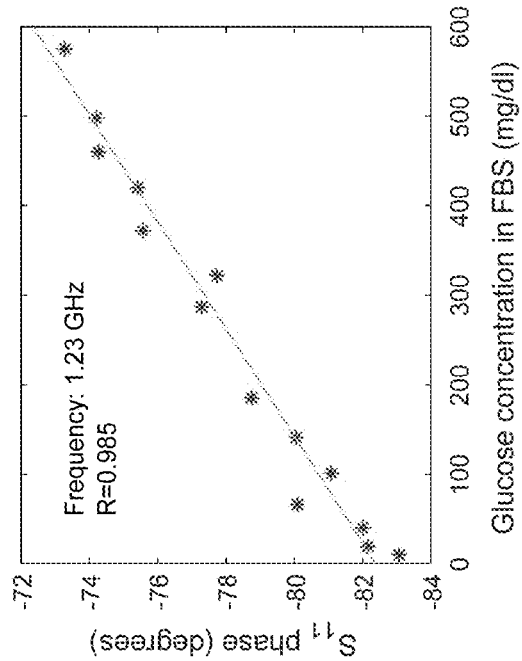
FIG. 28C is a graph of the Ex-vivo experiments using the flexible antenna and Ex-vivo experiment covering the hypo- to hyper-glycemic range showing the S11 magnitude response of the flexible antenna vs frequency. The S11 magnitude response shows good matching of the antenna when the skin (lossy medium) is placed in proximity to the antenna. Examples of the S11 magnitude responses corresponding to multiple glucose levels.
Figure 28D:
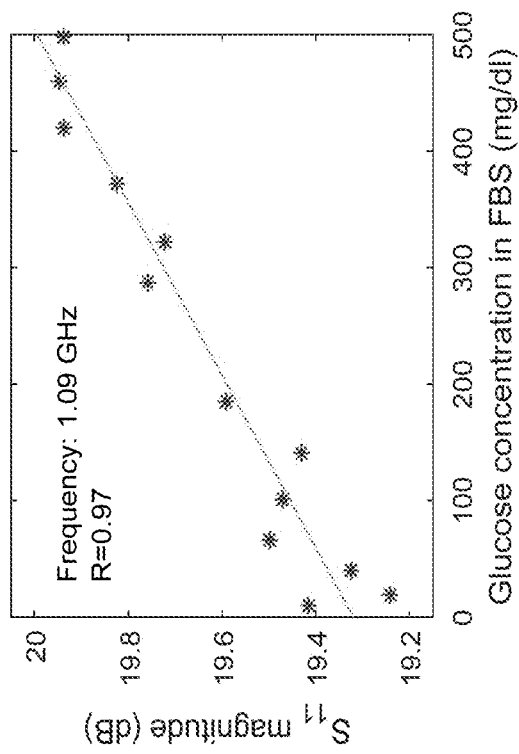
FIG. 28D is a graph showing the example of the S11 phase response versus glucose levels.

Ex-vivo experiments using the flexible antenna. Ex-vivo experiment covering the hypo- to hyper-glycemic range. FIG. 27B, The experimental setup. The skin and the FBS layers are separated by a thin nylon sheet and the glucose levels of the FBS solution is varied from the hypo to the hyper glycemic levels (ranging between 10 to 500 mg/dl). FIG. 28C-28D, Flexible antenna's response. FIG. 28C shows the S11 magnitude response of the flexible antenna vs frequency. The S11 magnitude response shows good matching of the antenna when the skin (lossy medium) is placed in proximity to the antenna. Examples of the S11 magnitude responses corresponding to multiple glucose levels. FIG. 28C shows the S11 magnitude versus the reference glucose levels obtained by the commercial invasive glucometer, showing a good correlation between the two curves (r=0.97). FIG. 28D shows the Example of the S11 phase response versus glucose levels. Great correlation between the S11 phase and the reference glucose levels (r=0.98).

Example 3: In Vivo Experiment on Rats

Figure 30:
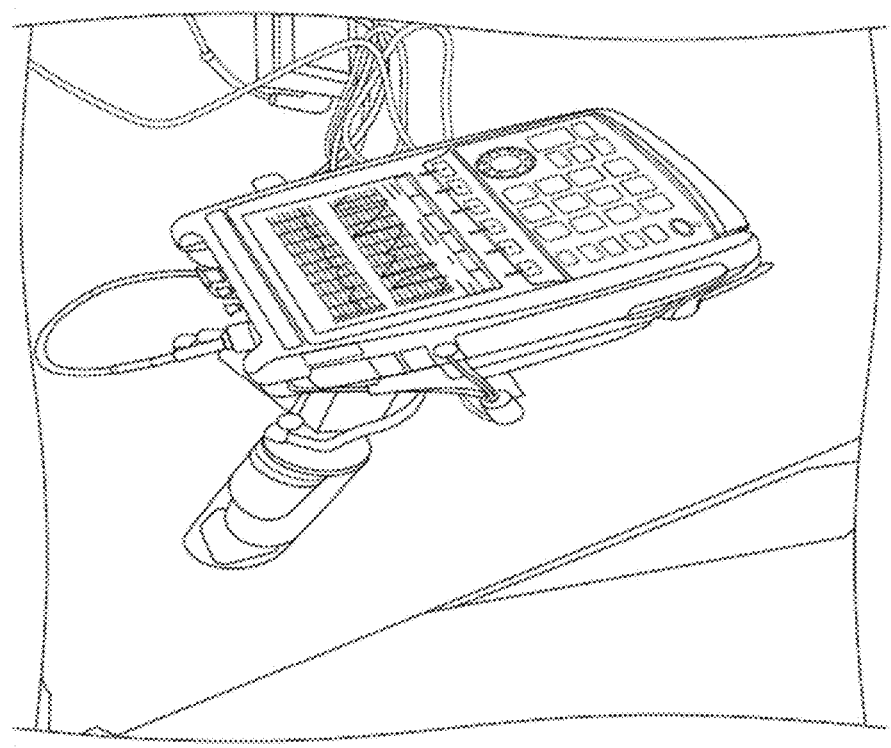
FIG. 30 is a schematic diagram of the in vivo experimental.

Experimental Setup is shown in FIG. 30. Rat species: Sprague Dawley rats The animals were housed in the Animal Care Facility of the American University of Beirut, in rack-mounted wire cages, with a maximum of 5 rats per cage and kept on a 12 hours light/dark cycle in a controlled temperature and humidity room. Standard laboratory pelleted formula and tap water were provided ad libitum. The experiment was carried out in accordance to the guidelines of the Institutional Animal Care and Use Committee (IACUC) at the American University of Beirut" [1] [1] Gerges, Alice & Rizzo, M & Eid, Assaad & Hajj Hussein, Inaya & Zgheib, Z & N Zeenny, M & Jurjus, Rosalyn & Uzzo, Maria & Spatola, Giovanni & Bonaventura, Giuseppe & Leone, Angelo & Massaad-Massade, Liliane & Jurjus, Abdo. (2017). Tea catechins induce crosstalk between signaling pathways and stabilize mast cells in ulcerative colitis. Journal of biological regulators and homeostatic agents. 31. 865-877.

The animal weighed around 700 g. A rat is studied after 8-hour overnight fast. Thirty minutes prior to the testing, the rat is anesthetized using inhaled anesthetic, Forane. The rat is anesthetized just during the fixation of the antenna on his back, whereas during the experiment the rat is awake. The measurement area of the hairy mice is shaved prior to the placement of the antenna to avoid the influence of possible external factors on the measurements. The antenna is fixed on the back of the rat with a foam separation of 0.5 cm and connected to the portable VNA. The animal is than placed in a restrainer in order to limit his movement during the experiment An Intraperitoneal injection glucose tolerance test (IP-GTT) is conducted. At time 0, the rat receives an intraperitoneal injection of 0.2 ml of saturated glucose solution. Measurements using both the VNA and a glucometer are done every 5 minutes. A reference glucose level using invasive glucometer, and for each measurement, 10 repeated readings for the S11 magnitude and phase are taken using the VNA. This is to average out any error resulting from the measurements. The S11 values were recorded over the whole desired frequency range.

Results—Rigid Antenna

Figure 31A:
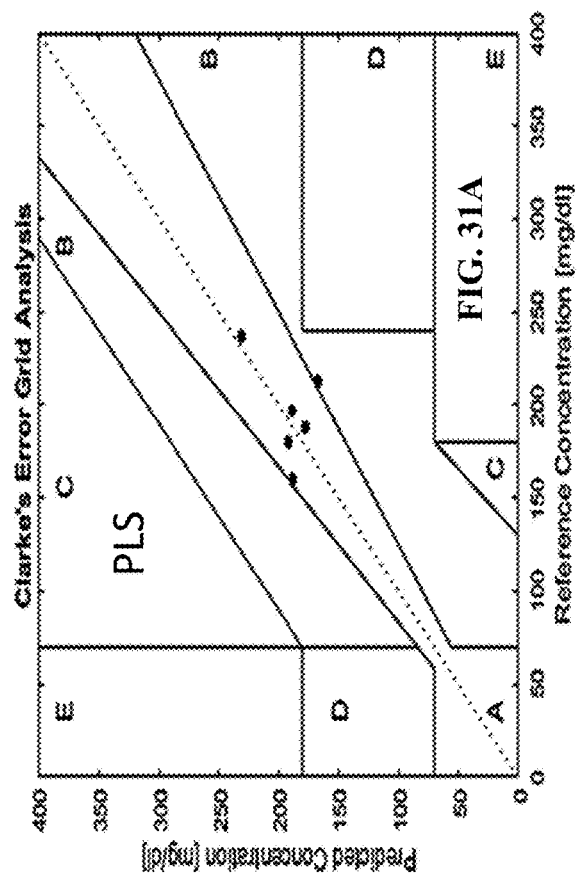
FIGS. 31A-31C are graphs showing the Clark's Error Grid Analysis for the split the data into (⅔) training and (⅓) testing.
Figure 31B:
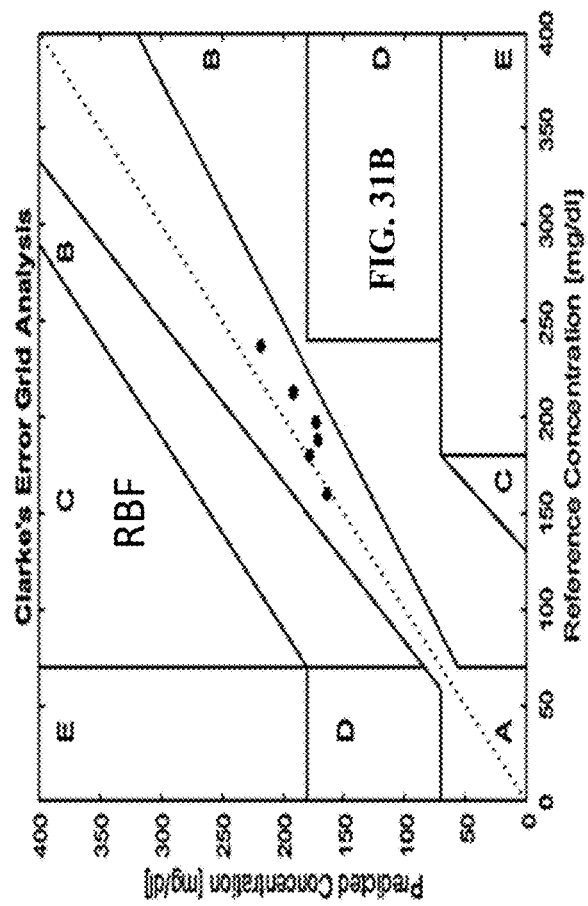
Figure 31C:
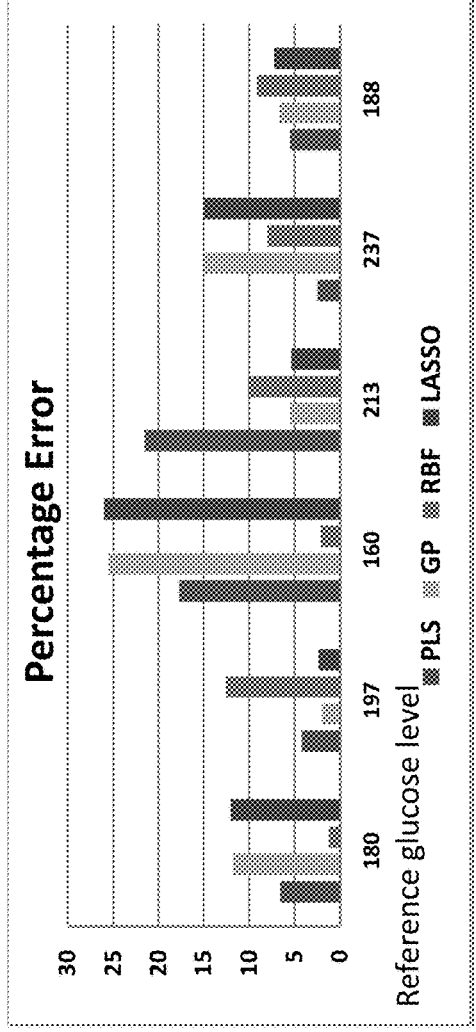

The data is split into (⅔) training and (⅓) testing: showing test data for the rigid antenna in the in vivo experiment on the rat in FIGS. 31A-31B for the PLS and RBF modeling techniques. FIG. 31C shows the percentage error for the PLS, GP, RBF, and LASSO modeling techniques for the reference glucose levels and Table 2.2 shows the percentage error for the PLS, GP, RBF, and LASSO modeling techniques in terms of the max, mean, and median data.

TABLE 2.2

| % Error | PLS | GP | RBF | LASSO |
|---|---|---|---|---|
| max | 21 | 25 | 12 | 26 |
| mean | 9 | 11 | 7 | 11 |
| median | 6 | 9 | 8 | 9 |

Figure 32C:
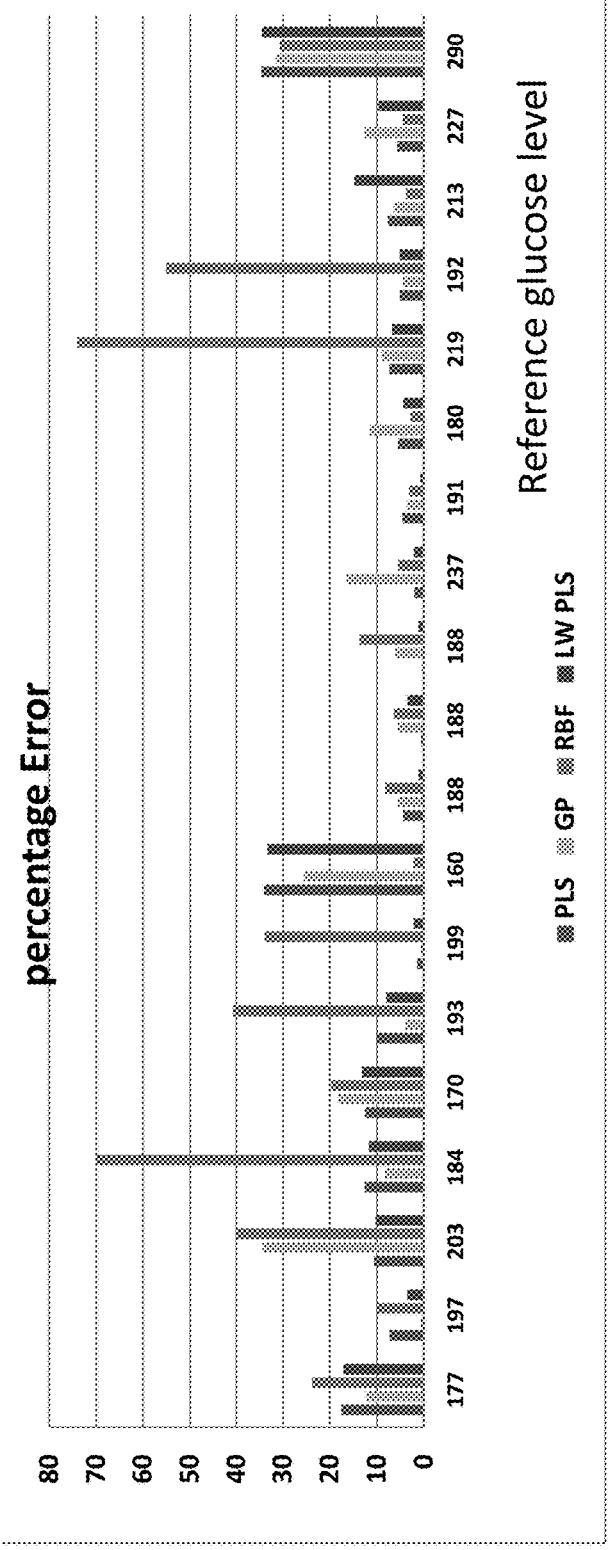
FIGS. 32A-32C are graphs showing the Clark's Error Grid Analysis for the Rigid Antenna results when Leave One Out.
Figure 32B:
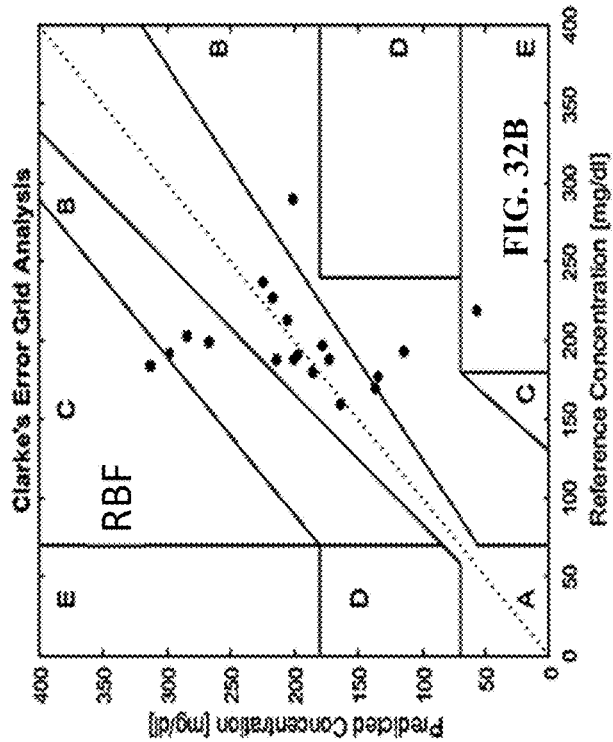
Figure 32A:
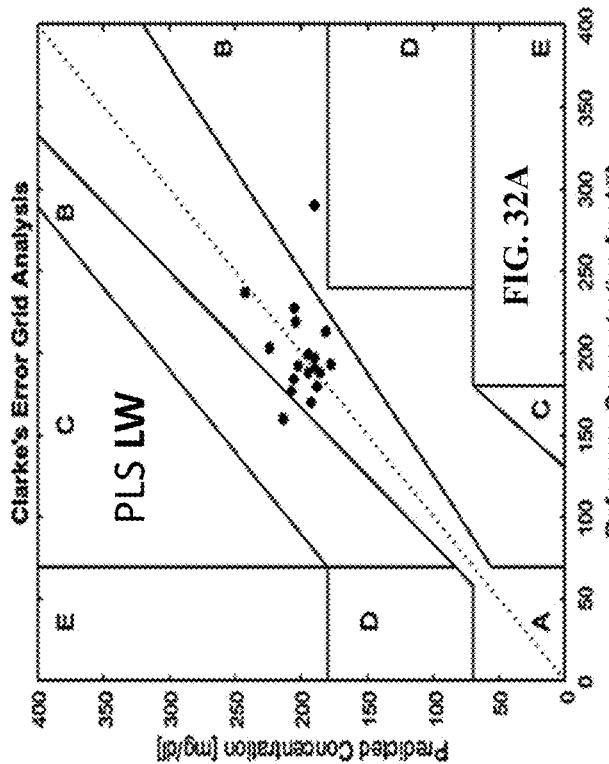

The Rigid Antenna results when Leave One Out is shown in FIGS. 32A-32B for the Clarke's Error Grid Analysis and the PLS LW and RBF modeling techniques. FIG. 31C shows the percentage error for the PLS GP, RBF, and LW PLS modeling techniques for the reference glucose levels and Table 3 shows the percentage error for the PLS GP, RBF, and LW PLS modeling techniques in terms of the max mean and median data.

TABLE 3

| % Error | PLS | GP | RBF | LW PLS |
|---|---|---|---|---|
| max | 34 | 34 | 74 | 34 |
| mean | 9 | 11 | 23 | 9 |
| median | 7 | 8 | 13 | 6 |

Example 3: In Vivo Experiment on Human Subjects

Figure 33:
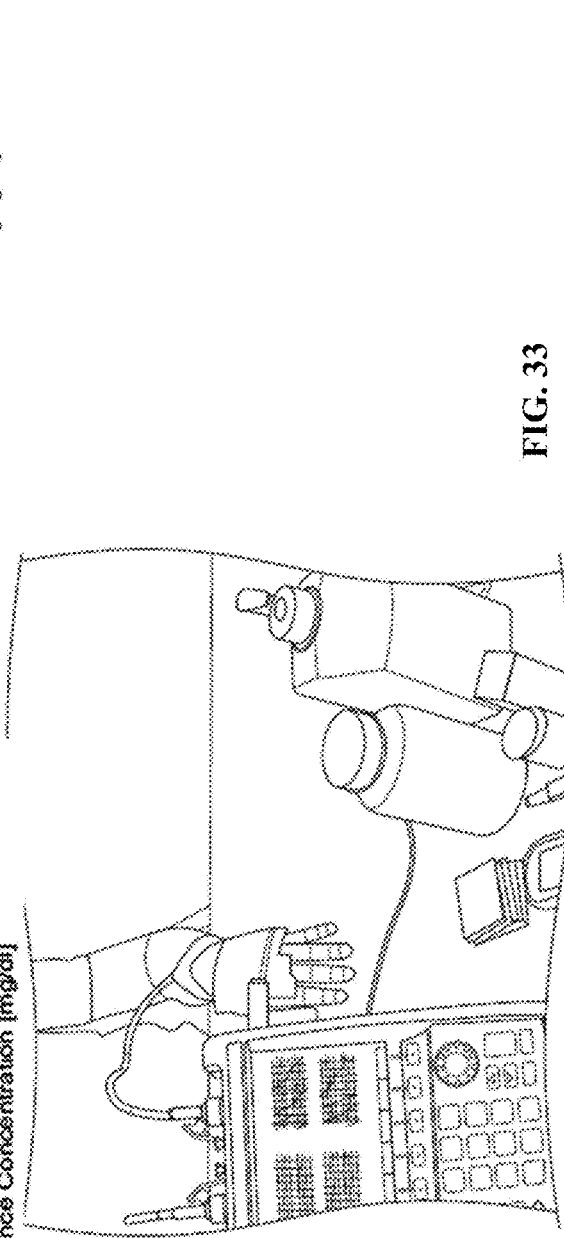
FIG. 33 is a schematic showing the experimental Setup on Controlled Healthy subjects.

FIG. 33 is a schematic showing the experimental Setup—on Controlled Healthy subjects. Before each visit, the subjects are asked not to eat or drink anything 8 hours before coming to the clinic.

1. Fixation of the sensing system: The subjects are asked to sit on a chair to limit the body movements. The rigid and the flexible antennas are placed on both hands and measurements will be taken simultaneously from both antennas. The antennas are fixed on the hands using Gauze Wrap and connected to a portable VNA. The antenna is not in contact directly on your skin, it will be separated by a 0.5 cm of foam.

2. Fasting glucose blood test: after the fixation of the sensing system, a first reference measurement is taken using an invasive glucometer and 10 savings from the VNA simultaneously.

3. Glucose intake: The subjects are asked to consume 75 grams of sugars by eating 500 ml of ice-cream in 10-15 minutes Glucose test: the same procedure described in step 3 (Fasting glucose blood test) is repeated every 15 minutes for two hours. VNA savings are taken every 5 minutes. The oral glucose tolerance test takes about 2 hours to be completed. Each subject repeats this procedure for a total of 3 times, on 3 different days. The data for a group of healthy individuals aging between 25 to 60 years old to take part is presented below. All the participants are from a healthy controlled group.

Results

Figure 34:
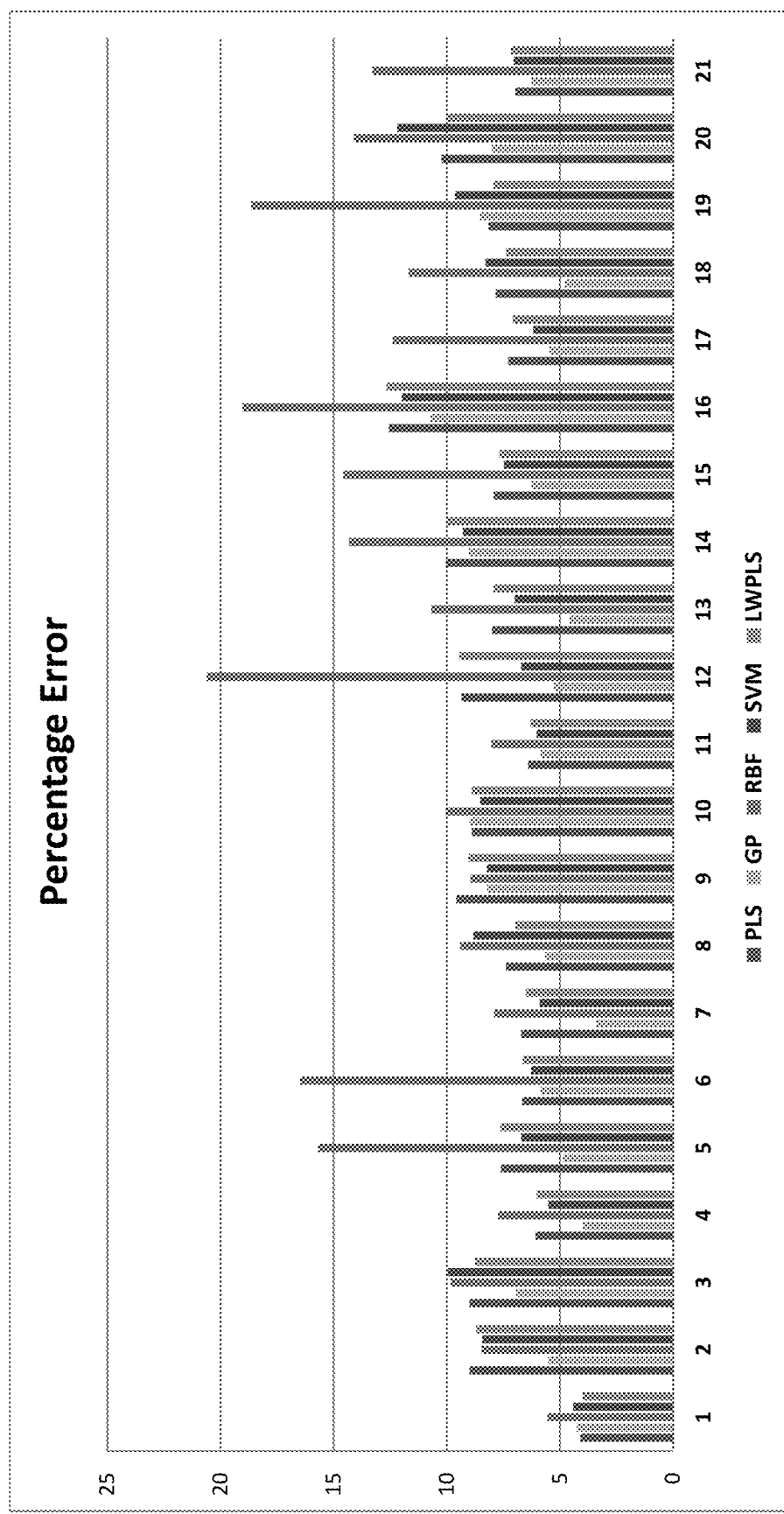
FIG. 34 is a graph for the in vivo experiment and Flexible Antenna: leave-one-out.

The graph for the Flexible Antenna showing the percentage error for the PLS, GP, RBF, SVM, and LW PLS modeling techniques: leave-one-out is shown in FIG. 34. Table 4 shows the mean percentage error for the PLS, GP, RBF, SVM, and LW PLS modeling techniques in terms of the mean, standard deviation, max, and min data points.

TABLE 4

Mean Percentage Error

|  | PLS | GP | RBF | SVM | LWPLS |
|---|---|---|---|---|---|
| mean | 8.08 | 6.31 | 12.26 | 7.84 | 7.94 |
| std | 1.79 | 1.93 | 4.18 | 2.02 | 1.80 |
| max | 12.56 | 10.71 | 20.61 | 12.18 | 12.66 |
| min | 4.09 | 3.41 | 5.55 | 4.41 | 4.00 |

Figure 35B:
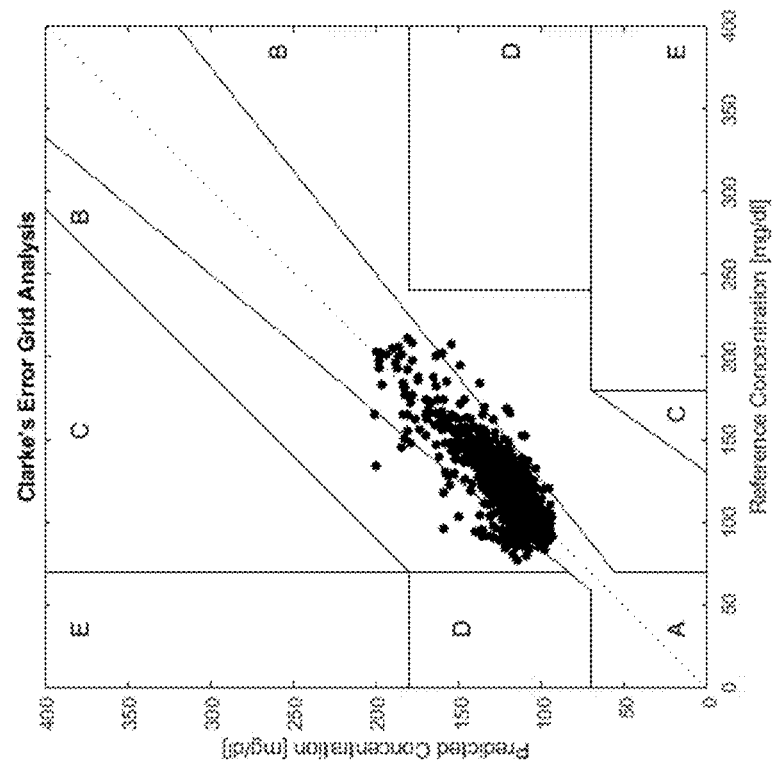
FIG. 35B is a graph of the Clark's Error Grid analysis for the Flexible Antenna: leave-one-out are
Figure 35A:
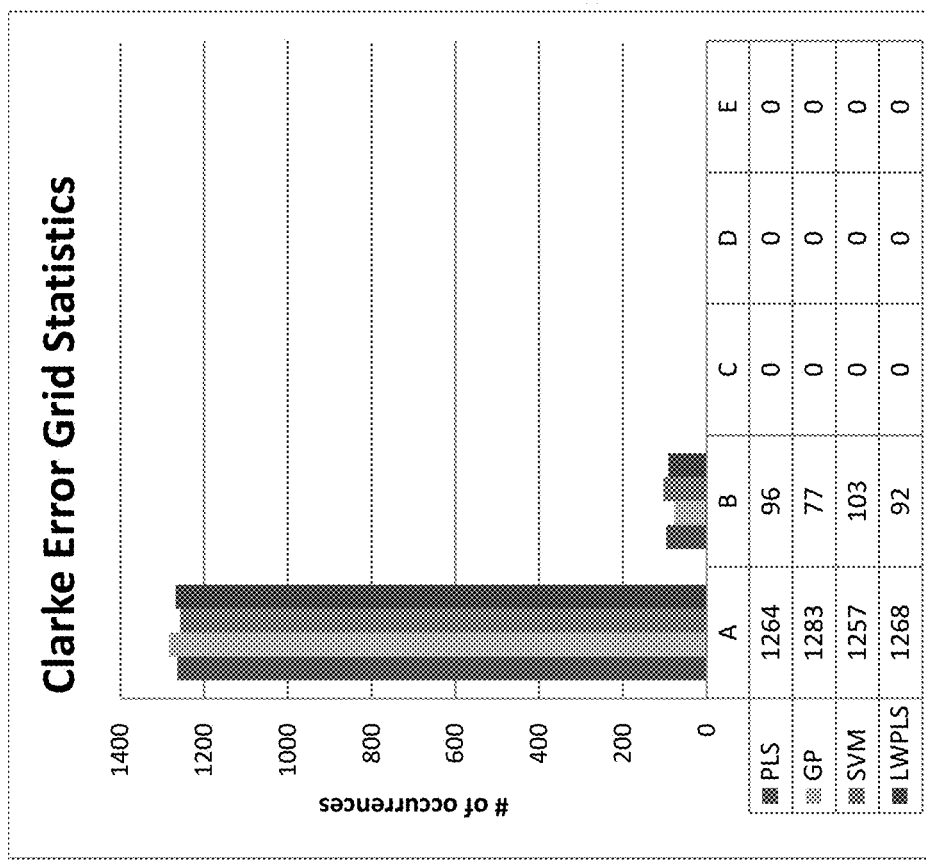
FIG. 35A is a graph of the Clark's Error Grid Statistics for the #of occurrences.
Figure 36B:
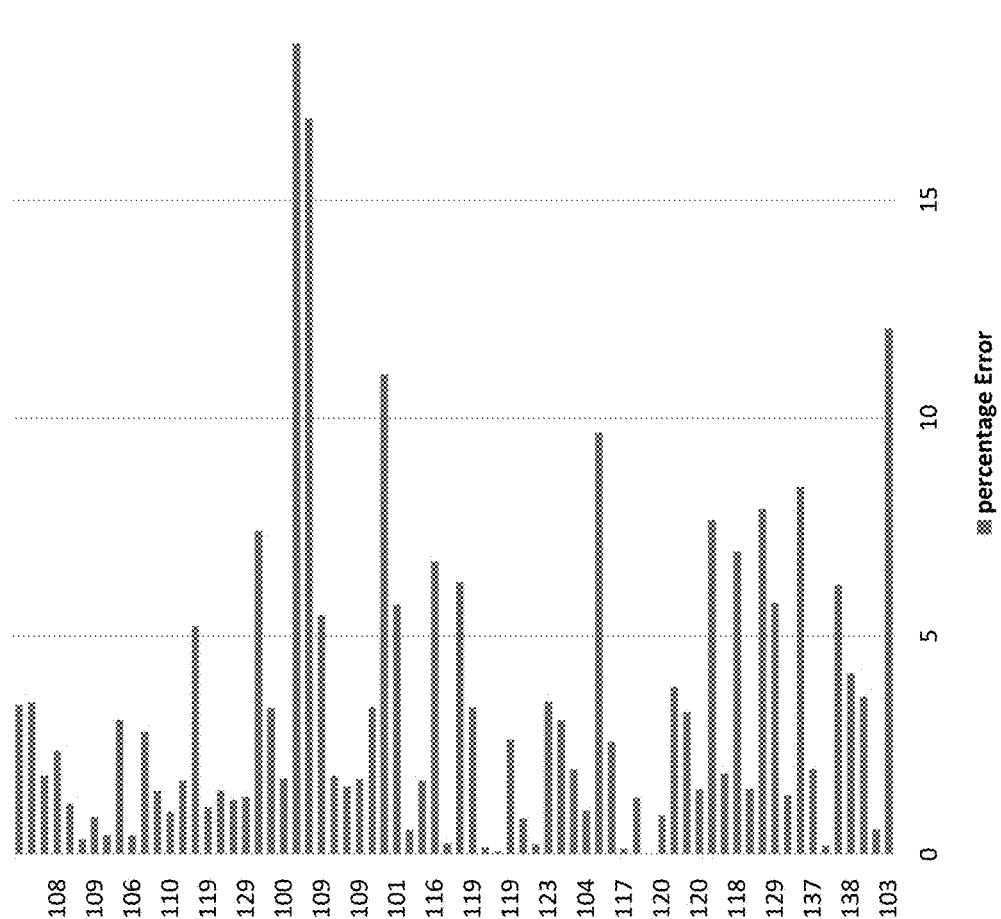
FIG. 36B is a bar graph showing the percentage error.
Figure 35C:
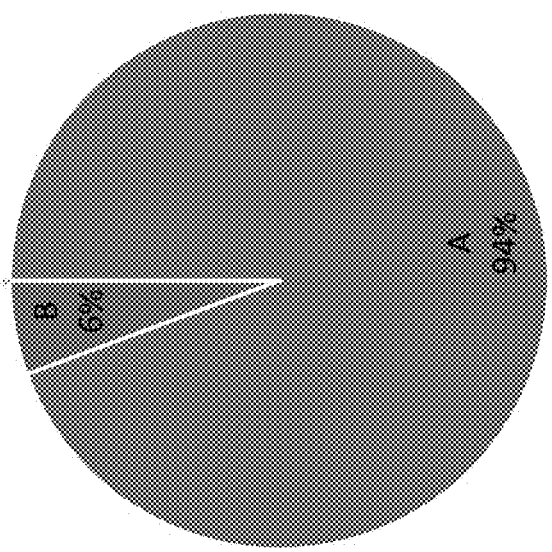
FIG. 35C is a pie graph showing that all results are in Zones A and B which are considered clinically acceptable.
Figure 36A:
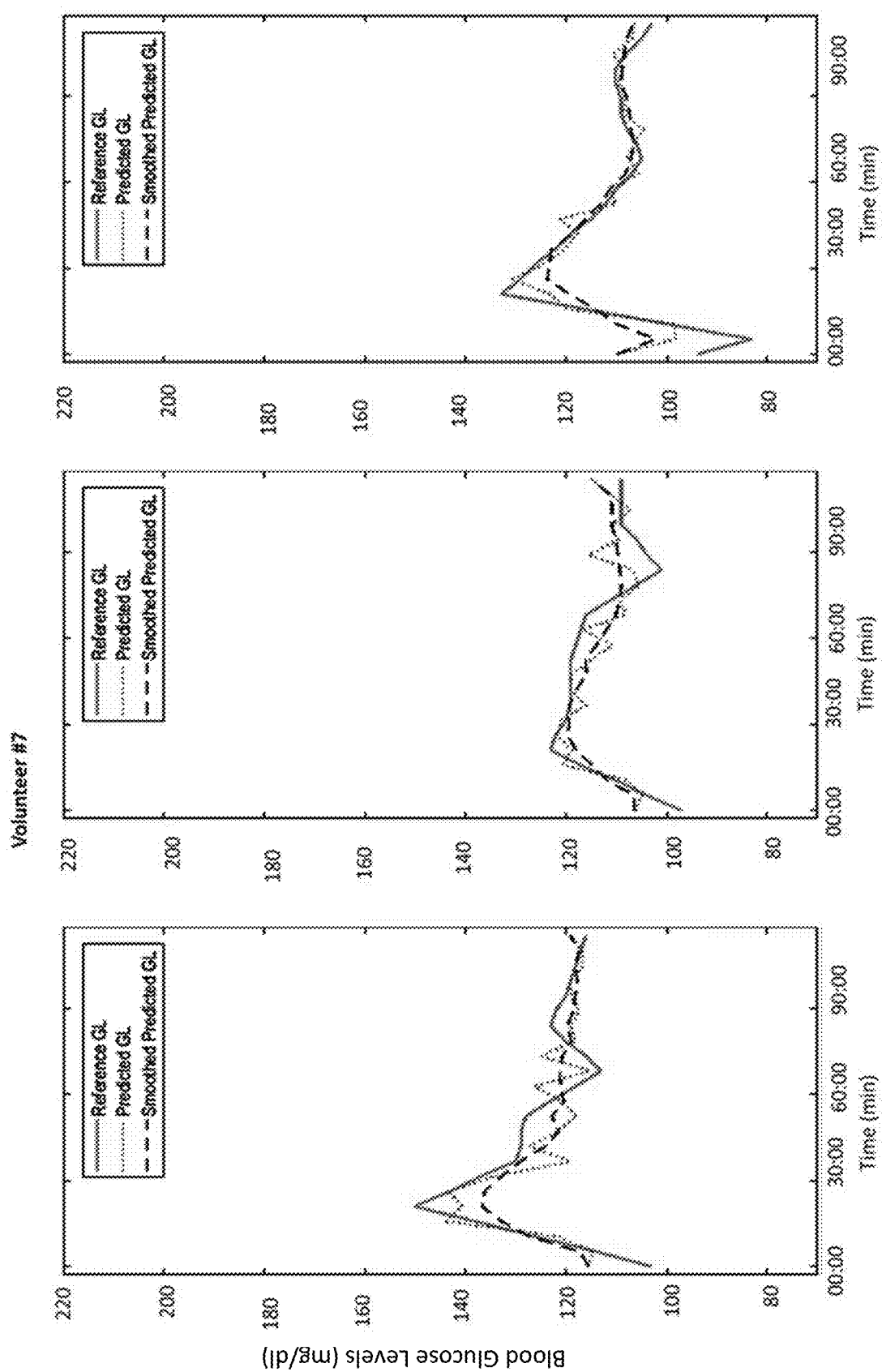
FIG. 36A is a graph showing the blood glucose levels for the Flexible Antenna: leave-one-out for Volunteer 7.

The in vivo experiment results for the Flexible Antenna and the Clark Error Grid statistics for the PLS, GP, SVM, and LW PLS models, Clark's Error Grid Analysis, and pie chart for: leave-one-out are shown in FIGS. 35A-35C. All results are in Zones A and B which are considered clinically acceptable The individual results for Volunteer #7 for the Flexible Antenna: leave-one-out is shown in FIG. 36A. FIG. 36B shows the percentage error for the blood glucose levels taken compared to the reference glucose levels.

Figure 37A:
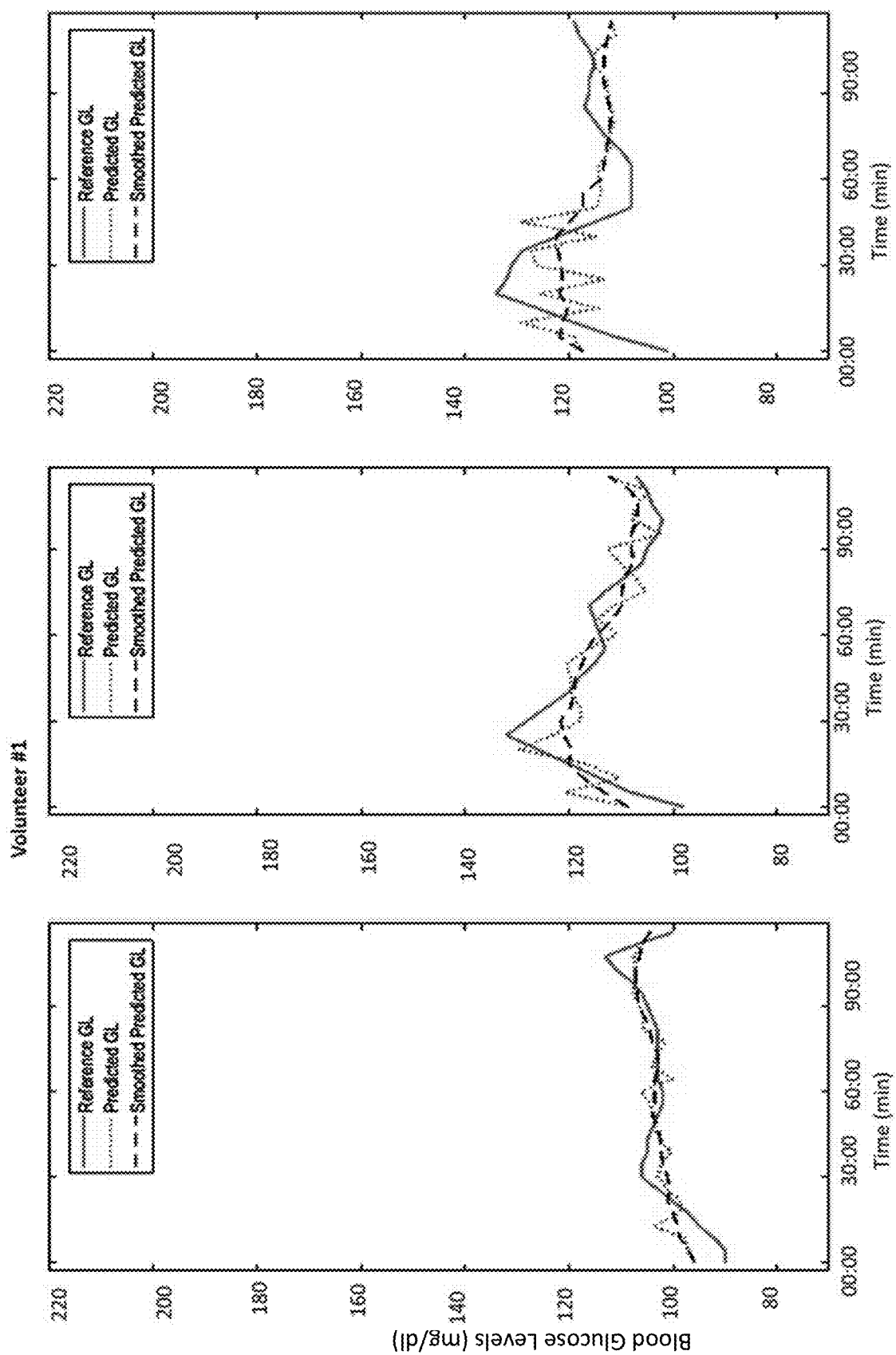
FIG. 37A is a graph showing the blood glucose levels for the Flexible Antenna: leave-one-out for Volunteer 1.

The individual results for Volunteer #1 for the Flexible Antenna: leave-one-out is shown in FIG. 37A. FIG. 37B shows the percentage error for the blood glucose levels taken compared to the reference glucose levels.

Figure 38A:
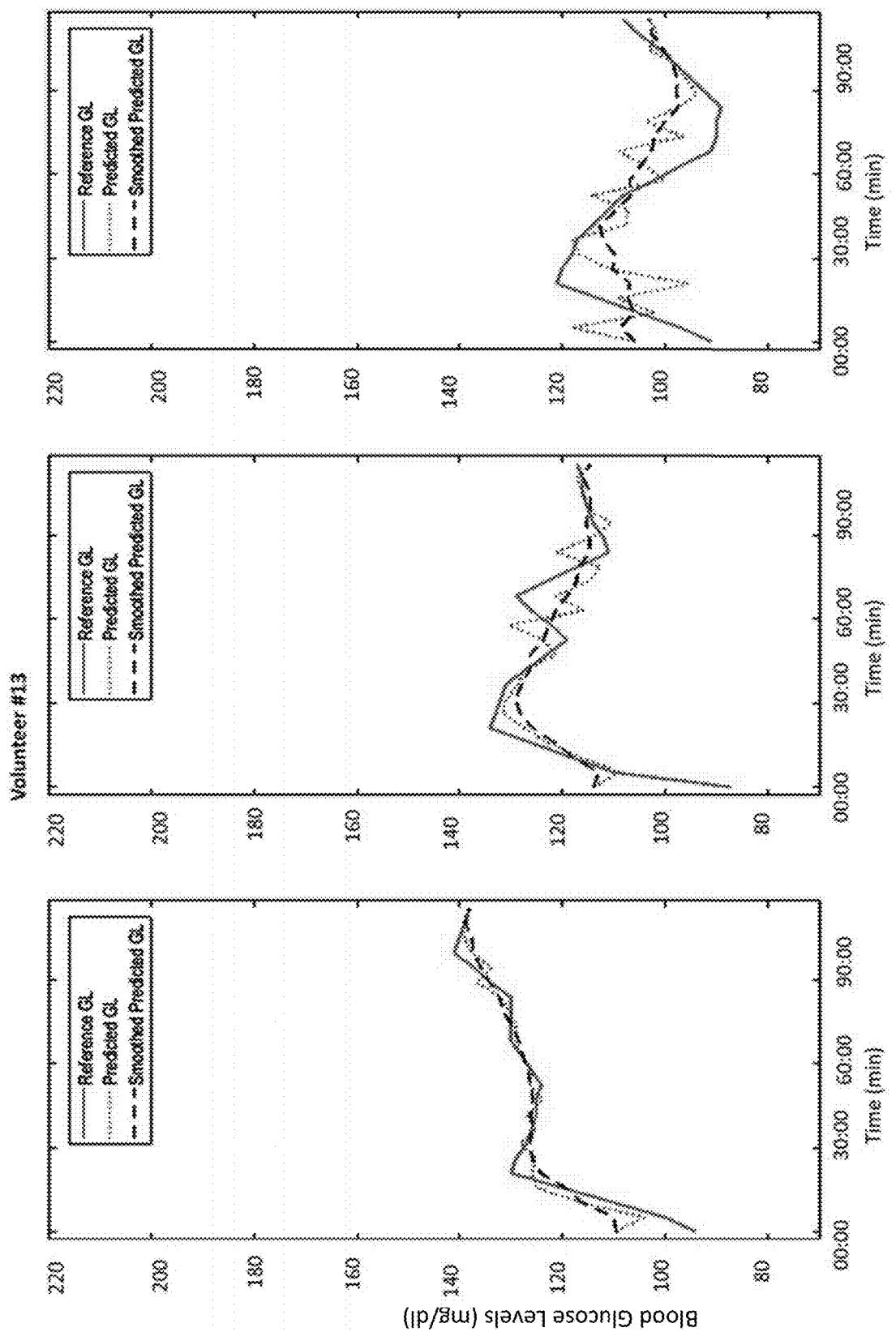
FIG. 38A is a graph showing the blood glucose levels for the Flexible Antenna: leave-one-out for Volunteer 13.

The individual results for Volunteer #13 for the Flexible Antenna: leave-one-out is shown in FIG. 38A. FIG. 38B shows the percentage error for the blood glucose levels taken compared to the reference glucose levels.

Figure 39A:
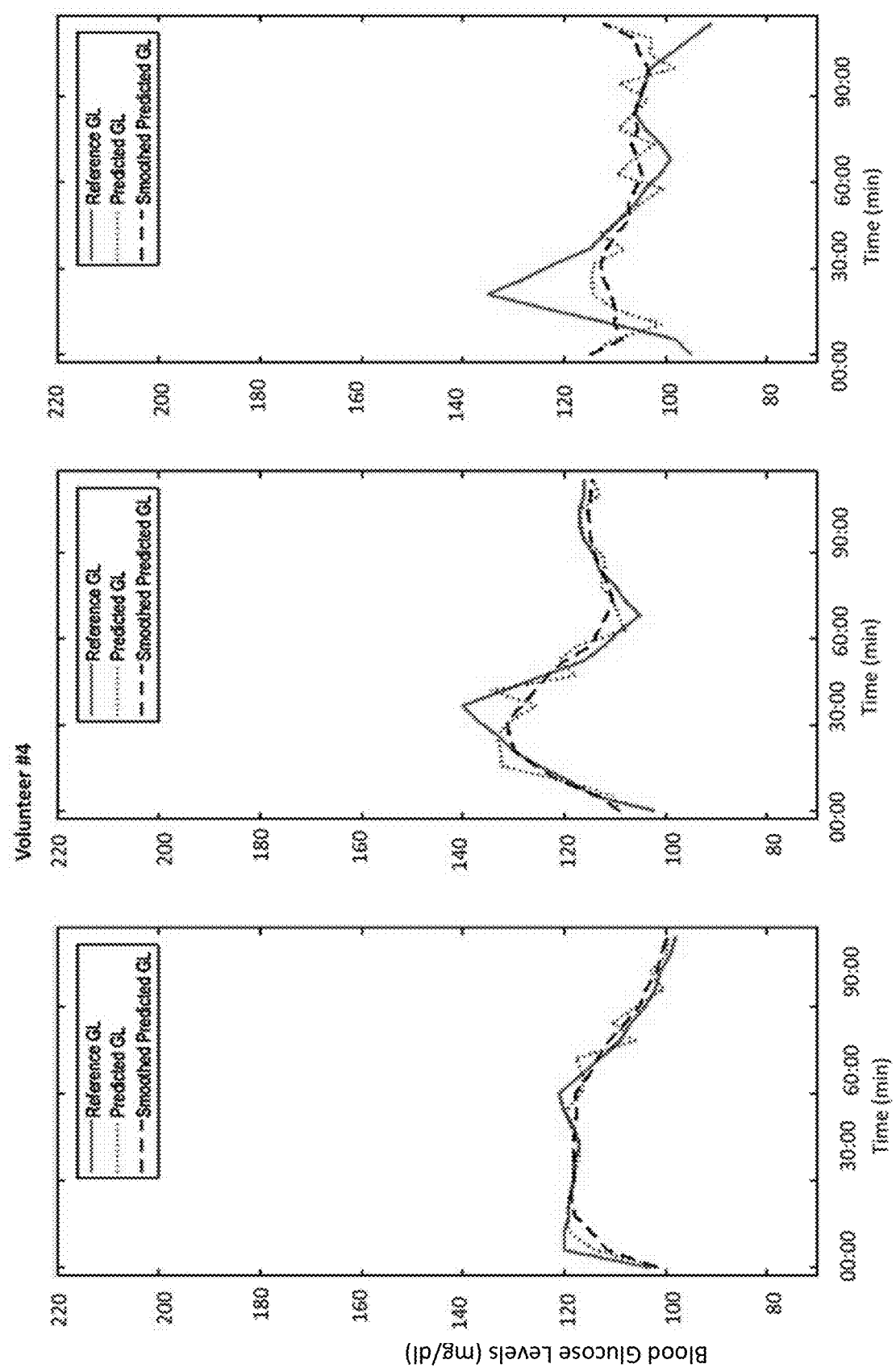
FIG. 39A is a graph showing the blood glucose levels for the Flexible Antenna: leave-one-out for Volunteer 4.

The individual results for Volunteer #4 for the Flexible Antenna: leave-one-out is shown in FIG. 39A. FIG. 39B shows the percentage error for the blood glucose levels taken compared to the reference glucose levels.

Figure 40A:
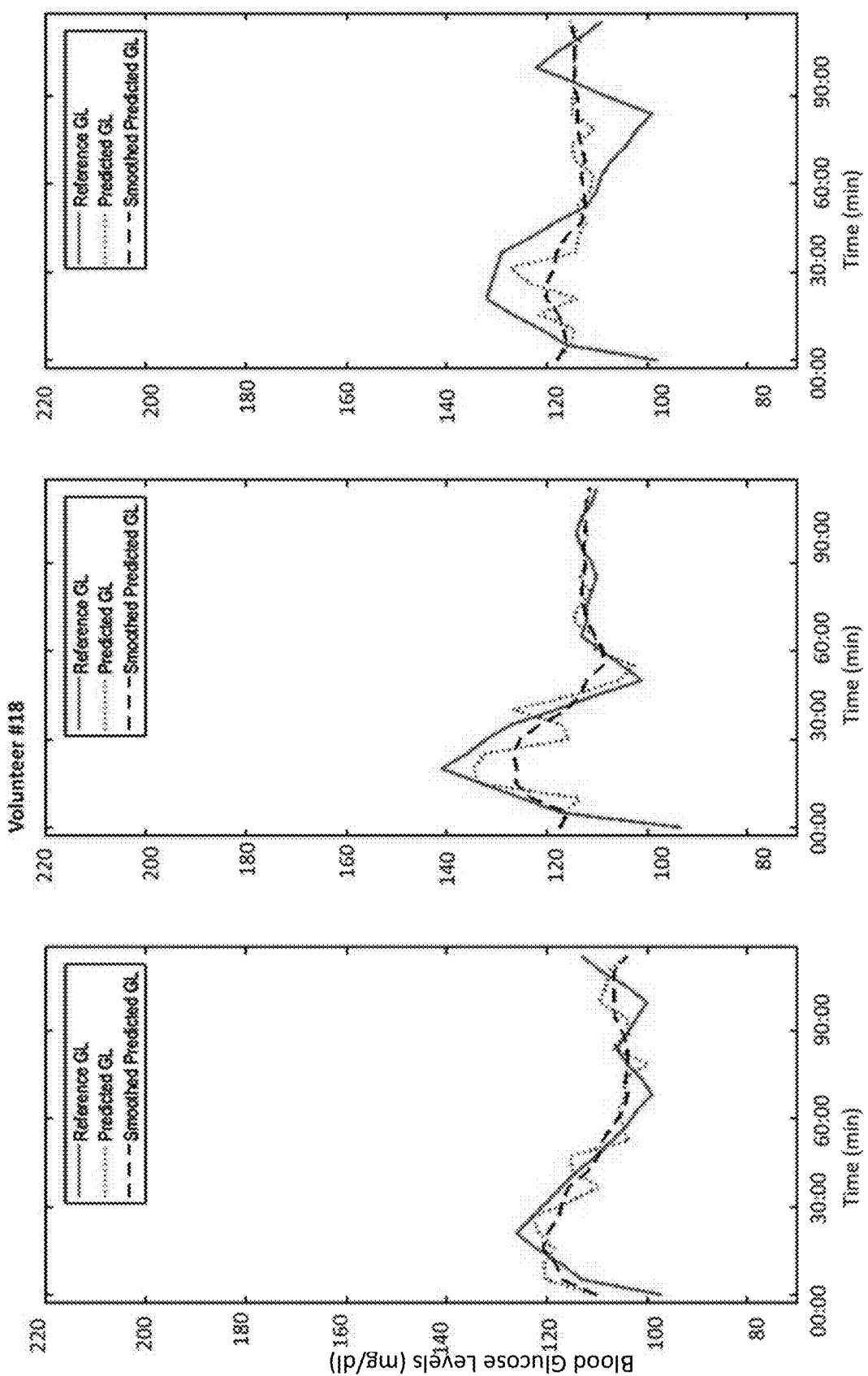
FIG. 40A is a graph showing the blood glucose levels for the Flexible Antenna: leave-one-out for Volunteer 18.

The individual results for Volunteer #18 for the Flexible Antenna: leave-one-out is shown in FIG. 40A. FIG. 40B shows the percentage error for the blood glucose levels taken compared to the reference glucose levels.

Figure 41:
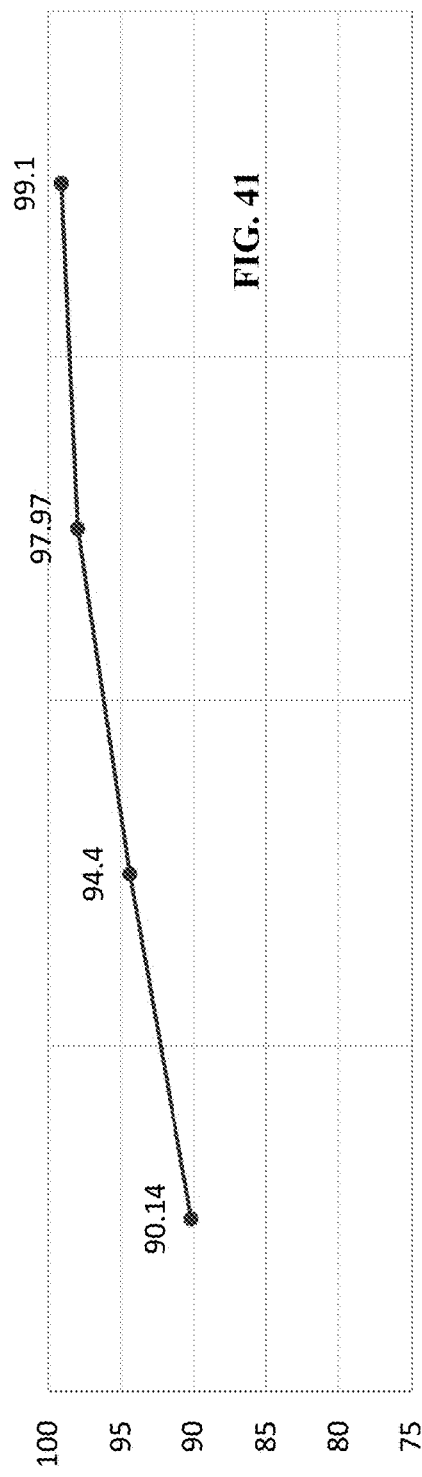
FIG. 41 is a graph showing the in vivo experimental results and prediction error range.

The in vivo experimental results for the flexible antenna and prediction error range are shown in FIG. 41 and Table 5 shows the prediction error range for the flexible and rigid antenna below.

TABLE 5

|  | Number of points | Within 15% | Within 20% | Within 30% | Within 40% | Outside 40% |
|---|---|---|---|---|---|---|
| Flexible | 1430 | 90.14 | 94.4 | 97.97 | 99.1 | 0.91 |
| Rigid | 1461 | 89.87 | 94.59 | 97.67 | 98.84 | 1.16 |

Figure 42A:
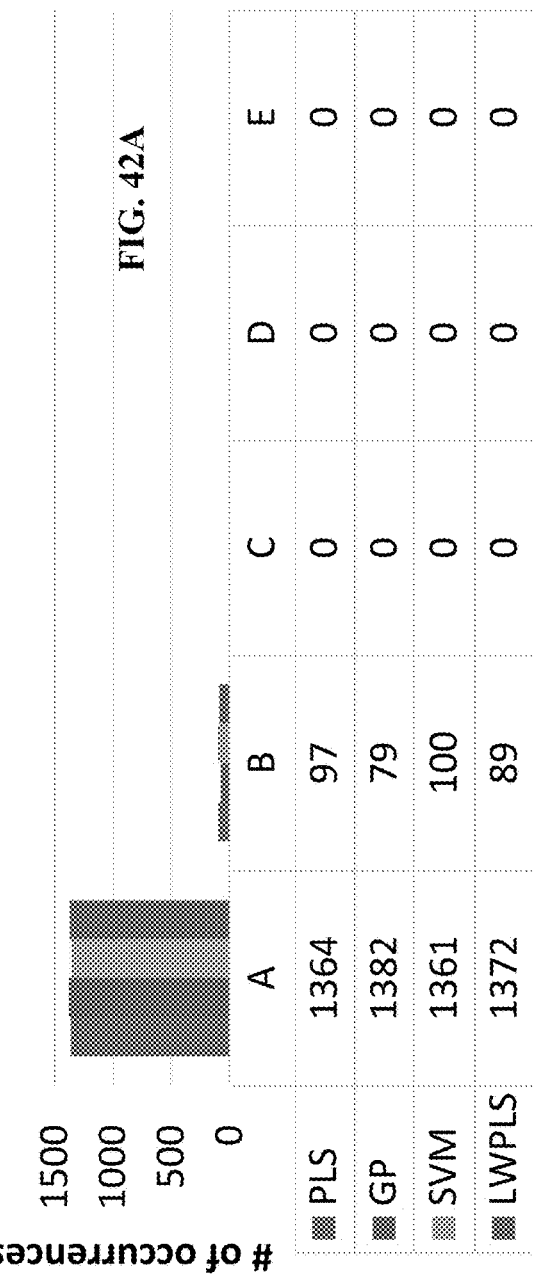
FIG. 42A is a graph showing the Clarke Error Grid Statistics for the in vivo results with Rigid Antenna: leave-one-out.
Figure 42B:
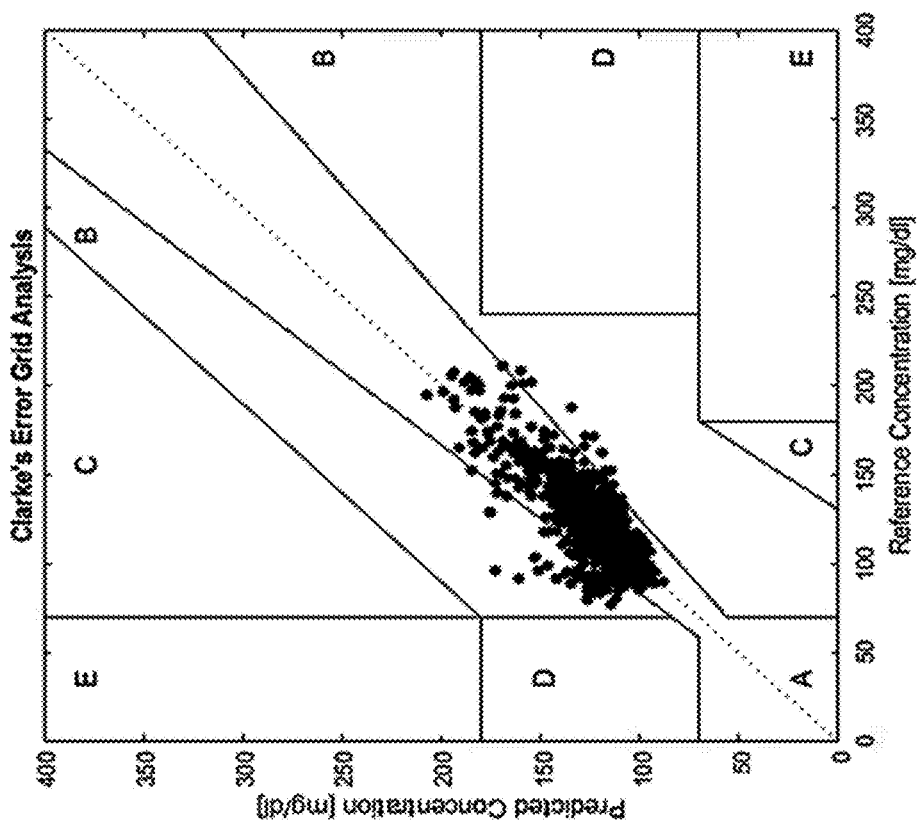
FIG. 42B is a graph showing the Clarke's Error Grid Analysis for the in vivo results with Rigid Antenna: leave one out.
Figure 42C:
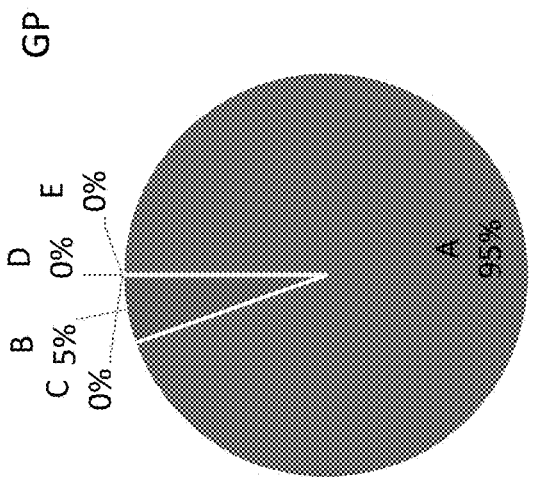
FIG. 42C is a pie graph showing all results are in Zones A and B which are considered clinically acceptable.

In vivo results with the Rigid Antenna: leave-one-out and the Clark Error Grid statistics is shown in FIG. 42A. FIG. 42B is the Clarke's Error Grid Analysis and FIG. 42C is the pie graph showing all results are in Zones A and B which are considered clinically acceptable.

Figure 43C:
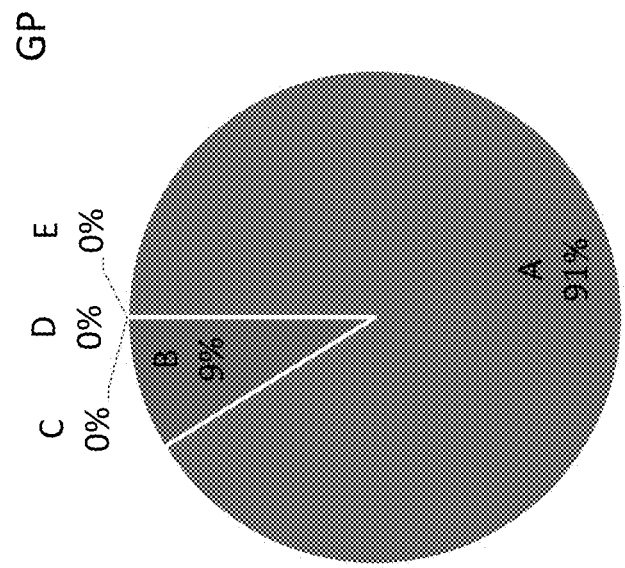
FIG. 43C is a pie graph showing all results are in Zones A and B which are considered clinically acceptable.
Figure 43B:
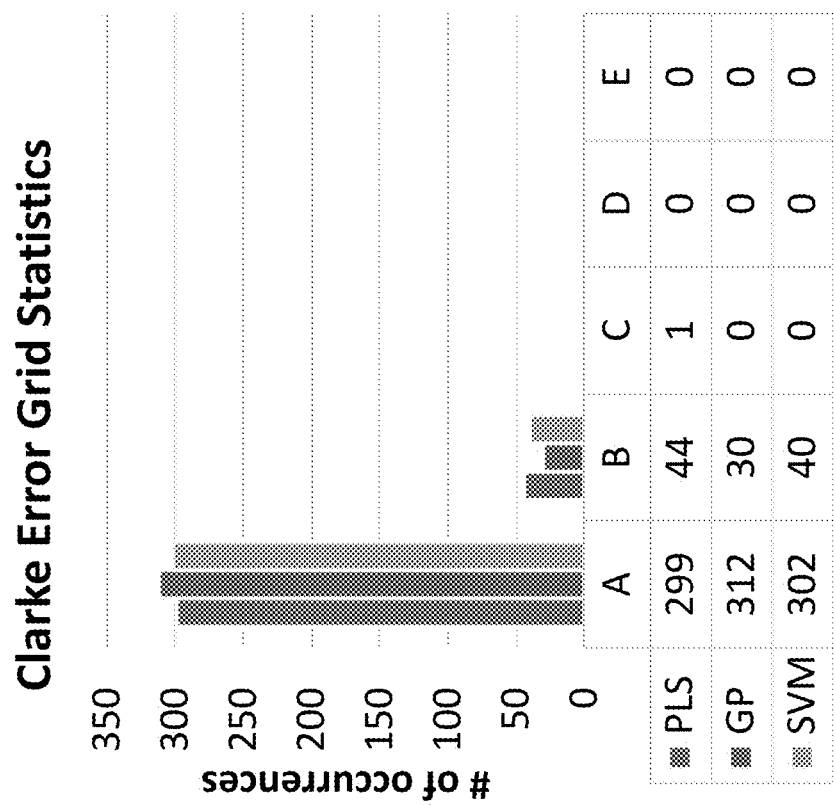
FIG. 43B is a graph showing the Clarke's Error Grid Analysis for the Flexible Antenna (training ⅔, Testing ⅓)
Figure 44A:
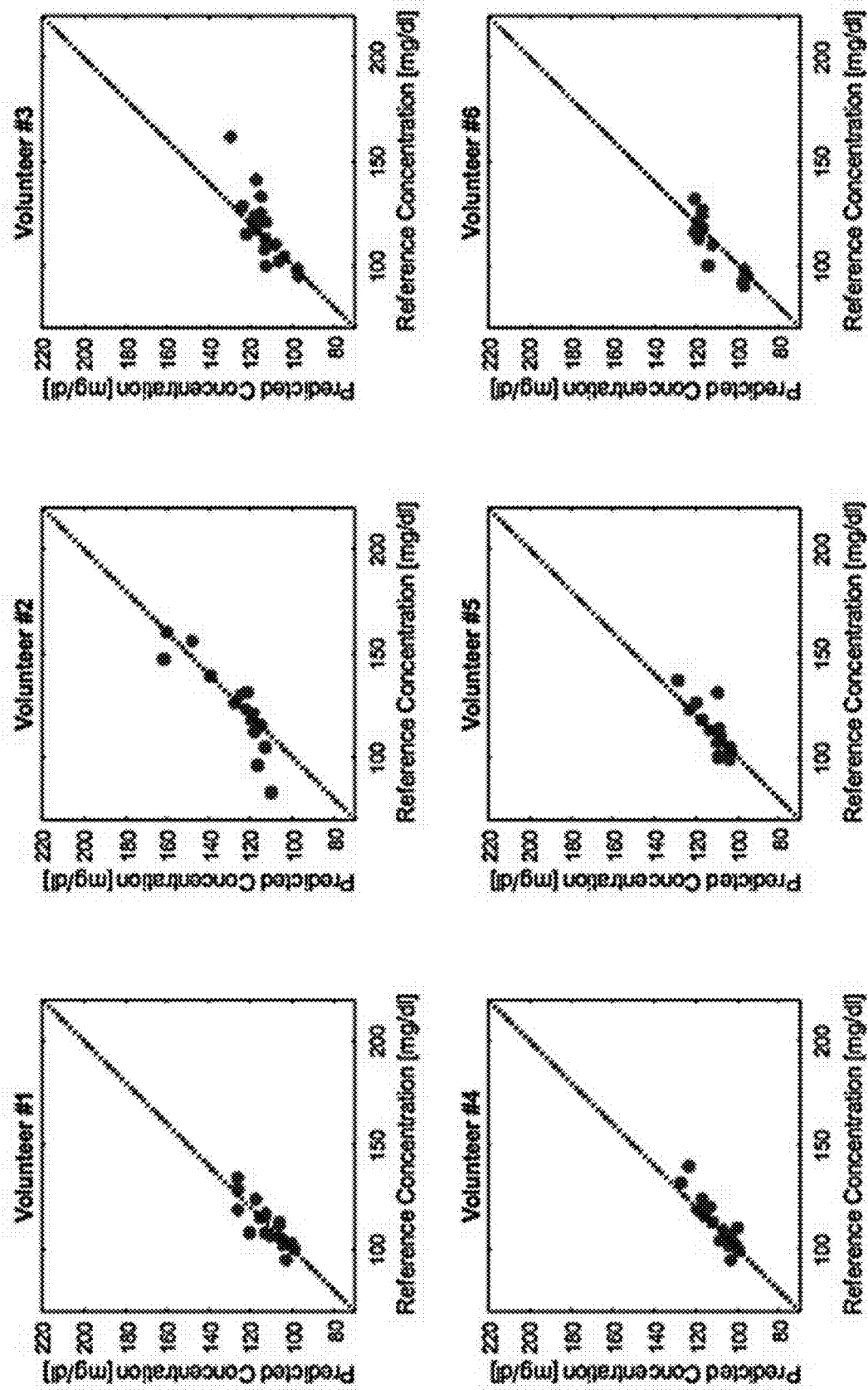
Figure 44B:
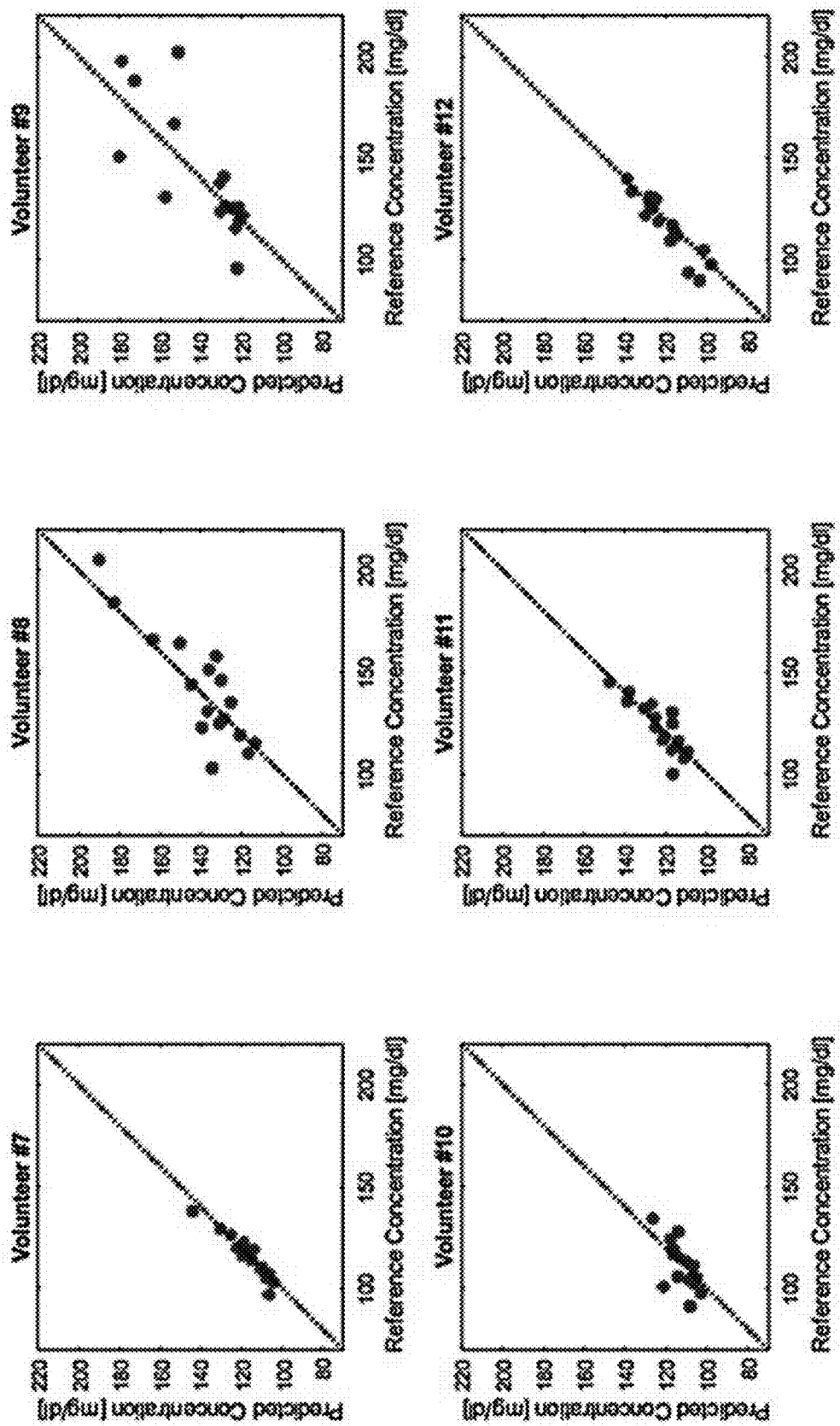
Figure 44C:
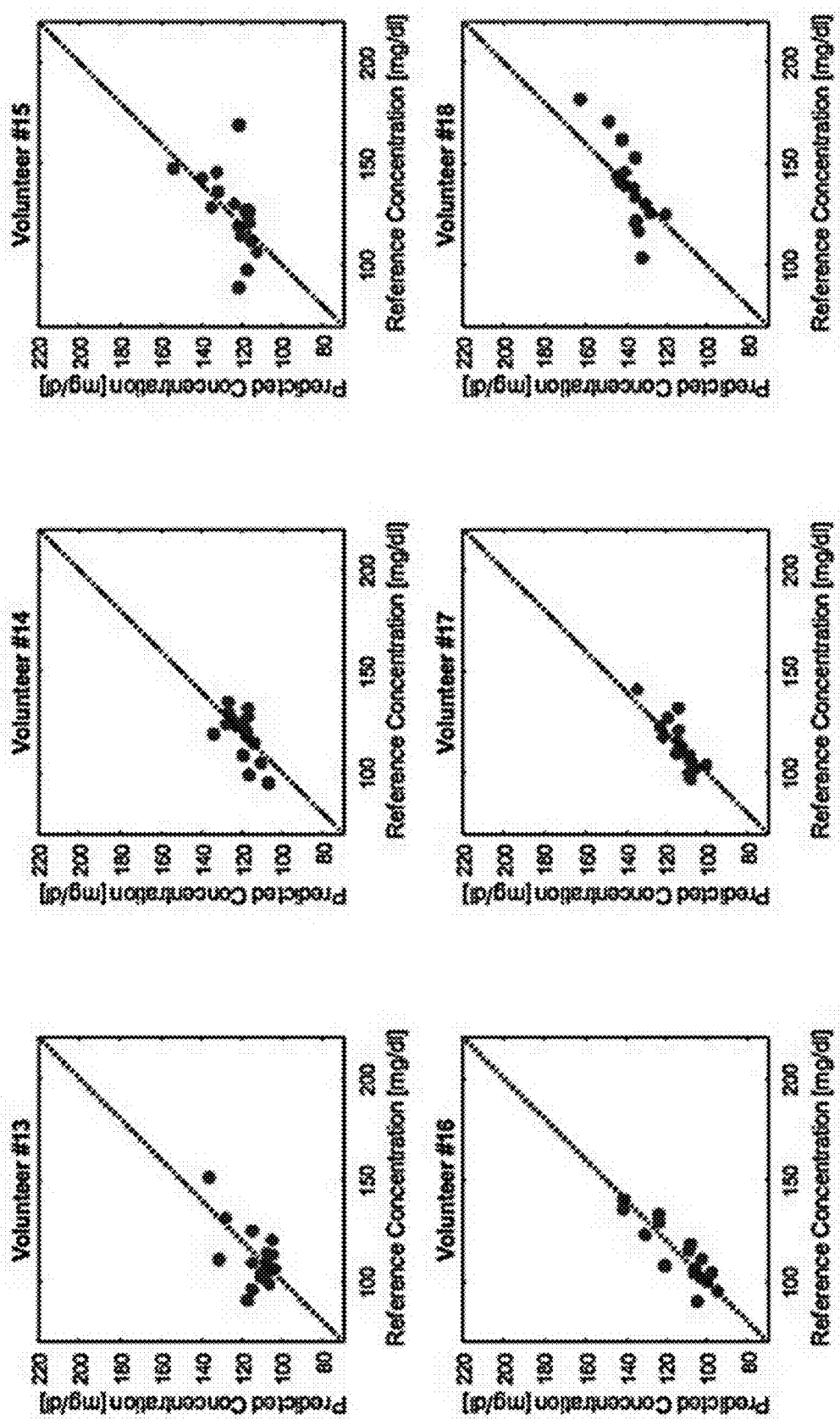

In vivo results with the Flexible Antenna (training ⅔, Testing ⅓) and the Clark Error Grid statistics is shown in FIG. 43A. FIG. 43B is the Clarke's Error Grid Analysis and FIG. 43C is the pie graph showing all results are in Zones A and B which are considered clinically acceptable.

Flexible Antenna (training ⅔, Testing ⅓) for Volunteers 1-20 are shown in FIGS. 44A-44E, showing the prediction concentration vs. the reference concentration.

Figure 45B:
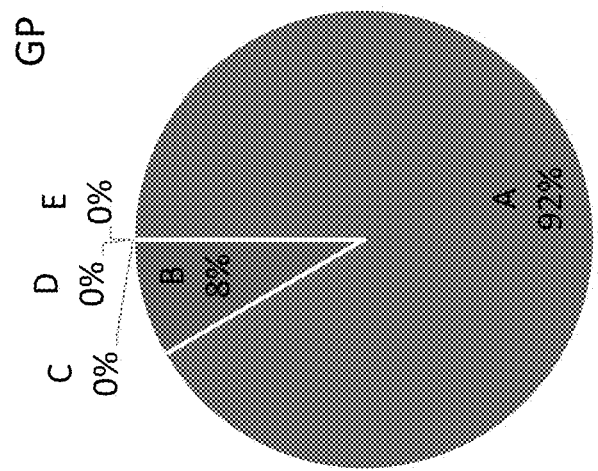
FIG. 45B is a graph showing the Clarke's Error Grid Analysis for the Rigid Antenna (training ⅔, Testing ⅓)
Figure 45A:
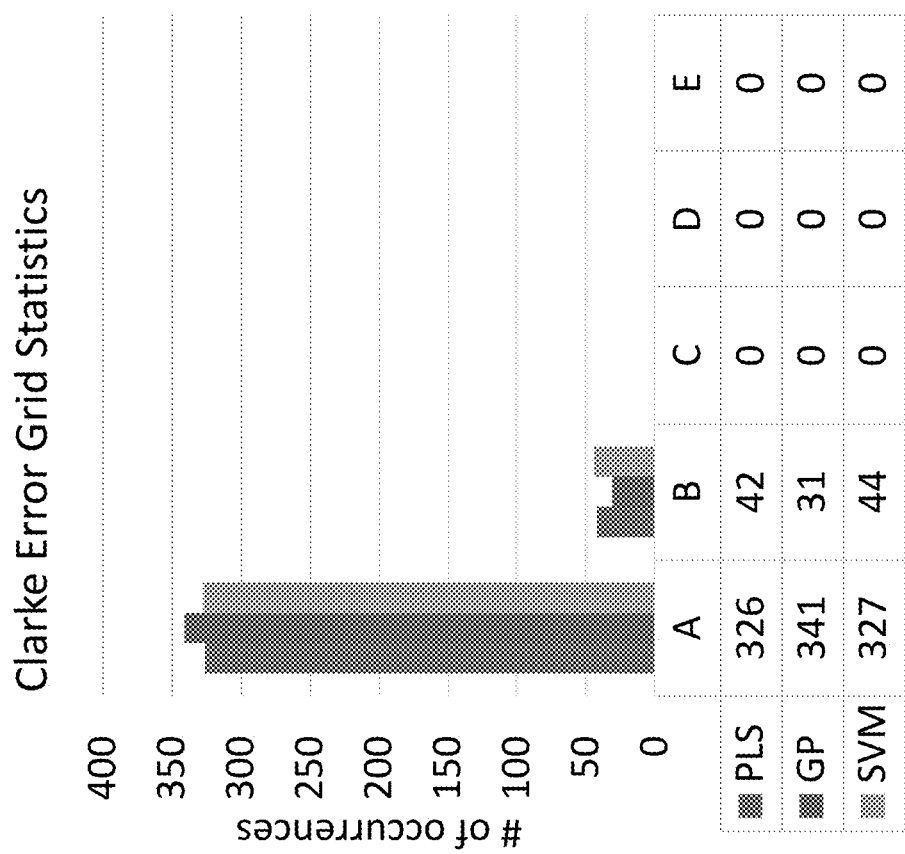
FIG. 45A is a graph showing the Clarke Error Grid Statistics for the in vivo results with Rigid Antenna (training ⅔, Testing ⅓)
Figure 45C:
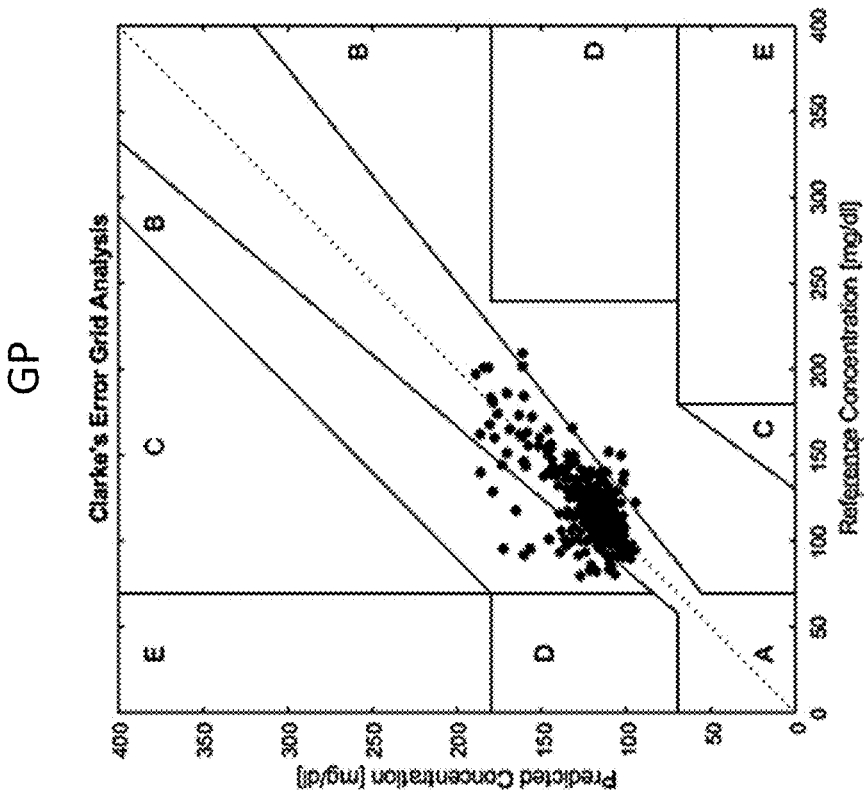
FIG. 45C is a pie graph showing all results are in Zones A and B which are considered clinically acceptable.

In vivo results for the Rigid Antenna (training ⅔, Testing ⅓) and the Clark Error Grid Statistics is shown in FIG. 45A FIG. 45B is a pie graph and FIG. 45C is the Clarke's Error Grid Analysis showing the all results are in Zones A and B are considered clinically acceptable.

Example 4: In Vivo Experiment on Human Subjects

Figure 46A:
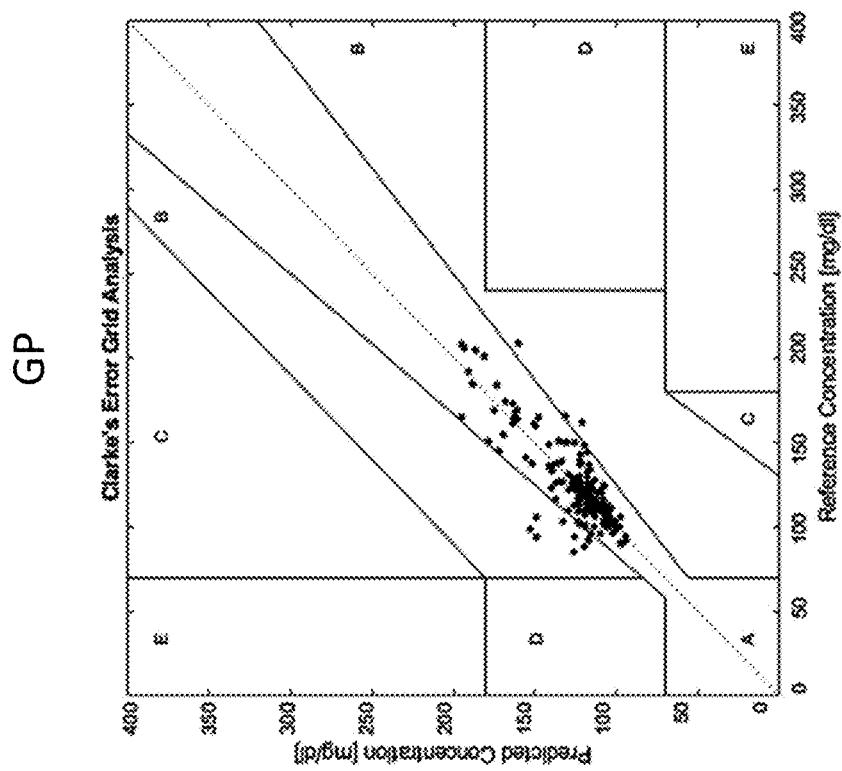
FIGS. 46A-46C are graphs showing the Clarke's Error Grid Analysis for Rigid Antenna in GP, PLS, and LW PLS models.
Figure 46C:
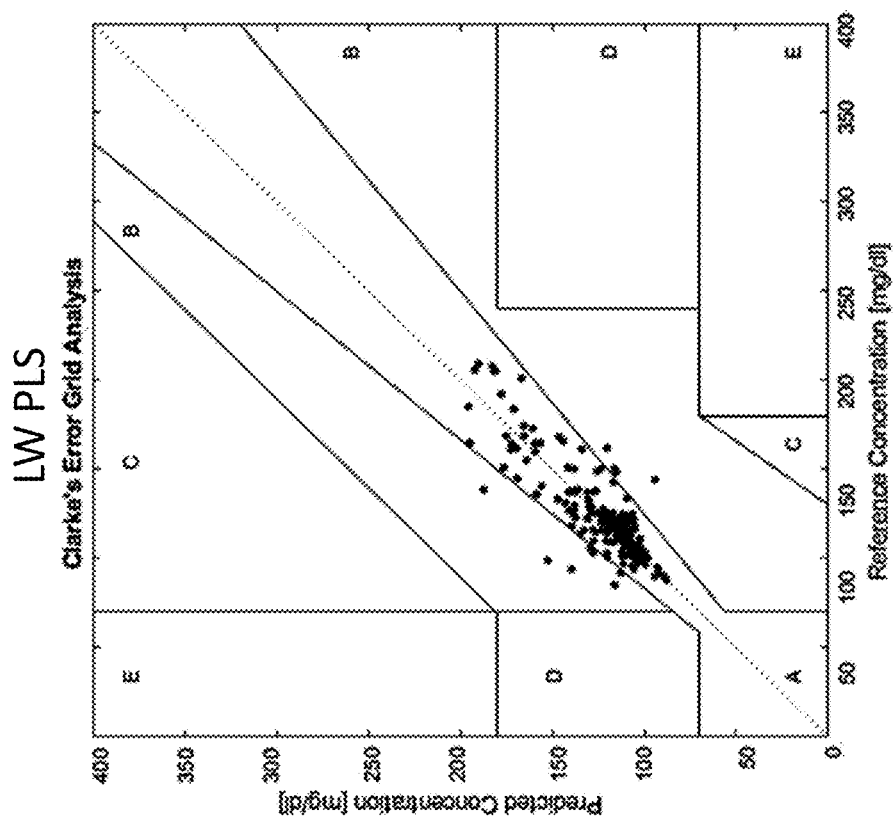
Figure 46B:
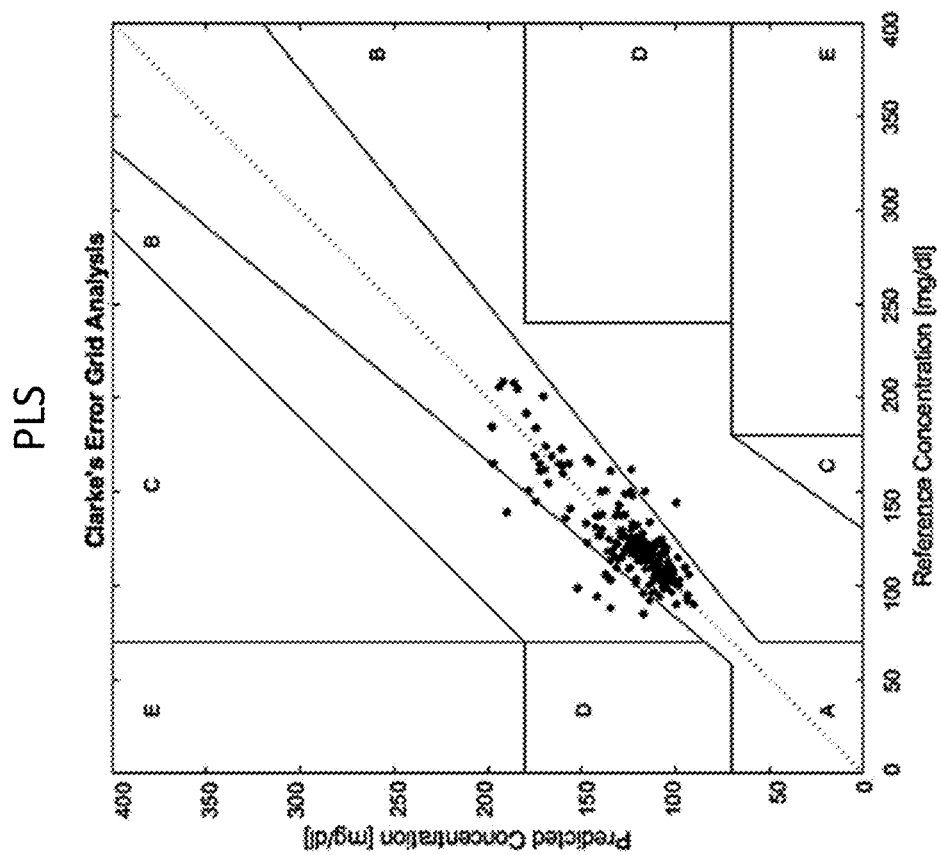

The Rigid Antenna—Clarke Grid Error Analysis for the GP, PLS, LW PLS models is shown in FIGS. 46A-46C. For each volunteer, a unique regression model was built. All the values are in Zone A and B are clinically acceptable zones.

TABLE 6

In Vivo Experiment on Human subjects Experimental Setup- Rigid Antenna-Clarke Grid Error for the LW PLS, PLS, GP, and RBF modeling techniques.

| | Rigid Antenna | | | | | |
|---|---|---|---|---|---|---|
|  | Zone A | Zone B | Zone C | Zone D | Zone E | TOTAL |
| LW PLS | 222 | 13 | 0 | 0 | 0 | 235 |
| PLS | 222 | 13 | 0 | 0 | 0 | 235 |
| GP | 222 | 13 | 0 | 0 | 0 | 235 |
| RBF | 215 | 19 | 1 | 0 | 0 | 235 |

All results except one are in Zones A and B which are considered clinically acceptable.

Mean % Error for the Rigid Antenna for each volunteer for the LW PLS, PLS, GP, and RBF modeling techniques is shown in FIG. 47. The GP modeling technique had the lowest mean percent error at 6.5.

In Vivo Experiment on Human subjects Experimental Setup—flexible antenna—Clarke

Figure 48B:
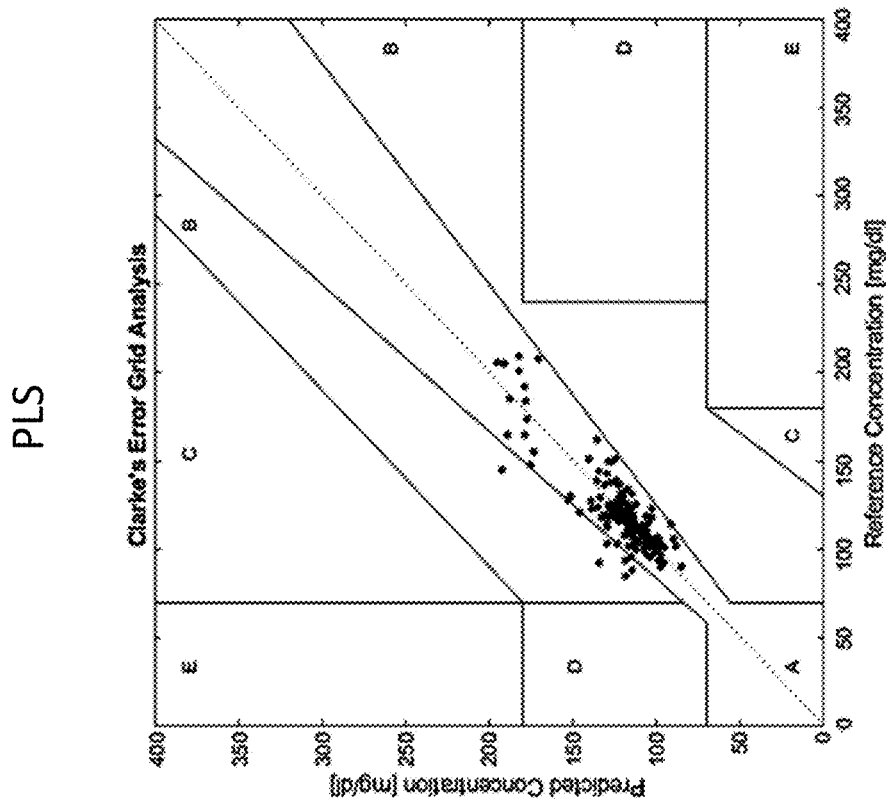
FIGS. 48A-48C are graphs showing the Vivo Experiment on Human subjects Experimental Setup—flexible antenna—Clarke Grid error for GP, PLS, and LW PLS, respectively.
Figure 48A:
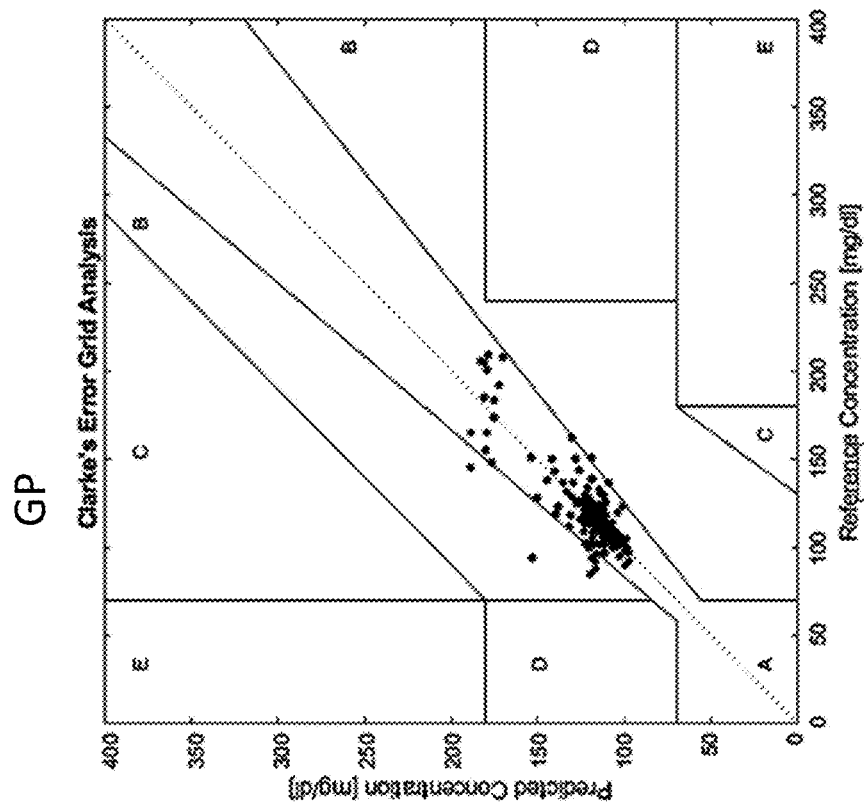
Figure 48C:
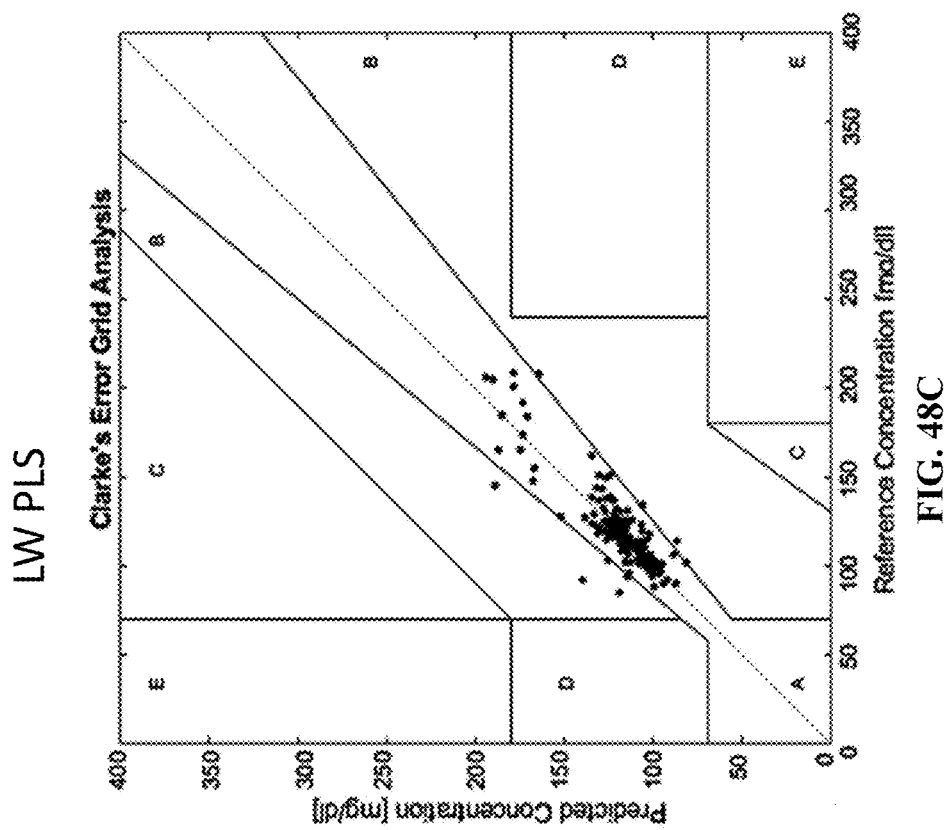

Grid error is shown in FIGS. 48A-48C for GP, PLS, and LW PLS. For each volunteer, a unique regression model for the Flexible Antennae was developed. All the values are in Zone A and B were clinically acceptable zones. The model is developed for a given individual.

TABLE 7

In Vivo Experiment on Human subjects
Experimental Setup- Flexible antenna

Flexible Antenna

|        | Zone A | Zone B | Zone C | Zone D | Zone E | TOTAL |
|--------|--------|--------|--------|--------|--------|-------|
| LW PLS | 205    | 7      | 0      | 0      | 0      | 212   |
| PLS    | 205    | 7      | 0      | 0      | 0      | 212   |
| GP     | 202    | 10     | 0      | 0      | 0      | 212   |
| RBF    | 186    | 26     | 0      | 0      | 0      | 212   |

All results are in Zones A and B are considered clinically acceptable

In Vivo Experiment on Human subjects for the flexible antennae and the Mean % Error for each volunteer for the LW PLS, PLS, GP, and RBF modeling techniques are shown in FIG. 49. The LW PLS modeling technique had the lowest mean percent error at 6.5.

Example 6: Clinical Trials Semi-Flexible Antenna

Figure 50A:
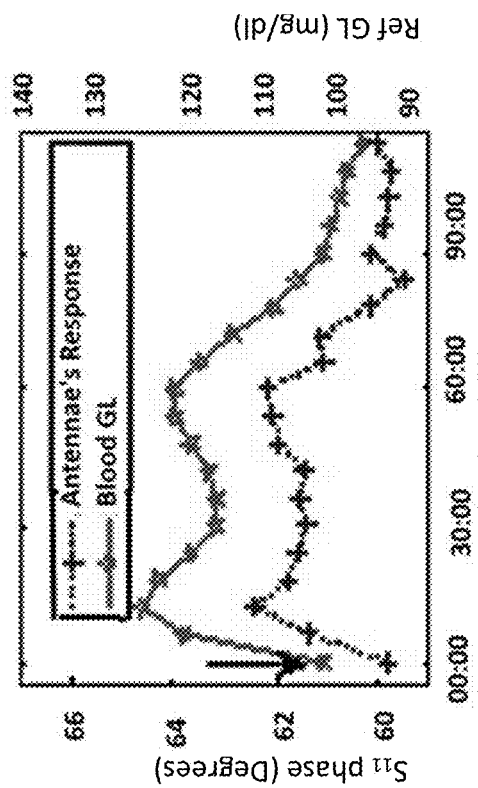
FIG. 50A is a graph showing the Antenna's response during one oral glucose tolerance test (OGTT), where the blue curve shows the $S_{11}$ phase response of the semi-flexible antenna collected at about 0.7995 GHz versus time during an OGTT. This curve follows well the blood glucose profile curve shown in red, achieving a high correlation of 0.944 between the two measurements. The arrow indicates the onset of the glucose intake.
Figure 50B:
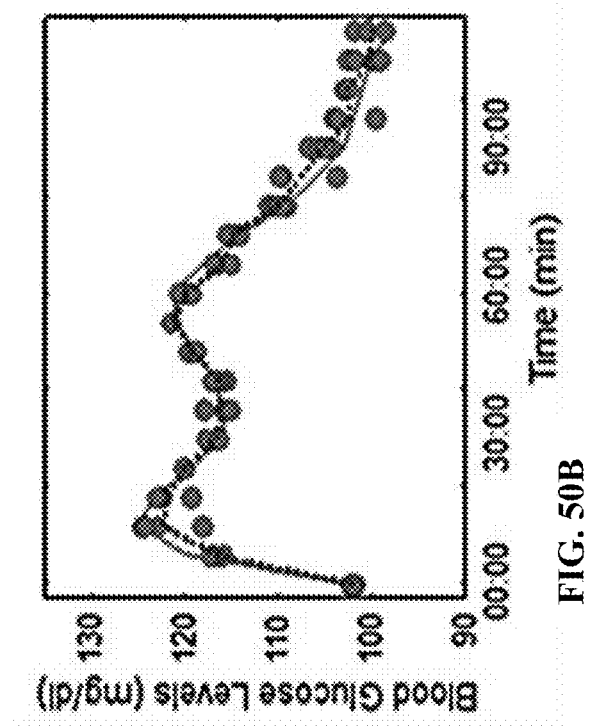
FIG. 50B is a graph showing the Blood Glucose estimation using the Gaussian Process model. Actual glucose levels (red) compared with the estimated glucose levels over time (green dots show the estimations resulting from the 10 random repetitions in most cases closely overlapping and the blue curve shows the mean estimation). Results presented here are obtained by the flexible antenna on volunteer #4.
Figures 50C, 50D:
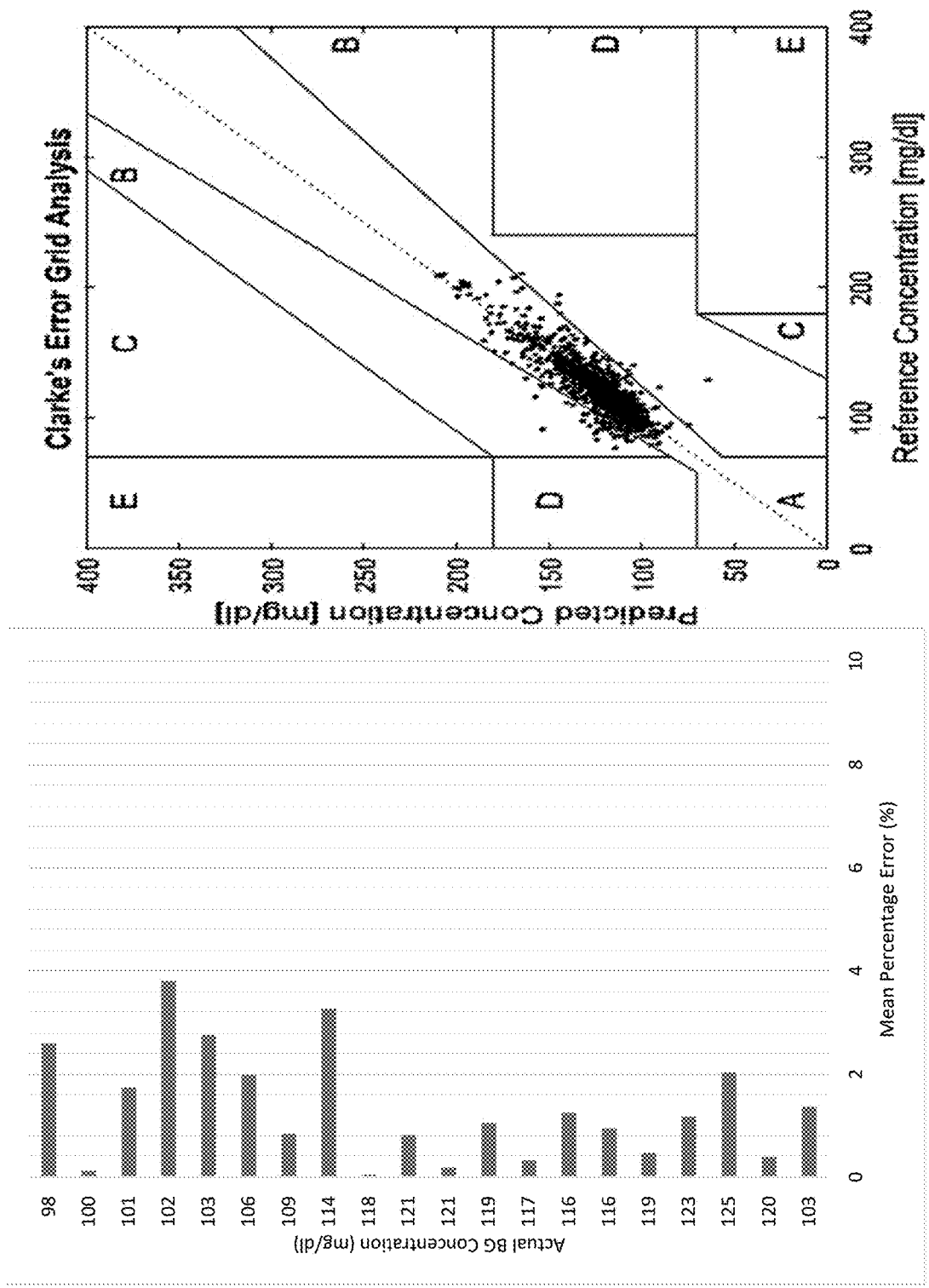
FIG. 50C is a graph showing the mean percentage error calculated between the actual glucose levels and mean estimated values showing; all the estimations having a mean error lower than 5% and great estimations of glucose concentration with a MARD of 1.36%.
FIG. 50D is a Clarke Error Grid for the 21 volunteers for the semi-flexible antenna.

FIGS. 50A-50D show the Human trials on healthy volunteers using the semi-flexible antenna. Real-time, continuous glucose monitoring on healthy volunteers. FIG. 50A shows the Antenna's response during one OGTT. Left: the blue curve shows the S11 phase response of the semi-flexible antenna collected at 0.7995 GHz versus time during an OGTT. This curve follows well the blood glucose profile curve shown in red, achieving a high correlation of 0.944 between the two measurements. The arrow indicates the onset of the glucose intake. FIG. 50B shows Blood Glucose estimation using the Gaussian Process model. Actual glucose levels (red) compared with the estimated glucose levels over time (green dots shows the estimations resulting from the 10 random repetitions in most cases closely overlapping and the blue curve shows the mean estimation). Results presented here are obtained by the flexible antenna on volunteer #4. FIG. 50C shows the mean percentage error calculated between the actual glucose levels and mean estimated values showing; all the estimations having a mean error lower than 5%. Great estimations of glucose concentration with a MARD of 1.36% were achieved. FIG. 50D shows the Clarke Error Grid for the 21 volunteers for the semi-flexible antenna. This plot compares the predicted glucose levels by the proposed system and the reference glucose levels obtained by finger-pricks measurements. A mean percentage error of 6.08% is obtained using the Gaussian process regression model (individual models are created for each volunteer). All the predicted values are in the acceptable zones A and B with the majority in zone A (96.04%). The 91.59% of predicted values are within the 15% error 96.04% are within 20% error, 99.16% are within 30% and 99.72% are within 40% error.

Figure 51:
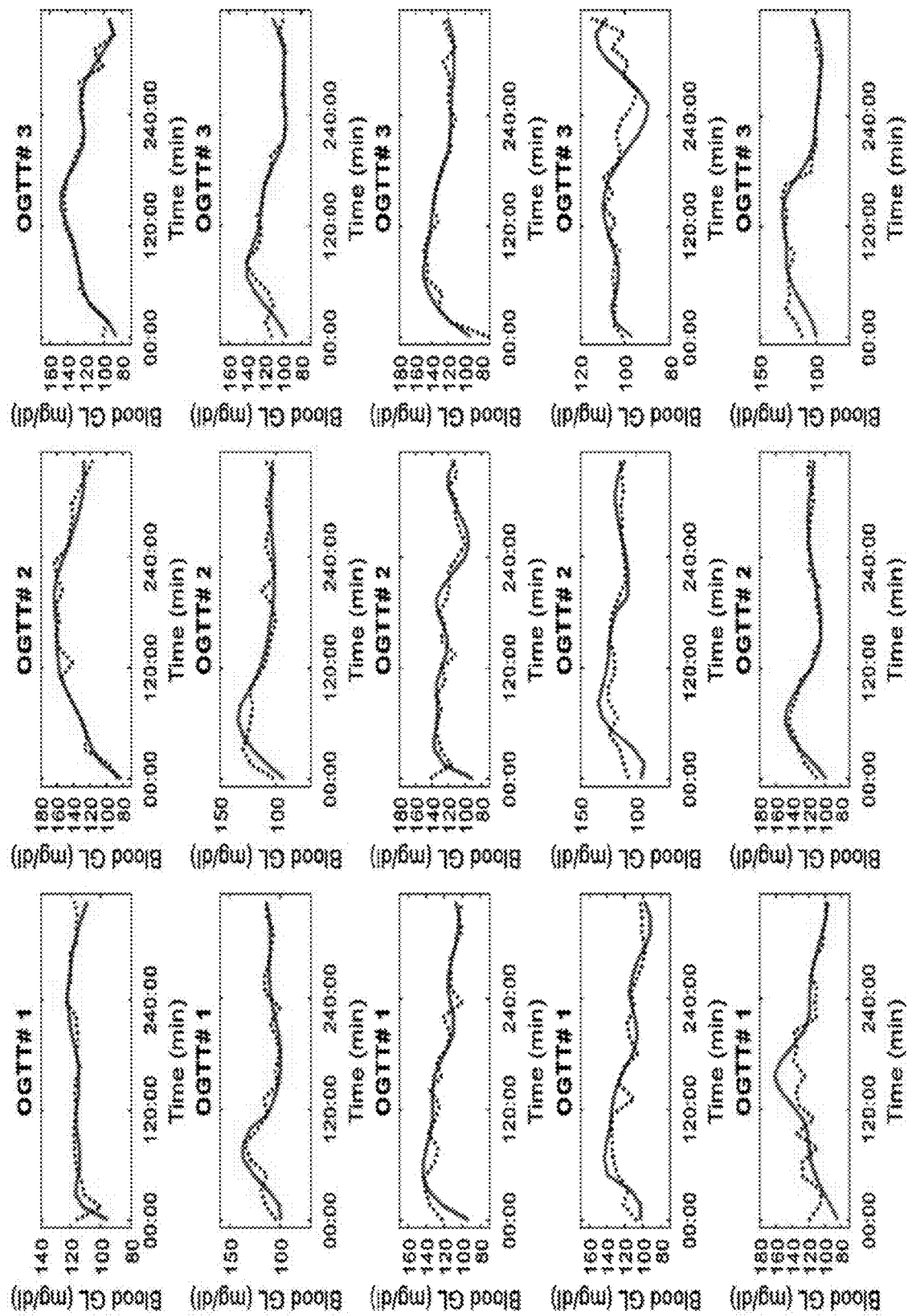
FIG. 51 are graphs of the in-vivo experiments on 10 volunteers using the semi-flexible antenna. Example of reference glucose levels (in red curve) vs predicted glucose levels using the individual models (in dotted blue curve) for 10 different volunteers corresponding to 30 OGTTs. The plots shows good agreement between the reference and the predicted values

FIG. 51: in-vivo experiments on 10 volunteers using the semi-flexible antenna. Example of reference glucose levels (in red curve) vs predicted glucose levels using the individual models (in dotted blue curve) for 10 different volunteers corresponding to 30 OGTTs. The plots shows good agreement between the reference and the predicted values.

Figure 52B:
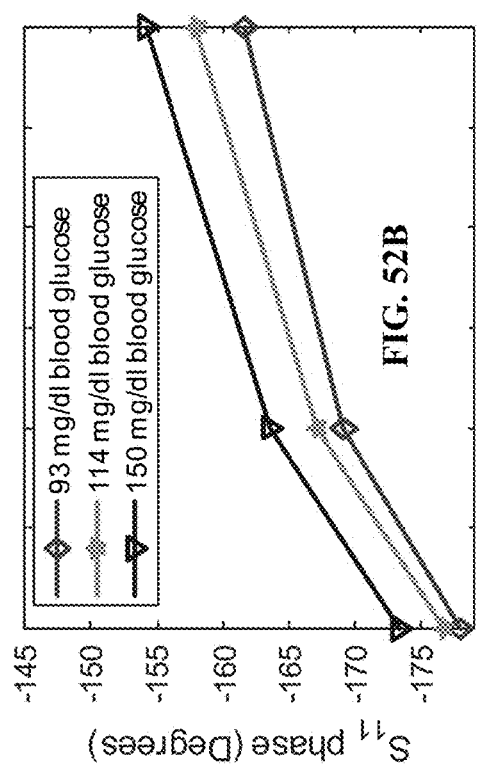
FIG. 52B is a graph showing the antenna's S11 phase response around 1.36 GHz, corresponding to three different blood glucose concentrations. This plot illustrates good tracking of the glucose profile.
Figure 52D:
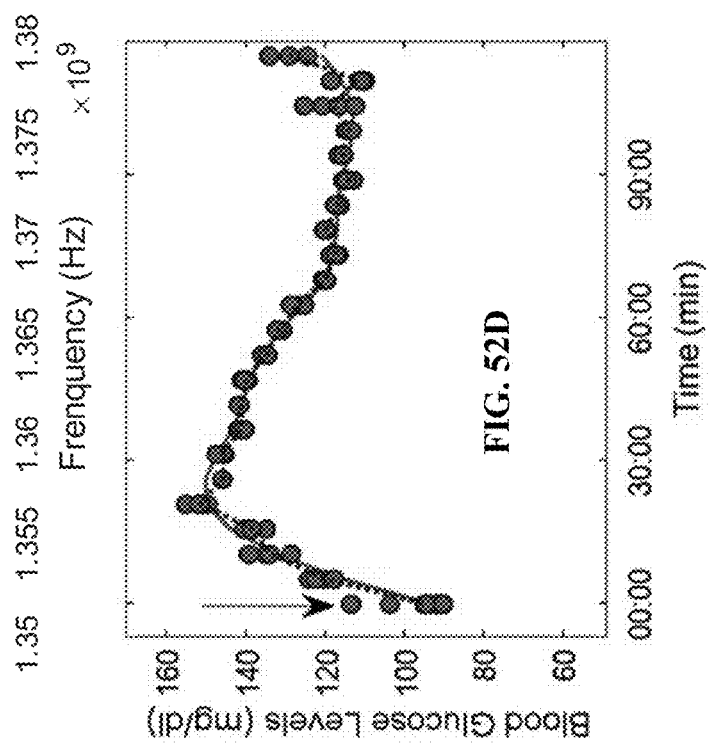
FIG. 52D is a graph showing the actual glucose levels (red) compared with the estimated glucose levels over time (green dots shows the estimations resulting from the 10 random repetitions in most cases closely overlapping and the blue curve shows the mean estimation).
Figure 52A:
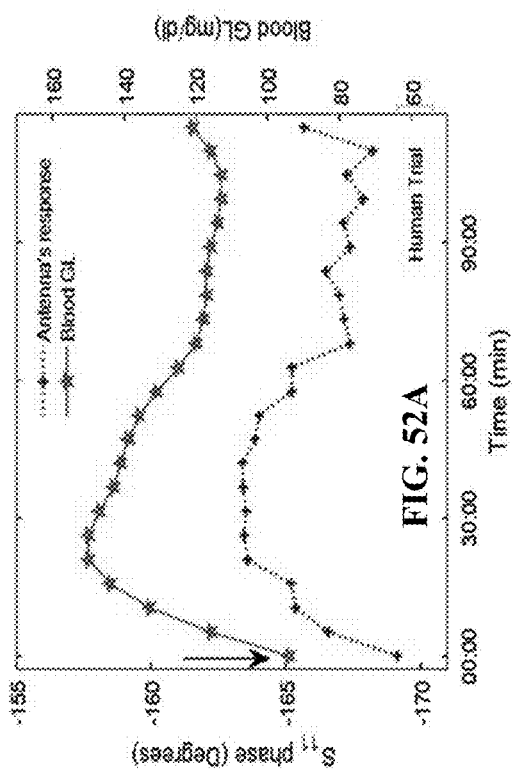
FIG. 52A is a graph showing the blue curve shows the S11 phase response of the flexible antenna collected at 1.36 GHz versus time during an OGTT. This curve follows well the blood glucose profile curve shown in red, achieving a high correlation of −0.94 between the two measurements. The arrow indicates the onset of the glucose intake.
Figure 52C:
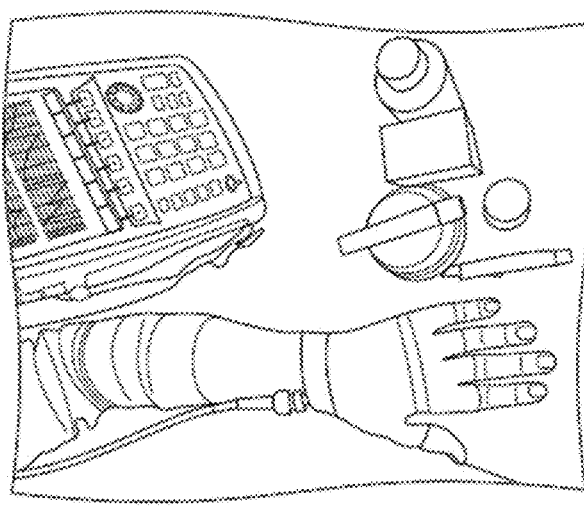
FIG. 52C is a photo showing the experimental setup: the two antenna prototypes are placed on the volunteer's hands and readings are taken simultaneously from both antennas.
Figures 52E, 52F:
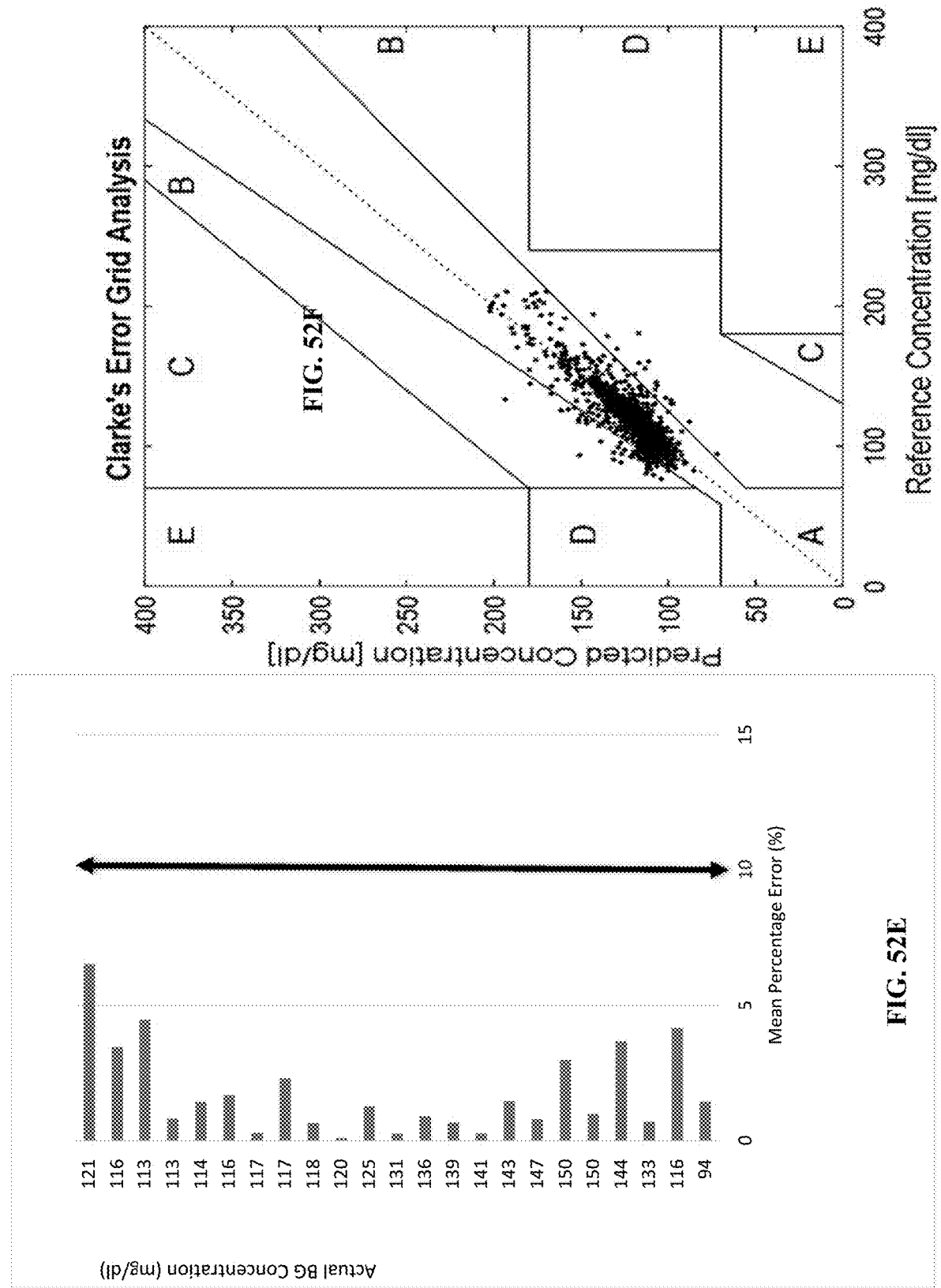
FIG. 52E is a graph showing the mean percentage error calculated between the actual glucose levels and mean estimated values showing; all the estimations having a mean error lower than 10%. Great estimations of glucose concentration with a MARD of 1.78%.
FIG. 52F is the Clarke Error Grid for all the OGTT conducted by the 21 volunteers using the flexible antenna.

FIG. 52A-52F Human trials on healthy volunteers using the flexible antenna. Real-time, continuous glucose monitoring on healthy volunteers. FIG. 52A-52B shows the Antenna's response during one OGTT. FIG. 52A shows the blue curve shows the S11 phase response of the flexible antenna collected at 1.36 GHz versus time during an OGTT. This curve follows well the blood glucose profile curve shown in red, achieving a high correlation of −0.94 between the two measurements. The arrow indicates the onset of the glucose intake. FIG. 52B shows the antenna's S11 phase response around 1.36 GHz, corresponding to three different blood glucose concentrations. This plot illustrates good tracking of the glucose profile. FIG. 52C shows the experimental setup: the two antenna prototypes are placed on the volunteer's hands and readings are taken simultaneously from both antennas. FIG. 52D-52F shows the Blood Glucose estimation using the Gaussian Process model. FIG. 52D shows the actual glucose levels (red) compared with the estimated glucose levels over time (green dots shows the estimations resulting from the 10 random repetitions in most cases closely overlapping and the blue curve shows the mean estimation). Results presented here are obtained by the flexible antenna on volunteer #12. FIG. 52E shows the mean percentage error calculated between the actual glucose levels and mean estimated values showing; all the estimations having a mean error lower than 10%. Great estimations of glucose concentration with a MARD of 1.78% were achieved. FIG. 52F is the Clarke Error Grid for all the OGTT conducted by the 21 volunteers using the flexible antenna. This plot compares the mean estimated glucose levels by the proposed system and the reference glucose levels obtained by finger-pricks measurements. A MARD of 6.18% is obtained using the developed Gaussian process regression models (individual models are developed for each volunteer as explained in the supplementary note 12). All the estimated values are in the acceptable zones A and B with the majority in zone A (94.96%). 89.78% of estimated values are within the 15% error 94.96% are within 20% error, 98.86% are within 30% and 99.71% are within 40% error.

Figure 53A:
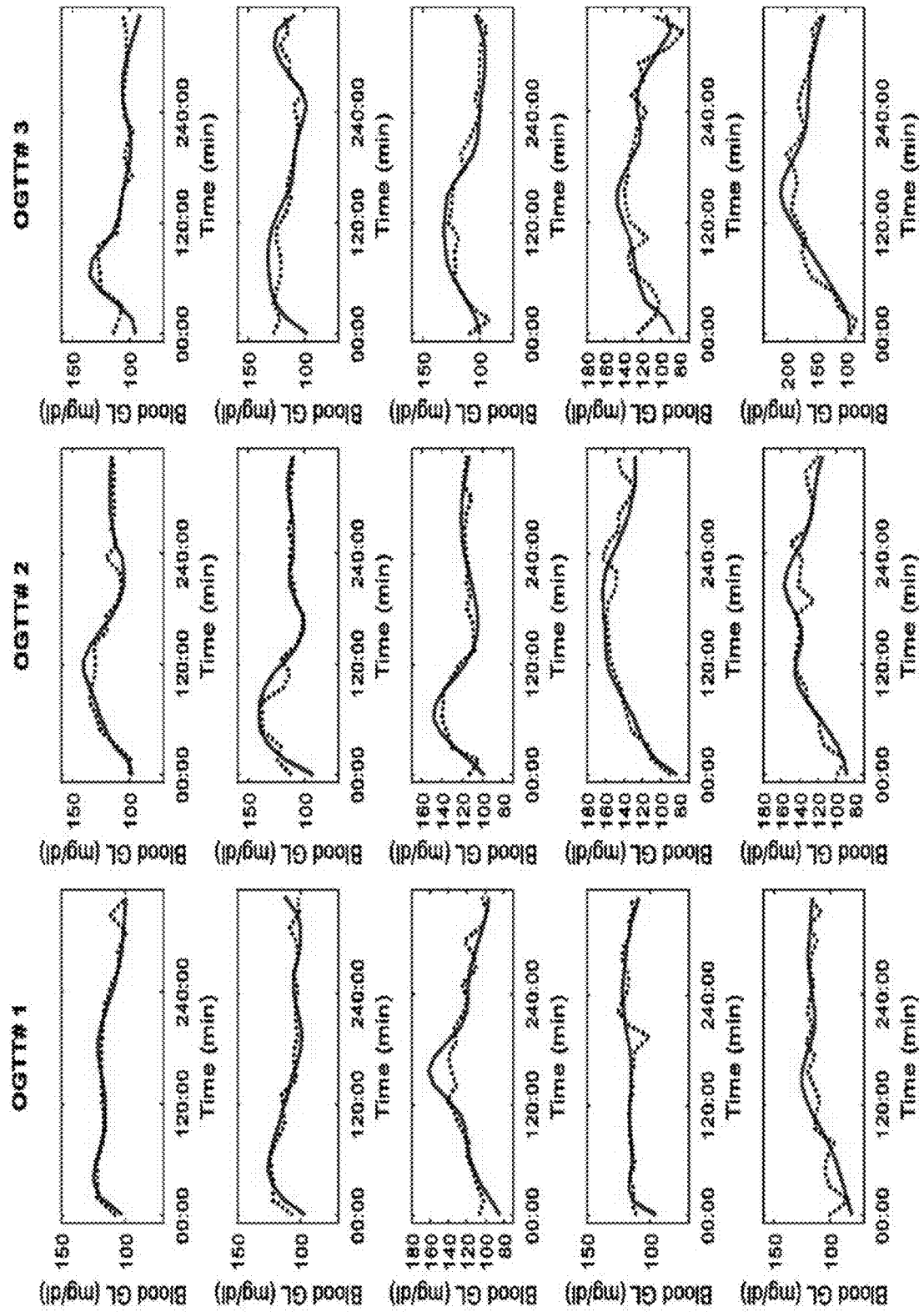
FIGS. 53A-53B are graphs showing the in-vivo experiments on 10 volunteers using the flexible antenna. Example of reference glucose levels (in red curve) Vs predicted glucose levels using the individual models (in dotted blue curve) for 10 different volunteers corresponding to 30 OGTTs.
Figure 53B:
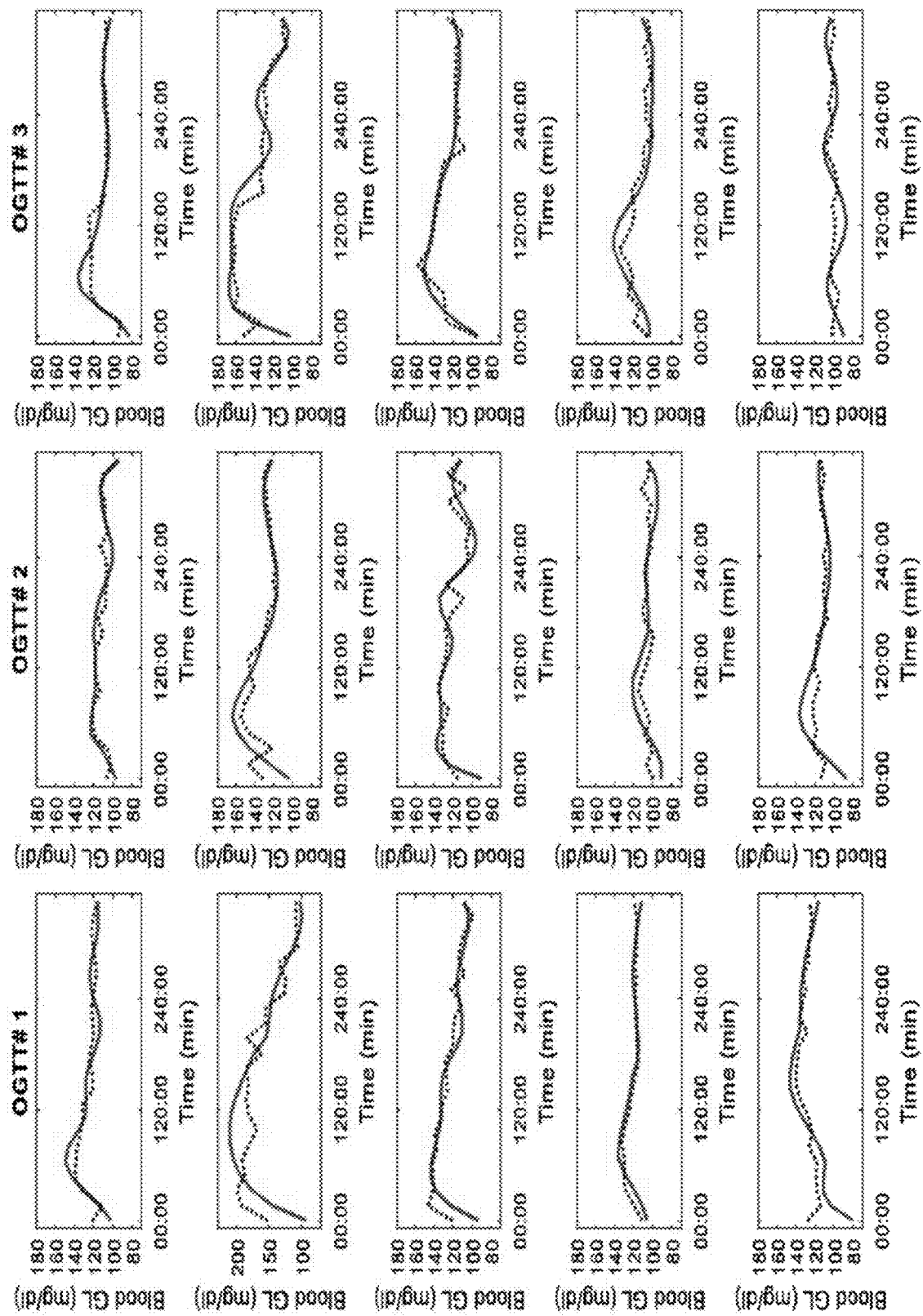

FIGS. 53A-53B show the in-vivo experiments on 10 volunteers using the flexible antenna. Example of reference glucose levels (in red curve) Vs predicted glucose levels using the individual models (in dotted blue curve) for 10 different volunteers corresponding to 30 OGTTs. The plots shows good agreement between the reference and the predicted values.

Example: Detection of Different Glucose Levels

The embodiment shown in FIG. 5 is used in this example. The free space multi-band characteristic, as illustrated in FIG. 54A, enables the analysis of the antenna's response at different frequencies thereby allowing for a more holistic contactless characterization of blood constituents with improved sensitivity. A foam container filled with FBS glucose solution is placed above the sensing layer of the slot antenna. The antenna is connected to a vector network analyzer (VNA) to measure its S11 coefficient over the 0.5-1.5 GHz frequency span. The antenna is fixed during the whole experiment, and the glucose concentration of the FBS solution is varied with a step of 50 mg/dl to cover a wide range of concentrations representing a glycemic range that varies from 28 to 471 mg/dl. The actual glucose levels are measured using an invasive-glucometer (Accu-Chek from ROCHER). When the antenna is loaded with the FBS solution, a clear shift in its S11 magnitude is noticed. This shift in magnitude is further manifested with glucose level variations as illustrated in FIG. 54A. To further elaborate on this shift and interpret its significance, the magnitude and phase of the antenna's reflection coefficient are shown in FIG. 54B-54C as a function of the corresponding reference glucose levels at different frequencies of operation. For glucose level variation over the 28-471 mg/dl range (a total change of 443 mg/dl equivalent to 24.5 mmol/l), the corresponding S11 magnitude variation, measured at 0.9875 GHz, is found to be 0.678 dB. At 1.1125 GHz, a total variation of 2.64 dB and a correlation r=0.987 between the S11 magnitude and the reference glucose level was recorded. The highly achieved correlation is also reflected in the almost linear variation of the S11 magnitude in regards to variations in the glucose level as illustrated for the specific feature frequency as shown in FIG. 54B. At 1.0625, the S11 phase demonstrates a total change of 9 degrees while at 1.05 GHz, a total change of 10 degrees with a correlation r=0.897 was achieved. One notices that the S11 phase variation manifests high sensitivity towards the glucose variations. Hence, sensitivities of 0.006 dB/mg·dl$^{-1}$ and 0.023 degrees/mg·dl$^{-1}$ are achieved at 1.1125 GHz and 1.05 GHz, respectively. Finally, a mathematical model is developed to directly relate reflection coefficient measurements to glucose level concentrations, thereby allowing one to non-invasively predict glucose level concentrations via the respective antenna measurements.

System

As used in this application, the terms "component" and "system" are intended to refer to a computer-related entity, either hardware, a combination of hardware and software, software, or software in execution. For example, a component can be, but is not limited to being, a process running on a processor, a processor, an object, an executable, a thread of execution, a program, and/or a computer. By way of illustration, both an application running on a server and the server can be a component. One or more components can reside within a process and/or thread of execution, and a component can be localized on one computer and/or distributed between two or more computers.

Generally, program modules include routines, programs, components, data structures, etc., that perform particular tasks or implement particular abstract data types. Moreover, those skilled in the art will appreciate that the inventive methods can be practiced with other computer system configurations, including single-processor or multiprocessor computer systems, minicomputers, mainframe computers, as well as personal computers, hand-held computing devices, microprocessor-based or programmable consumer electronics, and the like, each of which can be operatively coupled to one or more associated devices.

The illustrated aspects of the innovation may also be practiced in distributed computing environments where certain tasks are performed by remote processing devices that are linked through a communications network. In a distributed computing environment, program modules can be located in both local and remote memory storage devices.

A computer typically includes a variety of computer-readable media. Computer-readable media can be any available media that can be accessed by the computer and includes both volatile and nonvolatile media, removable and non-removable media. By way of example, and not limitation, computer-readable media can comprise computer storage media and communication media. Computer storage media includes volatile and nonvolatile, removable and non-removable media implemented in any method or technology for storage of information such as computer-readable instructions, data structures, program modules or other data. Computer storage media includes, but is not limited to, RAM, ROM, EEPROM, flash memory or other memory technology, CD-ROM, digital versatile disk (DVD) or other optical disk storage, magnetic cassettes, magnetic tape, magnetic disk storage or other magnetic storage devices, or any other medium which can be used to store the desired information and which can be accessed by the computer.

Communication media typically embodies computer-readable instructions, data structures, program modules or other data in a modulated data signal such as a carrier wave or other transport mechanism, and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of the any of the above should also be included within the scope of computer-readable media.

Software includes applications and algorithms. Software may be implemented in a smart phone, tablet, or personal computer, in the cloud, on a wearable device, or other computing or processing device. Software may include logs, journals, tables, games, recordings, communications, SMS messages, Web sites, charts, interactive tools, social networks, VOIP (Voice Over Internet Protocol), e-mails, and videos.

In some embodiments, some or all of the functions or process(es) described herein and performed by a computer program that is formed from computer readable program code and that is embodied in a computer readable medium. The phrase "computer readable program code" includes any type of computer code, including source code, object code, executable code, firmware, software, etc. The phrase "computer readable medium" includes any type of medium capable of being accessed by a computer, such as read only memory (ROM), random access memory (RAM), a hard disk drive, a compact disc (CD), a digital video disc (DVD), or any other type of memory.

All publications and patent applications mentioned in this specification are herein incorporated by reference to the same extent as if each individual publication or patent application was specifically and individually indicated to be incorporated by reference.

While the invention has been described in connection with various embodiments, it will be understood that the invention is capable of further modifications. This application is intended to cover any variations, uses or adaptations of the invention following, in general, the principles of the invention, and including such departures from the present disclosure as, within the known and customary practice within the art to which the invention pertains.

What is claimed is:

1. A sensor composed of an antenna to non-invasively detect a concentration of biomarkers comprising:
   a first slotted arch and a second slotted arch disposed on a substrate, wherein the first slotted arch and the second slotted arch are not directly connected through slots;
   the first slotted arch corresponds to the shape of a deep palmar arch, and the second slotted arch corresponds to the shape of a superficial palmar arch;
   the first slotted arch includes at least two slotted main branches that are connected by a λ-slotted branch, wherein a first slotted main branch includes a single slot branch and a Y-shaped branch and a second slotted main branch includes a W-shaped branch, wherein the first slotted main branch, the second slotted main branch, the λ-slotted branch, the single slot branch, the Y-shaped branch, and the W-shaped branch corresponds to dorsal metacarpal veins or palmar digital arteries;

the second slotted arch includes at least four single slots that correspond to palmar digital arteries; and the antenna is configured to transmit electromagnetic waves into human tissues in areas in close proximity to the main palmar veins in order to monitor and detect with high fidelity a variation of the concentration of the biomarkers within the human tissue.

2. The sensor of claim 1, further comprising a spirally shaped feeding transmission line with three turns in a spiral configuration that are positioned on a bottom layer of the substrate such that the transmission line is separated from a sensing surface.

3. The sensor of claim 2, wherein the substrate is a flexible dielectric substrate.

4. The sensor of claim 3, wherein the antenna is configured to resonate and maintain the antenna's sensitivity to the variation of the concentration of the biomarkers when the antenna is placed in close proximity to the human hand.

5. The sensor of claim 4, wherein the antenna is operational at multiple frequencies within the microwave region ranging between about 500 MHz and about 3 GHz.

6. The sensor of claim 5, wherein the substrate includes a thickness between about 0.45 mm and about 0.54 mm; and a Dielectric $\varepsilon_r$ between about 2.80 and about 3.20.

7. A signal processing system operably coupled to the sensor of claim 1 to convert a magnitude and/or a phase of the sensor measured S11 parameters into a concentration of the biomarkers, comprising:

measuring the S11 parameters using the sensor;
preprocessing of the measured S11 parameters;
extracting a feature or a plurality of features;
modeling, calibrating and tuning;
recalibrating model for enhanced accuracy.

8. The system of claim 7, wherein the preprocessing of the S11 parameters comprises outlier and noise removal using different techniques selected from the group consisting of wavelet and moving average filters.

9. The system of claim 7, wherein the extracting features comprises S11 Magnitude, S11 phase and/or impedance sampled into different frequency components; normalizing the features between −1 and 1, removing a reference value equivalent to the values corresponding to the concentration of the biomarkers; removing the mean of each feature; and dividing by the maximum of each feature.

10. The system of claim 7, wherein the modeling, calibrating and tuning comprises using regularized regression to predict glucose concentrations; and the modeling is based on the group selected from: Lasso, PLS, Hybrid models, Single feature model and multiple-feature models, and time based models.

11. The system of claim 7, further comprising design tolerance stretching the substrate selected from the group consisting of: tolerating impedance match reduction as long as the stretched antenna maintains resonance levels moderately below −10 db and the substrate design is configured to maintain resonance levels below −10db under maximum stretching conditions; and tolerating Lower radiation efficiency upon stretching and resolved by increasing an input power; and tolerating a changed response of the stretched design whether on a flexible substrate or other material like.

* * * * *